US011692010B2

(12) United States Patent
Wang et al.

(10) Patent No.: US 11,692,010 B2
(45) Date of Patent: Jul. 4, 2023

(54) COMPOUNDS THAT BIND TO HUMAN IMMUNODEFICIENCY VIRUS REV RESPONSE ELEMENT

(71) Applicant: The United States of America, as represented by the Secretary, Dept. of Health and Human Services, Bethesda, MD (US)

(72) Inventors: Yun-Xing Wang, Columbia, MD (US); Ping Yu, Frederick, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 741 days.

(21) Appl. No.: 16/664,523

(22) Filed: Oct. 25, 2019

(65) Prior Publication Data
US 2020/0048310 A1 Feb. 13, 2020

Related U.S. Application Data

(63) Continuation of application No. 15/031,232, filed as application No. PCT/US2014/061975 on Oct. 23, 2014, now Pat. No. 10,464,970.

(60) Provisional application No. 61/934,379, filed on Jan. 31, 2014, provisional application No. 61/894,849, filed on Oct. 23, 2013.

(51) Int. Cl.
| | |
|---|---|
| C07K 14/00 | (2006.01) |
| G01N 33/569 | (2006.01) |
| A61K 47/64 | (2017.01) |
| A61K 38/17 | (2006.01) |
| A61K 45/06 | (2006.01) |
| A61K 49/00 | (2006.01) |
| A61K 49/14 | (2006.01) |
| A61K 51/08 | (2006.01) |
| A61K 38/00 | (2006.01) |
| C12Q 1/70 | (2006.01) |

(52) U.S. Cl.
CPC .............. *C07K 14/00* (2013.01); *A61K 38/17* (2013.01); *A61K 45/06* (2013.01); *A61K 47/64* (2017.08); *A61K 49/0056* (2013.01); *A61K 49/14* (2013.01); *A61K 51/088* (2013.01); *G01N 33/56988* (2013.01); *A61K 38/00* (2013.01); *C12N 2740/16011* (2013.01); *C12Q 1/703* (2013.01); *G01N 2333/16* (2013.01)

(58) Field of Classification Search
CPC ........ C07K 14/00; A61K 47/64; A61K 38/17; A61K 45/06; A61K 49/0056; A61K 51/088; A61K 49/14; A61K 38/00; G01N 33/56988; G01N 2333/16; C12N 2740/16011; C12Q 1/703
See application file for complete search history.

(56) References Cited

U.S. PATENT DOCUMENTS

| | | | |
|---|---|---|---|
| 4,795,739 | A | 1/1989 | Lifson et al. |
| 5,534,408 | A | 7/1996 | Green et al. |
| 6,013,517 | A | 1/2000 | Respess et al. |
| 6,020,488 | A | 2/2000 | Wuonola et al. |
| 7,160,992 | B2 | 1/2007 | Lapidot et al. |
| 8,445,431 | B2 | 5/2013 | Cowan et al. |
| 2008/0318797 | A1 | 12/2008 | Yu |
| 2012/0238029 | A1 | 9/2012 | Nakatani et al. |

FOREIGN PATENT DOCUMENTS

| | | |
|---|---|---|
| EP | 1604993 | 12/2005 |
| WO | WO 94/29487 | 12/1994 |

OTHER PUBLICATIONS

Fernandes J, Jayaraman B, Frankel A. The HIV-1 Rev response element: an RNA scaffold that directs the cooperative assembly of a homo-oligomeric ribonucleoprotein complex. RNA Biol. Jan. 2012;9(1):6-11. Epub Jan. 1, 2012. (Year: 2012).*

Shuck-Lee D, Chang H, Sloan EA, Hammarskjold ML, Rekosh D. Single-nucleotide changes in the HIV Rev-response element mediate resistance to compounds that inhibit Rev function. J Virol. Apr. 2011;85(8):3940-9. Epub Feb. 2, 2011. (Year: 2011).*

Sherpa C, Rausch JW, Le Grice SF, Hammarskjold ML, Rekosh D. The HIV-1 Rev response element (RRE) adopts alternative conformations that promote different rates of virus replication. Nucleic Acids Res. May 19, 2015;43(9):4676-86. Epub Apr. 8, 2015. (Year: 2015).*

Chu CC, Plangger R, Kreutz C, Al-Hashimi HM. Dynamic ensemble of HIV-1 RRE stem IIB reveals non-native conformations that disrupt the Rev-binding site. Nucleic Acids Res. Jul. 26, 2019;47(13):7105-7117. (Year: 2019).*

McColl DJ, Honchell CD, Frankel AD. Structure-based design of an RNA-binding zinc finger. Proc Natl Acad Sci U S A. Aug. 17, 1999;96(17):9521-6. doi: 10.1073/pnas.96.17.9521. PMID: 10449725; PMCID: PMC22241. (Year: 1999).*

(Continued)

*Primary Examiner* — Rachel B Gill
(74) *Attorney, Agent, or Firm* — Klarquist Sparkman, LLP

(57) ABSTRACT

Compounds (such as peptides or peptide mimetics) that bind to HIV RRE RNA are provided. In some examples, the compounds inhibit (for example, decrease) binding of Rev to the RRE RNA. In some embodiments, the compounds include two moieties, each of which bind to one of the Rev binding sites in the RRE. In some examples, the moieties include peptides or small molecules. In some examples, the peptides include an arginine-rich motif. The RRE binding compounds may be further linked to a detectable label or cargo moiety. Also provided are methods of treating or inhibiting HIV including administering one or more of the RRE binding compounds to a subject.

11 Claims, 18 Drawing Sheets
Specification includes a Sequence Listing.

(56) References Cited

OTHER PUBLICATIONS

Mills NL, Daugherty MD, Frankel AD, Guy RK. An alpha-helical peptidomimetic inhibitor of the HIV-1 Rev-RRE interaction. J Am Chem Soc. Mar. 22, 2006;128(11):3496-7. (Year: 2006).*

Aoyama S, Sugaya M, Kobayashi C, Masuda K, Maeda T, Sakamoto T, Kawai G, Katoh A, Harada K. An isostructural G-G to A-A substitution within the HIV RRE RNA switches the specificity towards arginine-rich peptides. Nucleic Acids Symp Ser (Oxf). 2009;(53):271-2. doi: 10.1093/nass/nrp136. PMID: 19749365. (Year: 2009).*

Apgar et al., "AB-Bind: Antibody binding mutational database for computational affinity predictions," *Protein Science*, vol. 25, pp. 393-409, 2015.

Bayer et al., "Arginine-Rich Motifs Present Multiple Interfaces for Specific Binding by RNA," *RNA*, vol. 11, No. 12, pp. 1848-1857, 2005.

Casu et al., "The Arginine-Rich RNA-Binding Motif of HIV-1 Rev is Intrinsically Disordered and Folds upon RRE Binding," *Biophysical Journal*, vol. 105, No. 4, pp. 1004-1017, 2013.

Daugherty et al., "HIV Rev response element (RRE) directs assembly of the Rev homooligomer into discrete asymmetric complexes," *Proc. Natl. Acad. Sci. USA* vol. 107, No. 28, pp. 12481-12486, 2010.

Daugherty et al., "Structural basis for cooperative RNA binding and export complex assembly by HIV Rev," *Nature Structural & Molecular Biology*, vol. 17, No. 11, pp. 1337-1342, 2010.

DeJong et al., "Proflavine Acts as a Rev Inhibitor by Targeting the High-Affinity Rev Binding Site of the Rev Responsive Element of HIV-1," *Biochemistry*, vol. 42, No. 26, pp. 8035-8046, 2003.

Dimattia et al., "Implications of the HIV-1 Rev dimer structure at 3.2 Å resolution for multimeric binding to the Rev response element," *Proc. Natl. Acad. Sci. USA* vol. 107, No. 13, pp. 5810-5814, 2010.

Fang et al., "An Unusual Topological Structure of the HIV-1 Rev Response Element," *Cell*, vol. 155, No. 3, pp. 594-605, 2013.

Gosser et al., "Peptide-triggered conformational switch in HIV-1 RRE RNA complexes," *Natural Structural Biology*, vol. 8, No. 2, pp. 146-150, 2001.

Kay, "Silent, but deadly—eliminating reservoirs of latent HIV," *Trends Biotechnol.*, vol. 21, No. 10, pp. 420-423, 2003.

Kjems et al., "Specific binding of a basic peptide from HIV-1 Rev," *EMBO J.*, vol. 11, No. 3, pp. 1119-1129, 1992.

Luedtke, et al., "RNA-Ligand Interactions: Affinity and Specificity of Aminoglycoside Dimers and Acridine Conjugates to the HIV-1 Rev Response Element," *Biochemistry*, vol. 42, No. 39, pp. 11391-11403, 2003.

NG et al., "Structural characterization and anti-HIV-1 activities of arginine/glutamate-rich polypeptide Luffin P1 from the seeds of sponge gourd (*Luffa cylindrica*)," *Journal of Structural Biology*, vol. 174, No. 1, pp. 164-172, 2011.

Peled-Zehavi et al., "Selection of RRE RNA binding peptides using a kanamycin antitermination assay," *RNA*, vol. 9, No. 2, pp. 252-261, 2003.

Sugaya et al., "Tailoring the Peptide-Binding Specificity of an RNA by Combinations of Specificity-Altering Mutations," *Nucleosides, Nucleotides & Nucleic Acids*, vol. 27, No. 5, pp. 534-545, 2008.

Tan et al., "RNA Recognition by an Isolated α Helix," *Cell*, vol. 73, pp. 1031-1040, 1993.

Waheed et al., "Methods for the Study of HVI-1 Assembly," *HIV Protocols: Second Edition*, Prasad et al., Eds., vol. 485, pp. 163-184, 2009.

Zapp et al., "Small Molecules That Selectively Block RNA Binding of HIV-1 Rev Protein Inhibit Rev Function and Viral Production," *Cell*, vol. 74, pp. 969-978, 1998.

\* cited by examiner

FIG. 1B
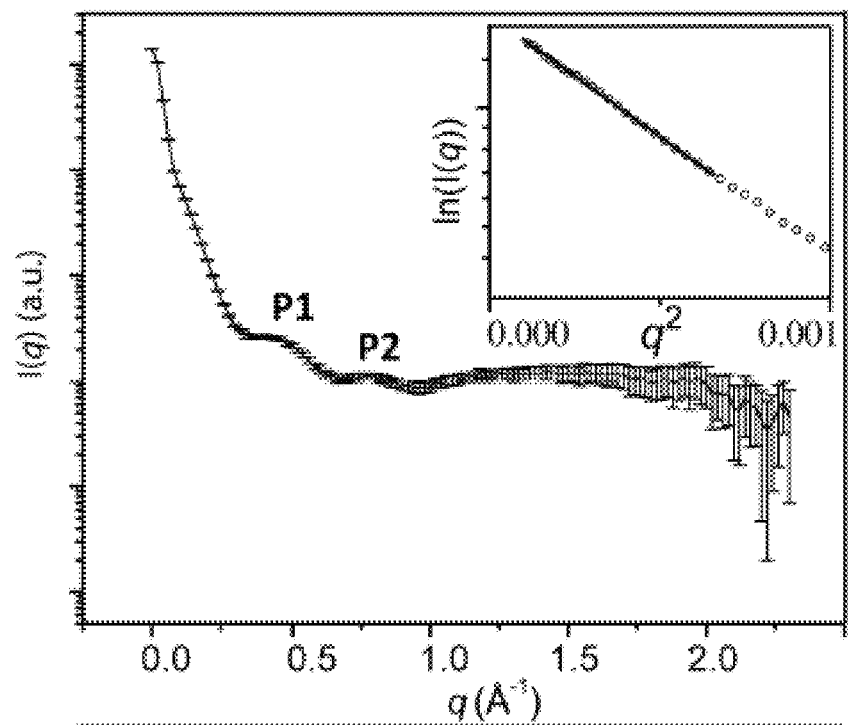
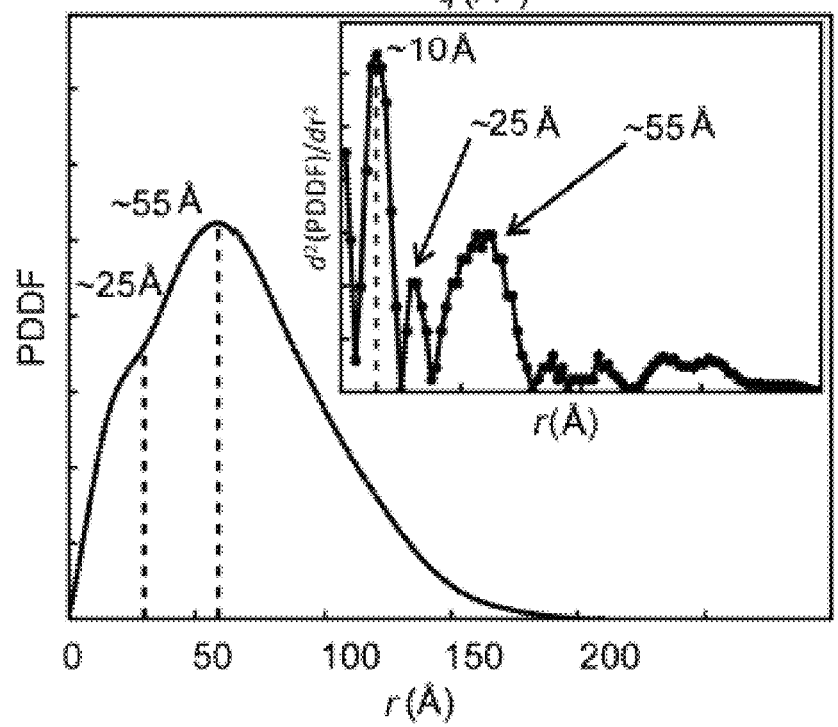
FIG. 1C

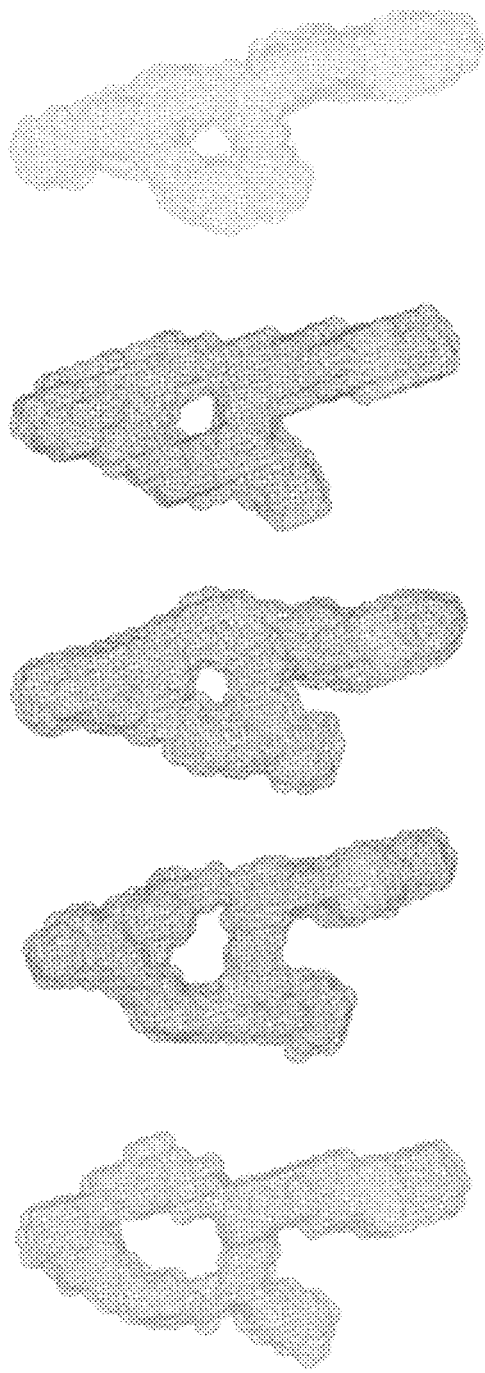
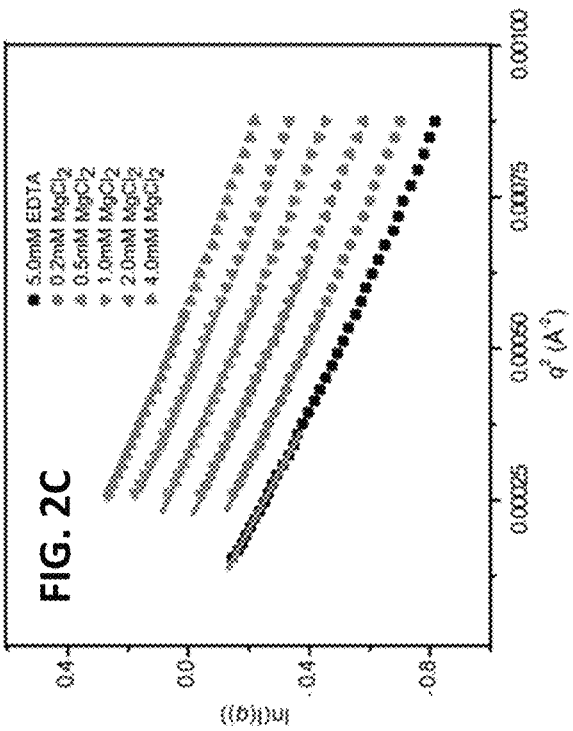
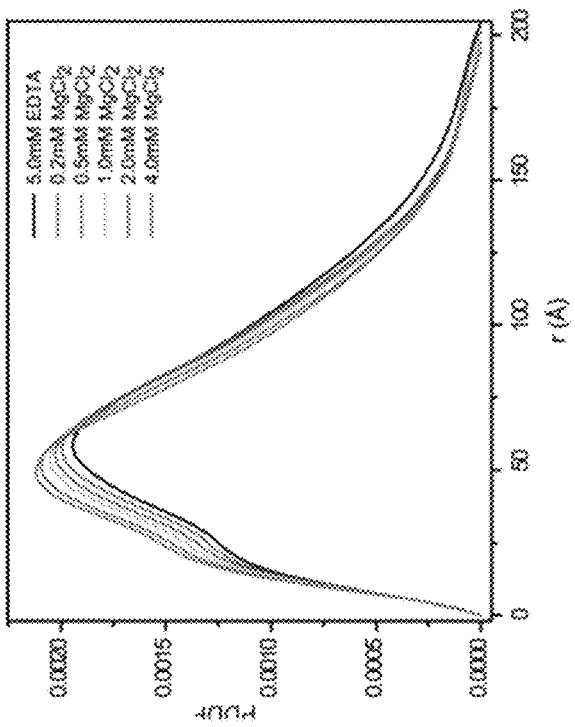
FIG. 2A
FIG. 2B
FIG. 2C

FIG. 4A
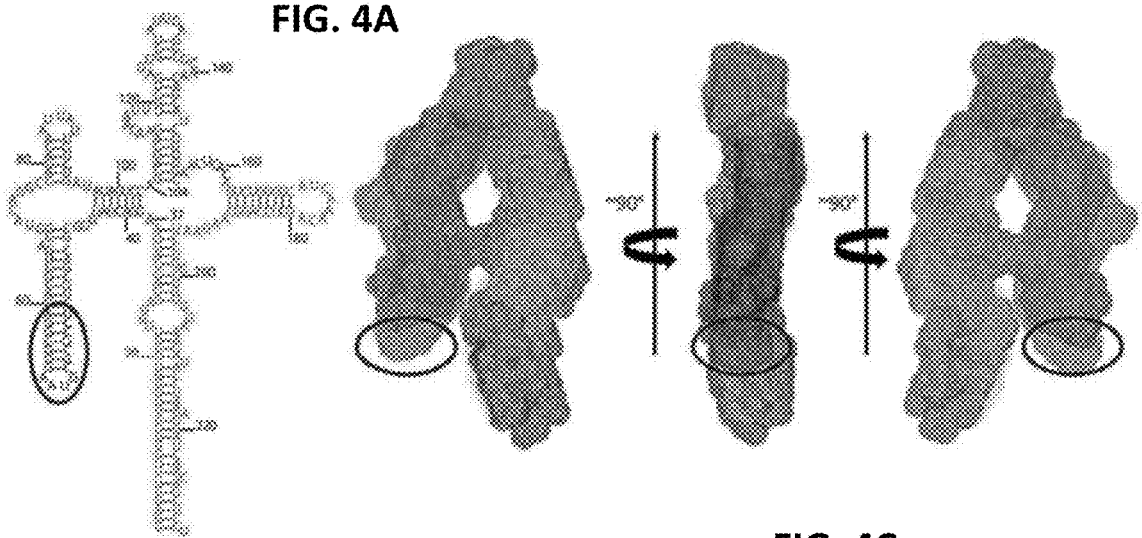
FIG. 4C
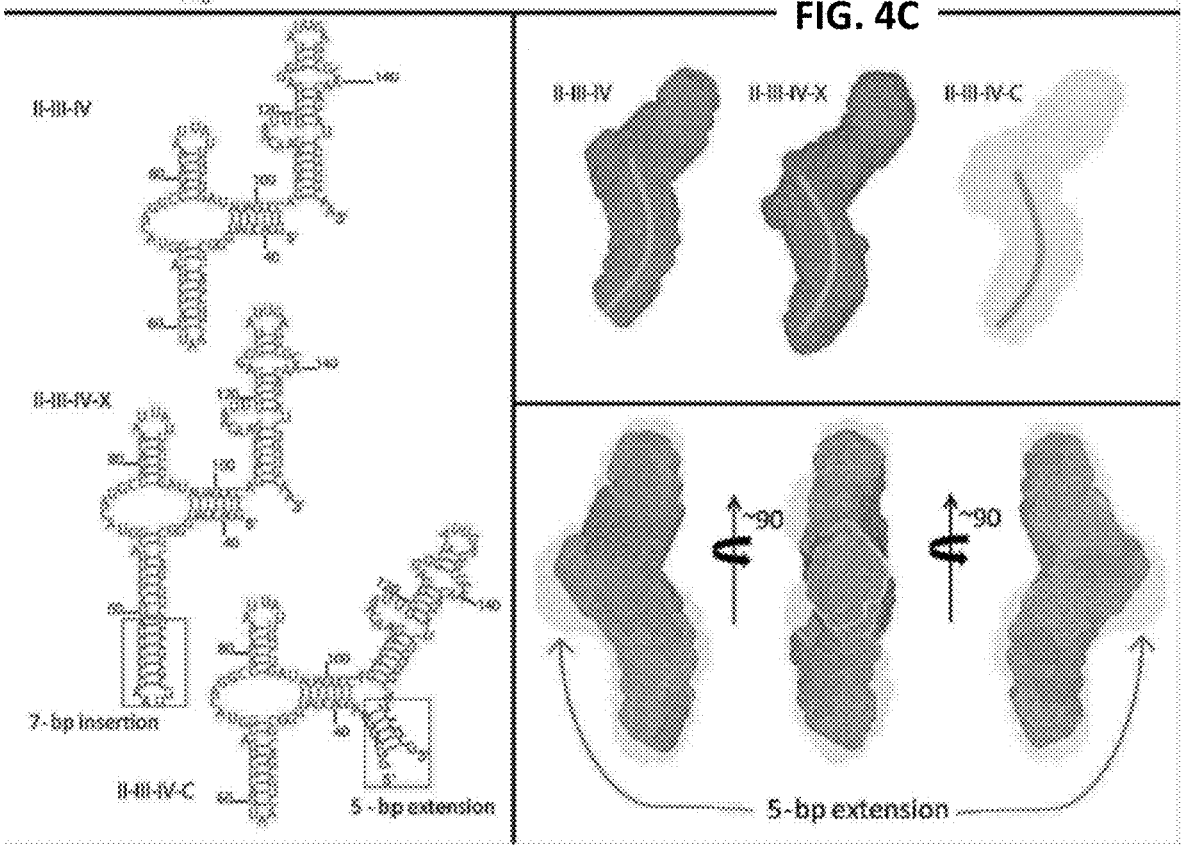
FIG. 4B
FIG. 4D

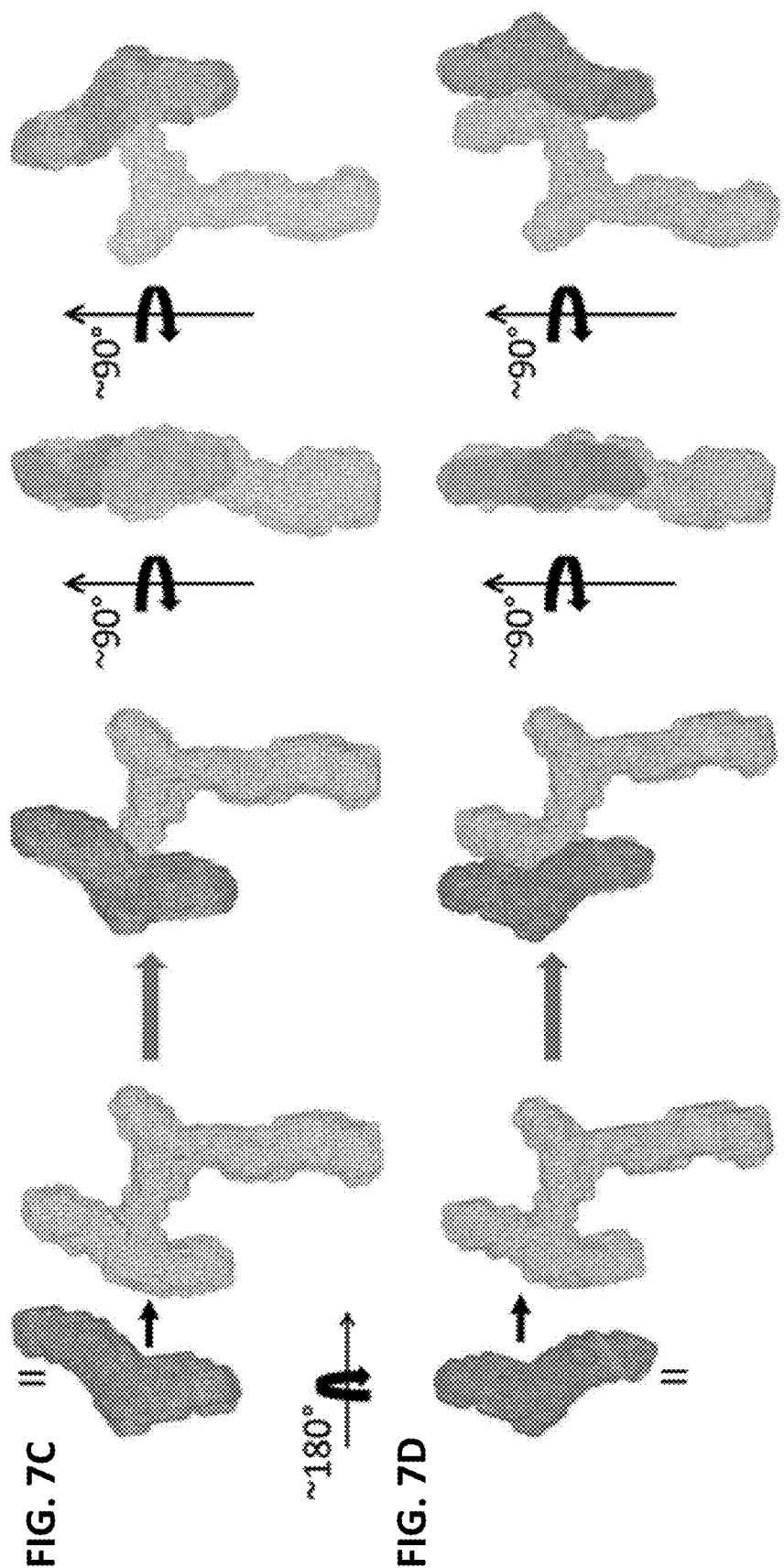

COMPOUNDS THAT BIND TO HUMAN IMMUNODEFICIENCY VIRUS REV RESPONSE ELEMENT

CROSS REFERENCE TO RELATED APPLICATIONS

This is a continuation of co-pending U.S. application Ser. No. 15/031,232, filed Apr. 21, 2016, which is the § 371 U.S. National Stage of International Application No. PCT/US2014/061975, filed Oct. 23, 2014, which was published in English under PCT Article 21(2), which in turn claims the benefit of U.S. Provisional Application No. 61/894,849, filed Oct. 23, 2013, and U.S. Provisional Application No. 61/934,379, filed Jan. 31, 2014, all of which are incorporated herein by reference in their entirety.

FIELD

This disclosure relates to compounds that bind to human immunodeficiency virus Rev response element, particularly compounds that inhibit binding of Rev to the Rev response element, and methods of their use.

BACKGROUND

Nuclear export of unspliced and singly spliced human immunodeficiency virus (HIV) RNA is one of the essential steps in the viral life cycle. It requires the specific and cooperative interaction and oligomerization of the viral encoded protein Rev with the structured RNA element Rev response element (RRE). This interaction is key to the viral ability to recognize its own genomic RNA among much more abundant host RNAs. Currently all anti-HIV drugs target viral proteins, rather than viral RNAs. The RRE presents a unique target for development of new compounds for treatment of HIV.

SUMMARY

Disclosed herein are compounds that bind to HIV RRE RNA (for example, HIV type 1 (HIV-1) or HIV type 2 (HIV-2) RRE RNA). In some examples, the compounds (referred to herein in some examples as "RRE-binders" or "RRE binding compounds") inhibit or decrease binding of Rev to the HIV RRE RNA. In some embodiments, the compounds include two moieties, each of which bind to one of two Rev binding sites in the RRE. The two moieties are joined or linked together, in some examples by a linkage of about 30-80 Å. In some examples, the moieties are covalently linked, either directly or by a linker. In some examples, the moieties include peptides, small organic molecules, or combinations thereof. In some examples, the moieties include two linked peptides, for example peptides including an arginine-rich motif (ARM) and variants thereof (such as retro-inverso peptides). Exemplary peptides include SEQ ID NOs: 1-20 disclosed herein. In other examples, the moieties include two linked small organic molecules. Exemplary small organic molecules include aminoglycoside antibiotics (such as neomycin B). In still further examples, the moieties include a peptide and a small organic molecule (such as an aminoglycoside antibiotic and a peptide).

In additional embodiments, the disclosed RRE binders further include a detectable label (such as a radioactive, fluorescent, or chemiluminescent compound). In still further embodiments, the disclosed RRE binders further include a cargo moiety (such as a radioisotope, a free radical generator, an RNA cleavage agent, nucleic acid crosslinking agent, and/or a cytotoxin).

Also disclosed herein are methods of inhibiting binding of Rev to the RRE by contacting an RRE (such as an RRE in a cell) with a compound that inhibits Rev binding, such as one or more of the RRE binders disclosed herein. In some embodiments, the methods also include treating or inhibiting HIV-1 infection by administering to a subject one or more compounds that inhibit Rev binding to an RRE, such as the RRE binders disclosed herein.

Further disclosed herein are methods of identifying cells containing HIV RRE and/or delivering a cargo moiety to cells containing HIV RRE. In some embodiments, methods of identifying cells that contain HIV RRE include contacting cells with one or more of the disclosed RRE binders that further include a detectable label and detecting the label. Presence of the detectable label in a cell indicates that the cell contains HIV RRE (e.g., is infected with HIV). In some examples, the methods include contacting cells with the compound in vitro or in vivo (such as administering the compound including the detectable label to a subject). In other embodiments, the methods include delivering a cargo moiety to cells containing HIV RRE (e.g., cells infected with HIV) by contacting cells with one or more of the disclosed RRE binders that further include a cargo moiety (such as a radioisotope, a free radical generator, an RNA cleavage agent, nucleic acid crosslinking agent, and/or a cytotoxin). In some examples, the method includes contacting cells with the compound in vitro or in vivo (such as administering the RRE binder including a cargo moiety to a subject).

The foregoing and other features of the disclosure will become more apparent from the following detailed description, which proceeds with reference to the accompanying figures.

BRIEF DESCRIPTION OF THE DRAWINGS

FIGS. 1A-1F are a series of panels showing schematic location of the RRE in the HIV-1 genomic RNA, the RRE secondary structure, small angle X-ray scattering (SAXS) analysis and the molecular envelope. FIG. 1A shows the genomic location and secondary structure of the RRE (SEQ ID NO: 30). The ovals in the secondary structure highlight the two known primary binding sites for Rev. FIG. 1B shows scattering intensity in arbitrary units vs. momentum transfer q in $Å^{-1}$. Note that the SAXS/wide angle X-ray scattering (WAXS) data was recorded up to $q=2.3$ $Å^{-1}$, corresponding to a convoluted spatial resolution of ~2.8 Å. The fine features of P1 and P2 in the scattering curve arise from helical inter-strand pair distance correlation and reflect scattering interference among electrons within major and minor groves (Zuo et al., *Proc Natl Acad Sci USA* 103:3534-3539, 2006). The inset shows the Guinier region of the scattering curve with a linear fit line. FIG. 1C shows pair distance distribution function (PDDF) with the inset showing the absolute value of the second derivative of the PDDF. The PDDF profile was calculated using GNOM ($q_{max}=0.30$). The second derivative of the PDDF (inset) gives approximate peak positions of populated pair distances in the RRE. FIG. 1D is a dimensionless Kratky plot of the RRE (dotted line) and adenine riboswitch (PDB Accession No. 1Y26) (solid line). FIG. 1E shows the Porod-Debye plot of the RRE (dotted line) and adenine riboswitch (solid line). FIGS. 1D and E indicate that the RRE structure is more extended and open than the adenine riboswitch. FIG. 1F shows a series of panels with the molecular envelope of the RRE RNA drawn in mesh. A scale bar of 30 Å indicates the relative dimension of the RRE envelope. The spatial resolution of the envelope is ~21 Å.

FIGS. 2A-2C are a series of panels showing the 3D Envelopes (FIG. 2A), PDDF (FIG. 2B), and Guinier Plots (FIG. 2C) for RRE RNA at various $Mg^{2+}$ concentrations. The overall shapes of the envelopes remain largely unchanged, even though the envelopes appear to be smaller as $Mg^{2+}$ concentration increases. The "shrinking" envelope, due to counter ions screening, is consistent with $R_g$ and $D_{max}$ values (Table 2) and the gradual shift of the maximum peak position of the PDDF toward smaller distances as the $Mg^{2+}$ concentration is increased (FIG. 2B, from 5.0 mM EDTA to 4.0 mM $MgCl_2$, lines from bottom to top of plot). The data quality is good as indicated by the linearity of the Guinier region (FIG. 2C).

FIGS. 4A-4F are a series of panels showing location determination of the RRE domains, coaxial stacking in domains II-III-IV and approximate location of IA. FIG. 4A shows a construct with the extended IIB stem loop (the circled nucleotides in the secondary structure on the left (SEQ ID NO: 30)) used to determine whether IIB is located on the top of the 'A' or at the end of the shorter leg. Circles indicate the approximate location of the extension. Therefore, domain IIB is located at the low part of the shorter leg. FIG. 4B shows the secondary structures for subconstruct II-III-IV (SEQ ID NO: 31; top), II-III-IV-X (SEQ ID NO: 33; middle) and II-III-IV-C (SEQ ID NO: 34; bottom). The 7-bp inserted duplex at region IIB in sub-construct II-III-IV-X and an addition of 5-bp duplex that closes domain II and III-IV in subconstruct II-III-IV-C are highlighted with boxes. FIG. 4C shows the bead models for subconstructs II-III-IV (left), II-III-IV-X (middle) and II-III-IV-C (right). The curvatures, drawn as thick lines, indicate that there is a bend at the junction between domains III and IV. FIG. 4D shows superposition of the bead model of subconstruct II-III-IV on that of II-III-IV-C at three different views. The extra mass (indicated by arrows) in the middle section of the II-III-IV-C bead model is likely from the 5-bp closing duplex. FIG. 4E shows envelope of Domain I subconstruct and estimation of the location of the IA binding site based on distance/bp for an A-form duplex and the number of base pairs in domain I. The approximate location of IA is highlighted in light gray. FIG. 4F shows a summary of the RRE domain locations in the topological structure (SEQ ID NO: 30). The approximate locations of IIB and IA in the RRE topology structure are highlighted. The distance between the two locations, measured from the centers, is ~55 Å, similar to the span between the two N-terminal domains in the Rev dimer (Daugherty et al., *Proc Natl Acad Sci USA* 107:12481-12486, 2010; DiMattia et al., *Proc Natl Acad Sci USA* 107:5810-5814, 2010).

FIG. 5A shows superimposition of the putative RRE structural model in ribbon with the SAXS envelope in mesh. The four-way junction, three-way junction, and the two known primary Rev binding sites are marked. The distance between the two binding sites is about 55 Å. The points A and B on the top of the envelope are also labeled. Domain II structure was generated based on its homology to an adenine riboswitch (FIG. 11). FIG. 5B shows the back-calculated scattering curves with Ne=3 (thick line) superimposed on the experimental SAXS-WAXS curves (thin line with error bars) (left). The inset (right) shows the $\chi^2$ between experimental and back-calculated SAXS-WAXS curves vs. the ensemble size, Ne, used in the calculation; top right: an expanded high-q region of the superimposed scattering curves on the left; bottom right: residual differences in scattering curves between the top 20 structures in the ensemble and the average experimental data. FIG. 5C shows pairwise RMSD of the top 20 ensembles with Ne=3. The RMSD of residue j between structures a and b is defined as:

Figure 5A:
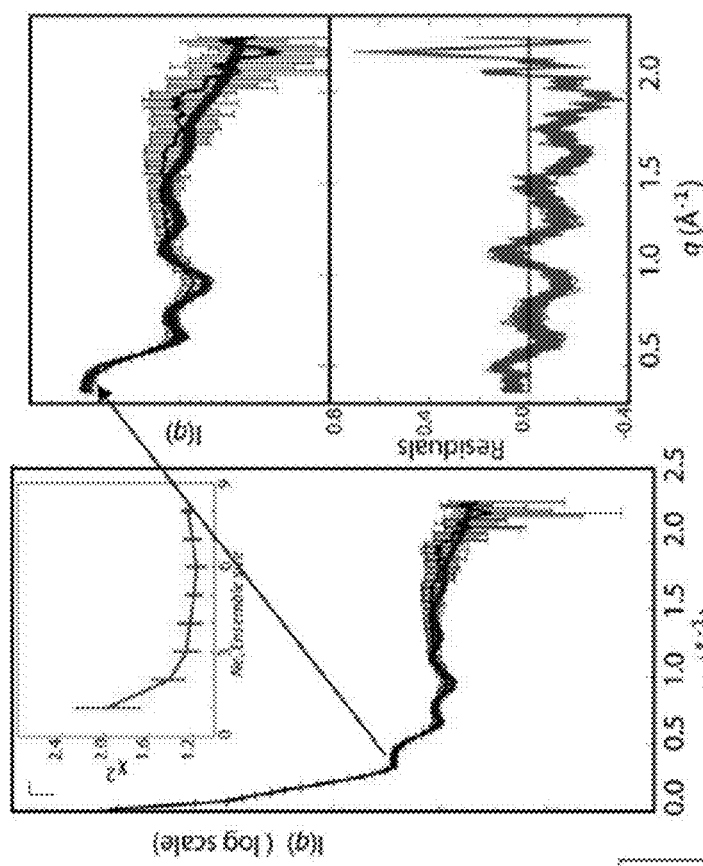
FIGS. 5A-5E show the putative structural model of the RRE, fitness to the experimental SAXS data, pairwise RMSD of the top 20 ensemble structures and histograms of characteristic distance distributions of the RRE RNA.
Figure 5B:
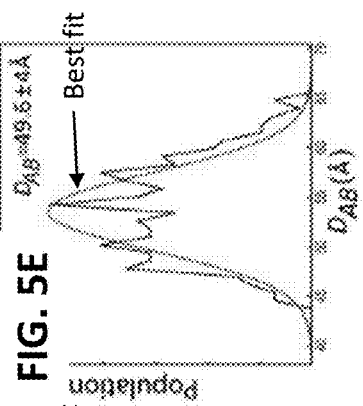
Figure 5C:
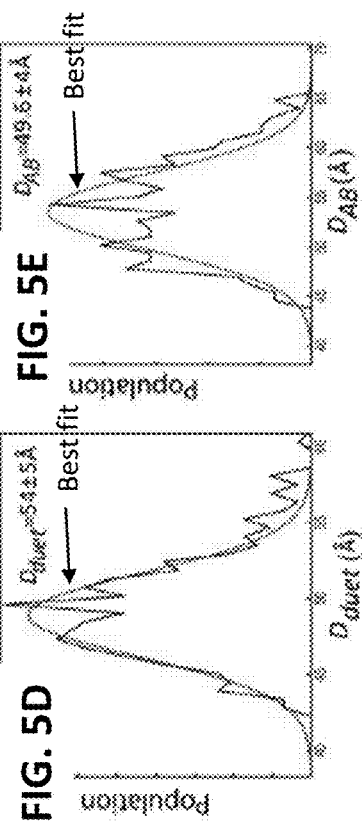
Figure 5D:
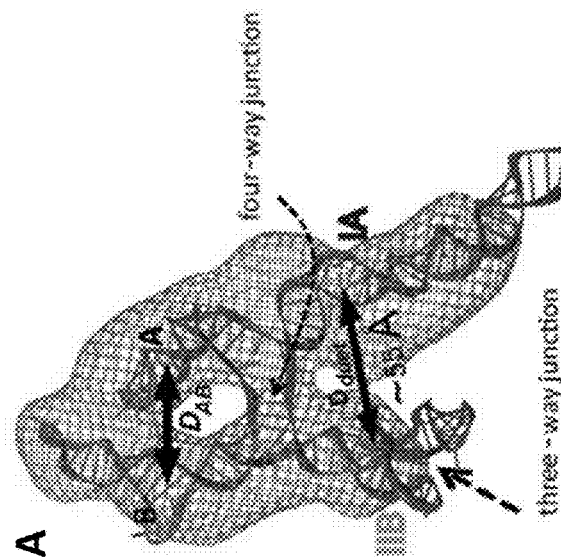
Figure 5E:
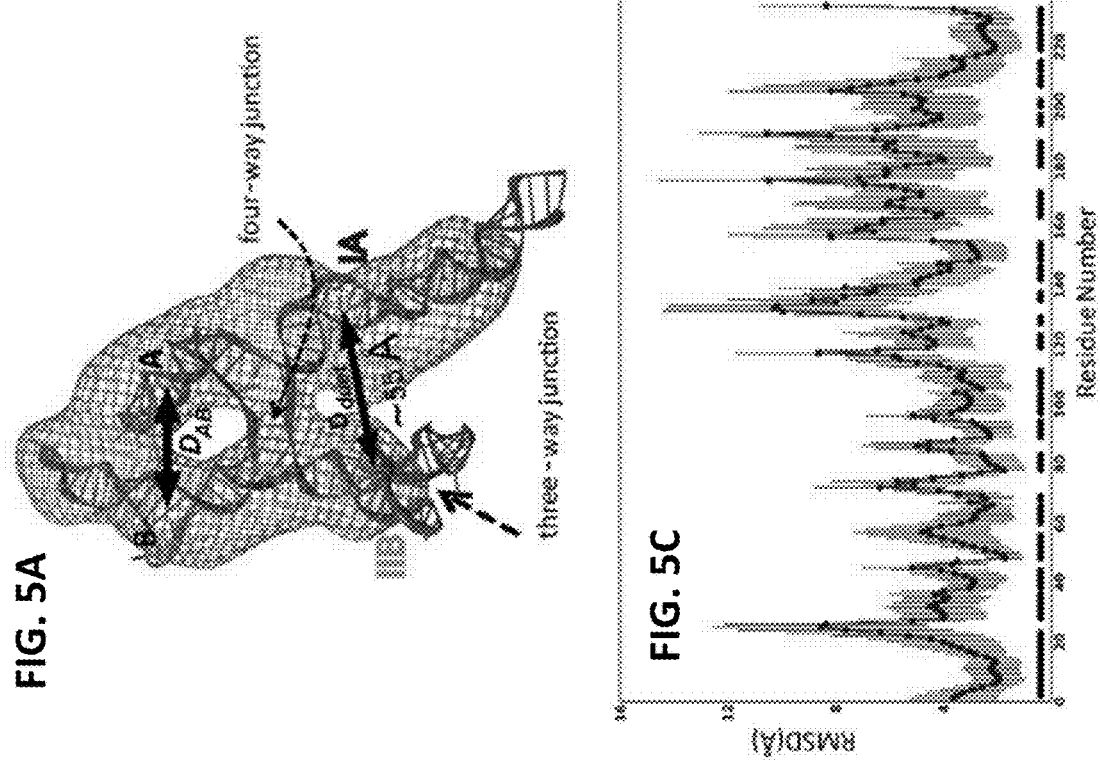

$$RMSD(j) = RMSd(a^j, b^j) = \sqrt{\frac{1}{N}\sum_{i=1}^{N}(a_{ix}^j - b_{ix}^j)^2 + (a_{iy}^j - b_{iy}^j)^2 + (a_{iz}^j - b_{iz}^j)^2}$$

where N is the number of heavy atoms in residue j. The average RMSD (dots connected with solid line) and standard deviation (error bars) of residues are calculated for the top 20 ensembles. Residues in duplexes are labeled with black thick lines at the bottom of the plot. The pattern of the pairwise RMSD almost parallels that of reactivity by chemical probing (Legiewicz et al., *Proc Natl Acad Sci USA* 105:14365-14370, 2008). FIGS. 5D and 5E show histograms of the distance between the duet of the binding sites IIB and IA, $D_{duet}$ (FIG. 5D) and between points A and B, $D_{AB}$, at the top of the "A" of the ensembles (FIG. 5E). The distances between the centers of mass of phosphate atoms of residues (47G, 70G, 46G, 72A)$_{IIB}$ and (24G, 206A, 25G, 205G)$_{IA}$ are taken as the approximate distance between the IIB and IA duet of binding sites, while the locations of A and B are defined as the centers of the phosphates of residues 16G and 225U. The best fits to the histograms assuming a Gaussian distribution are also shown.

Figure 6:
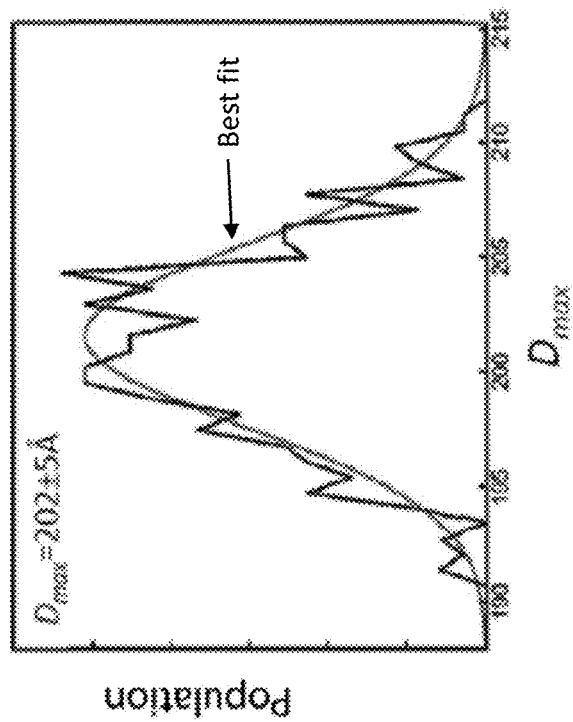
Figure 6:
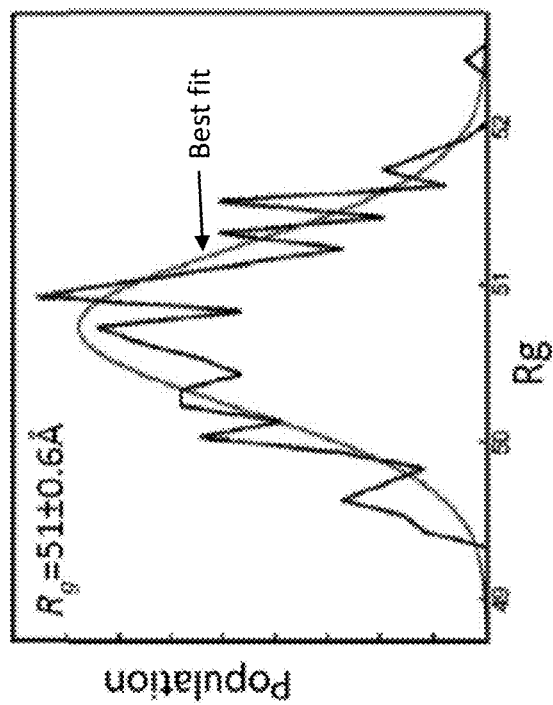

FIG. 6 is a pair of panels showing histograms of the distributions of radius of gyration (left) and maximum distance (right). The best fits to the histograms assuming a Gaussian distribution are also shown.

Figures 7A, 7B:
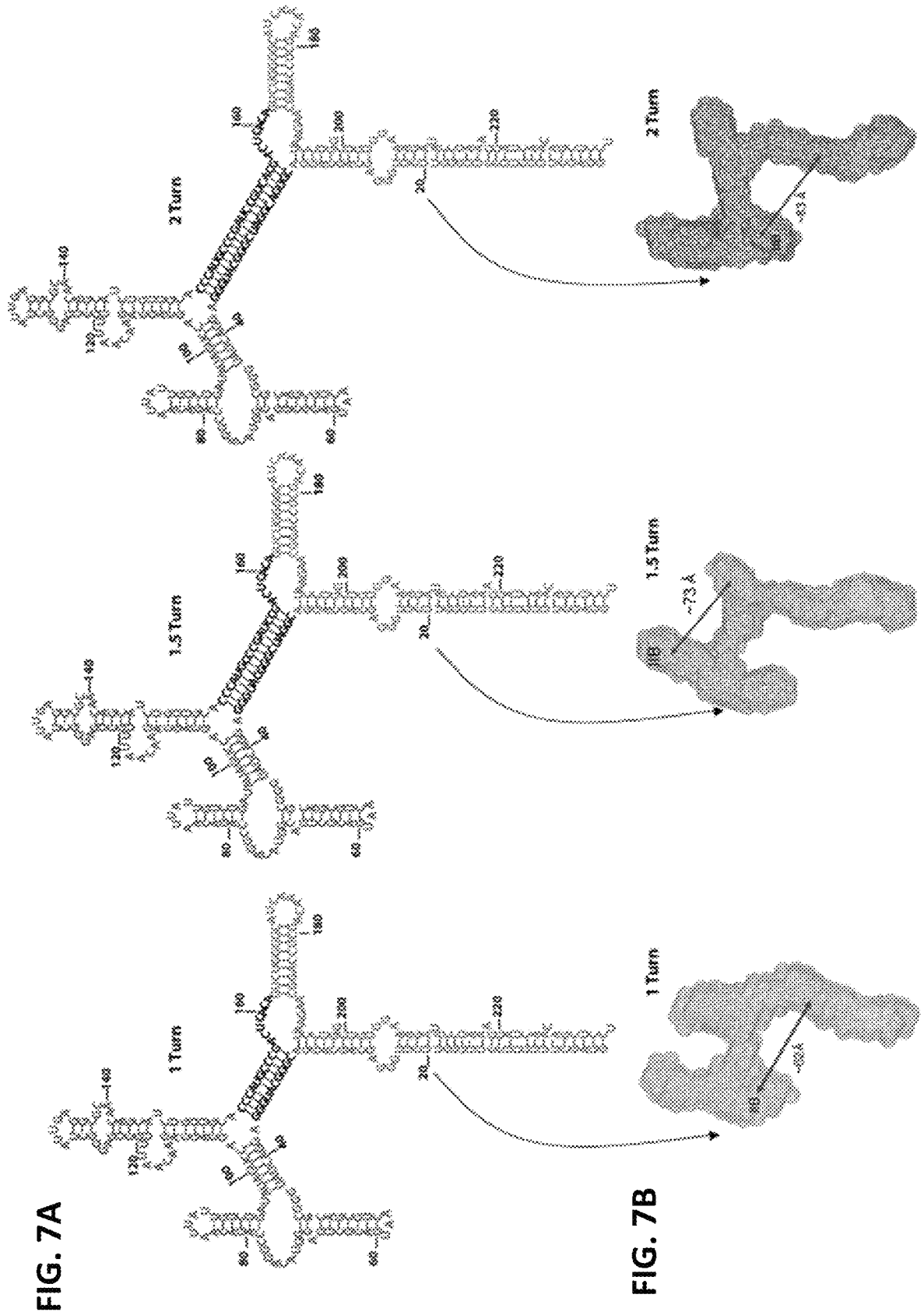

FIGS. 7A-7D are a series of panels showing the secondary structures and molecular envelopes of the insertion mutants. FIG. 7A shows secondary structures of the three insertion mutants (SEQ ID NOs: 35-37, left to right). Domains II-III-IV and I—V are shown in lighter type (left and right portions of the structures, respectively) and the inserted segments are shown in dark black type. FIG. 7B shows the SAXS-derived envelopes of 1 Turn (left), 1.5 Turns (middle) and 2 Turns (right) mutants. Double-headed arrows indicate approximate distances of the separations between the IIB site and the centers of the opposing envelopes of domains I-V. Note that domain II-III-IV in the 1.5 Turn insertion mutant is rotated by 180° relative to domain I-V around the horizontal axis (see FIGS. 4C and 4D). FIG. 7C is an illustration of a 180° rotation of domains II-III-IV about the horizontal axis in the 1.5 Turn insertion mutant. The envelope of domain II-III-IV in dark gray (far left) can be fitted to that of the 1.5 Turn insertion mutant only if the domains are rotated by 180° around the horizontal axis (three views on right). FIG. 7D shows that without the rotation, the envelope of domain II-III-IV cannot be fitted to the short leg of the insertion mutant (three views on the right).

Figure 8A:
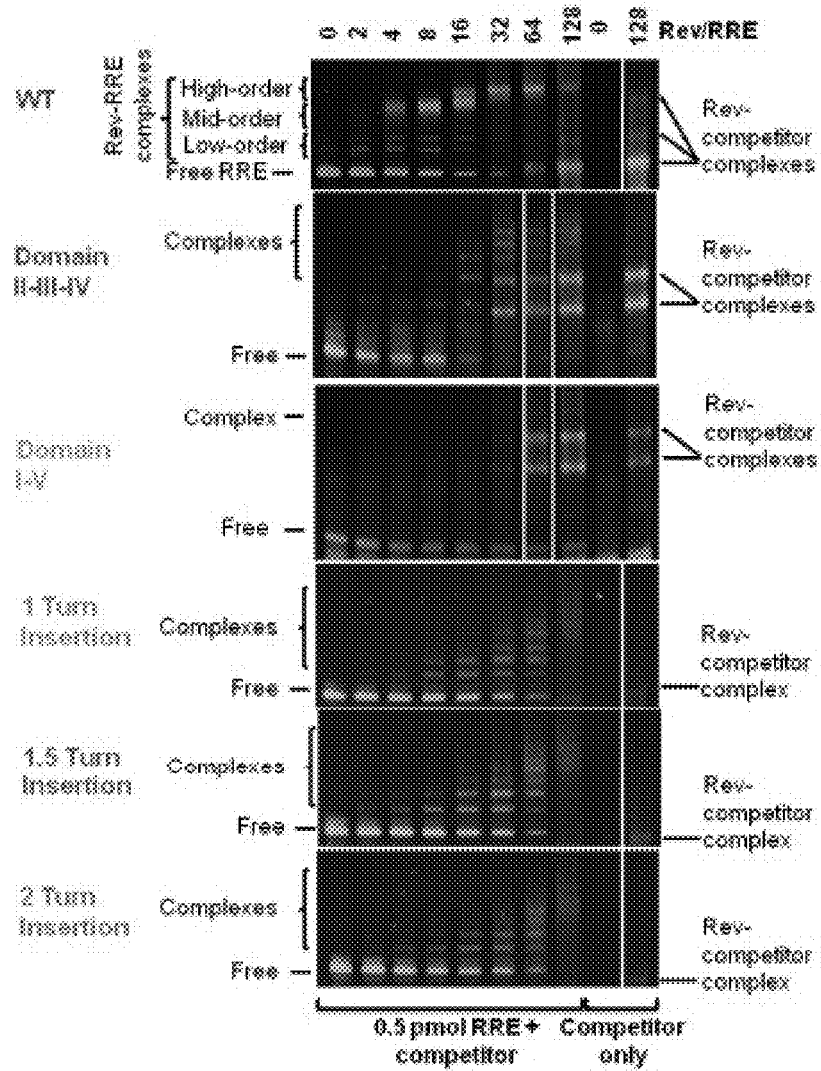
Figure 8B:
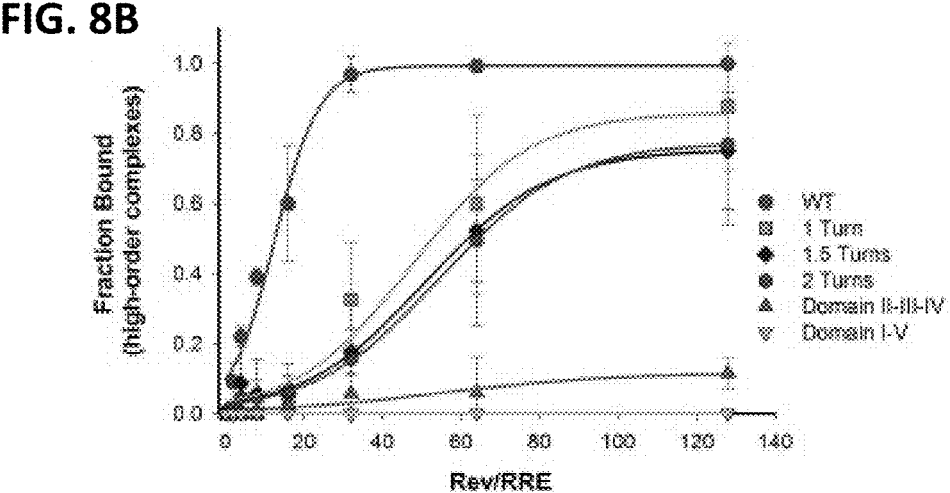
Figure 8C:
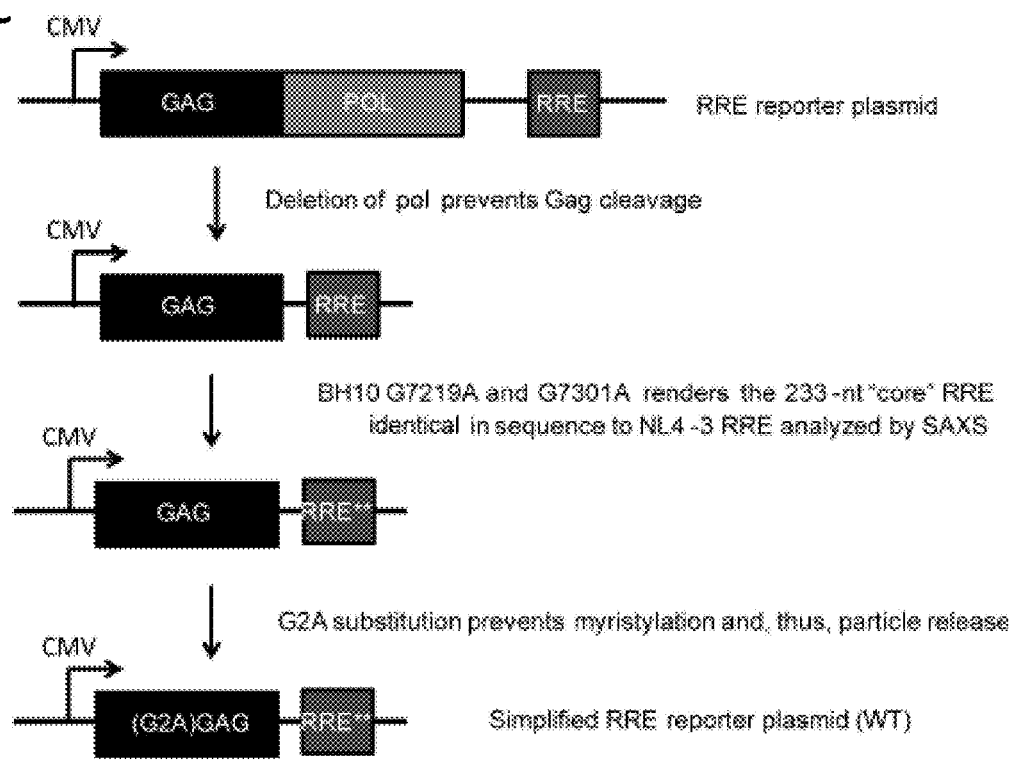
Figure 8D:
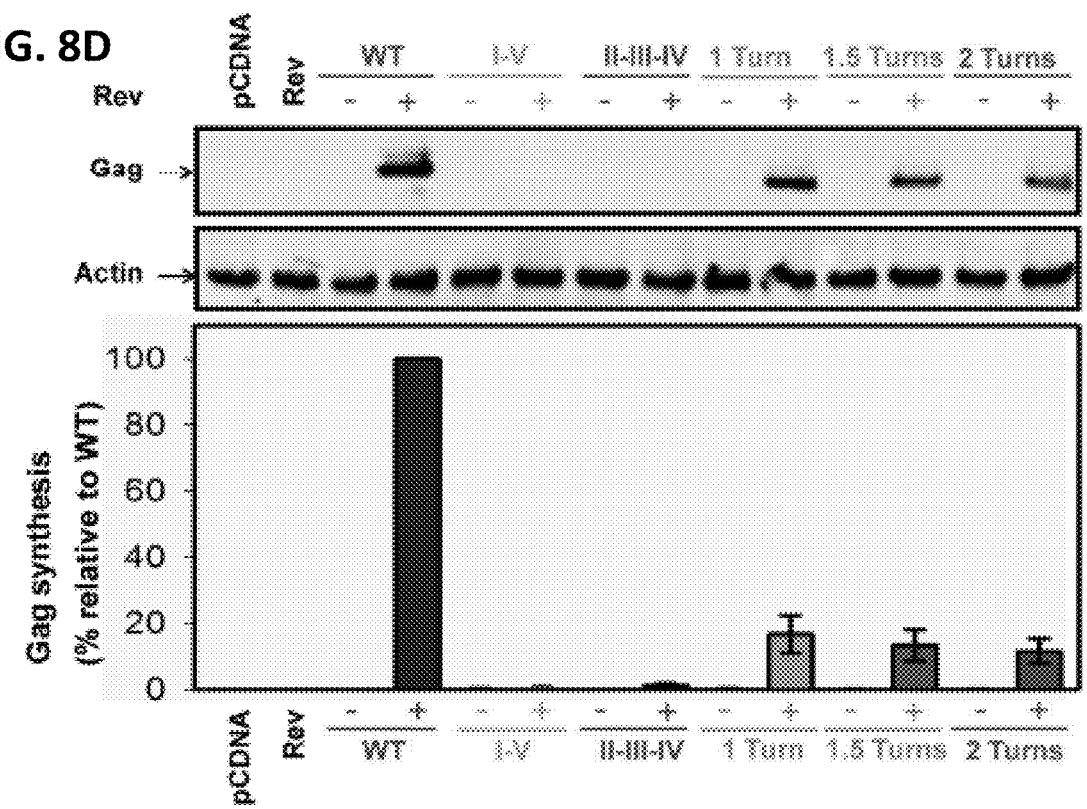

FIGS. 8A-8D are a series of panels showing Rev-RRE electrophoretic mobility shift assays (EMSA) and functional studies. FIG. 8A shows EMSA assays. Rev-binding reactions were loaded onto 6% or 10% non-denaturing TBE gels depending on the size of the RRE mutant (Domain II-III-IV: 119 nt; Domain I-V: 108 nt; 1 Turn: 253 nt; 1.5 Turn: 263 nt; 2 Turn: 273 nt). The first 8 lanes contain 0.5 pmol RRE, non-specific competitor RNA (RiboA) at 20-fold mass excess, and titrating amounts of Rev at the molar ratio indicated above each lane. The last two lanes contain only competitor RNA, either in the absence of Rev or with Rev added to the same level as in the highest Rev:RRE stoichiometry. White lines indicate cropping of irrelevant lanes. FIG. 8B shows fractions of wild type (WT), truncated, or mutant RRE RNAs engaged in high-order complexes plotted as a function of Rev:RRE molar ratio. Data from three independent EMSA experiments are shown as mean±standard deviation. FIG. 8C illustrates modification of plasmid pCMVgagpol-RRE (Srinivasakumar et al., *J Virol* 71:5841-5848, 1997) to simplify the RRE reporter assay. First, the pol gene was deleted; removal of the protease domain within pol prevents Gag cleavage, thus confining Gag to one band on a Western blot. Second, the 233-nt "core" RRE was rendered identical in sequence to the NL4.3 RRE analyzed by SAXS. Third, the N-terminal glycine codon of gag was replaced by an alanine codon, preventing Gag myristylation, and thus, virion release. FIG. 8D shows Western analysis of cell lysates using anti-p24$^{CA}$ and anti-β-actin antibodies. Top panel: pcDNA: cells transfected with neither pCMVRev nor reporter plasmid; Rev, cells transfected with pCMVRev alone; and remaining lanes contain reporter plasmids as indicated. WT: wild-type RRE; I-V: domains I-V (domains II-III-IV have been deleted); II-III-IV: domains II-III-IV (domains I-V have been deleted); 1 Turn, 1.5 Turns, and 2 Turns: insertion mutants with one, one and a half, and two turns of a duplex, respectively. Bottom panel: Quantification of the Western analysis. Gag synthesis relative to WT (set at 100%): Gag levels were normalized to actin levels and to transfection efficiency, as measured by Gaussia Luciferase assays. Gag synthesis is shown as the mean±standard deviation from 3-5 independent transfections.

Figure 9:
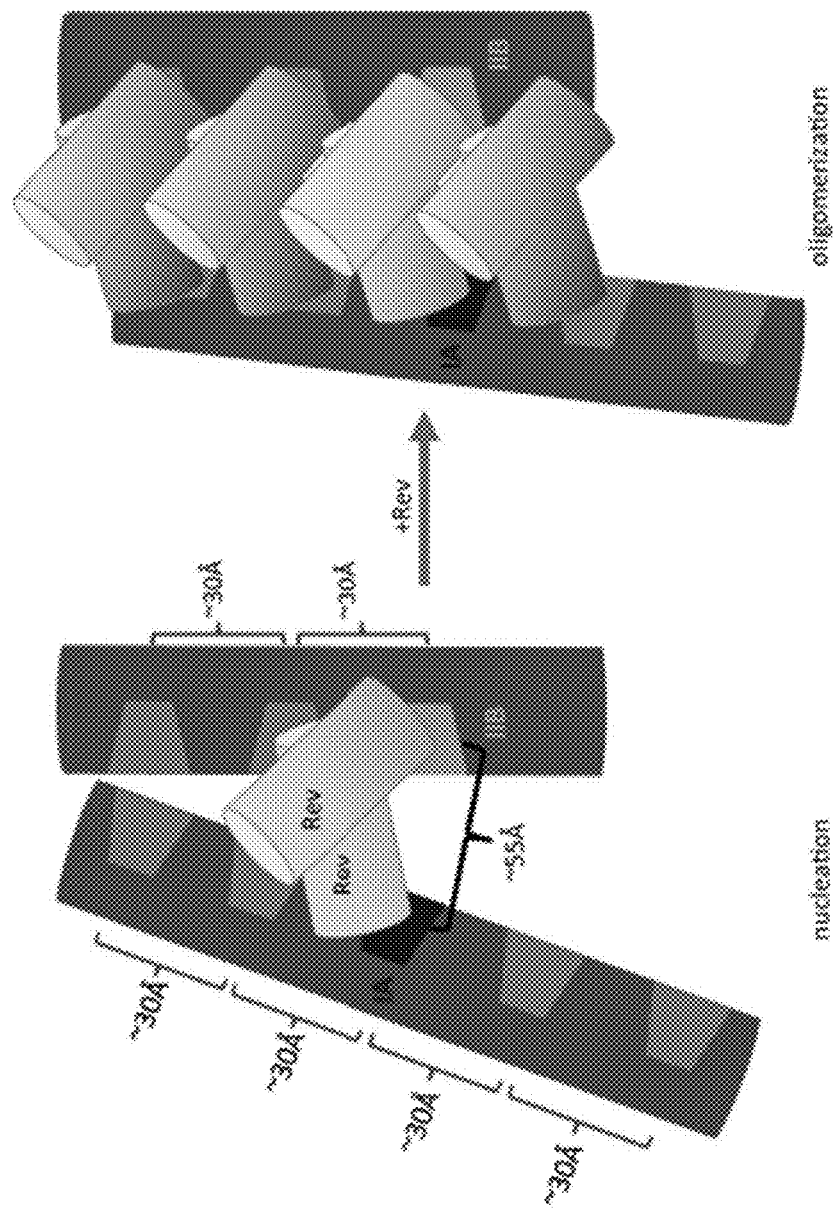

FIG. 9 shows models for initial Rev binding and Rev oligomerization on the RRE RNA. The RRE RNA is depicted as cylinders with the IIB and IA Rev binding sites indicated, and other major grooves shown (unlabeled). Initial binding of the first two Rev molecules (depicted in light color cylinders) to the IIB and IA sites results in a nucleation site (left) for subsequent Rev oligomerization on the RRE RNA (right). This oligomerization is partially driven by hydrophobic interactions between the two Rev dimers and is constrained by the major groove spacing and the topological arrangement of the two major segments of the RRE. This oligomerization model illustrates the maximum number of Rev molecules that could potentially bind to this 233-nt RRE molecule based on spatial constraints.

Figure 3:
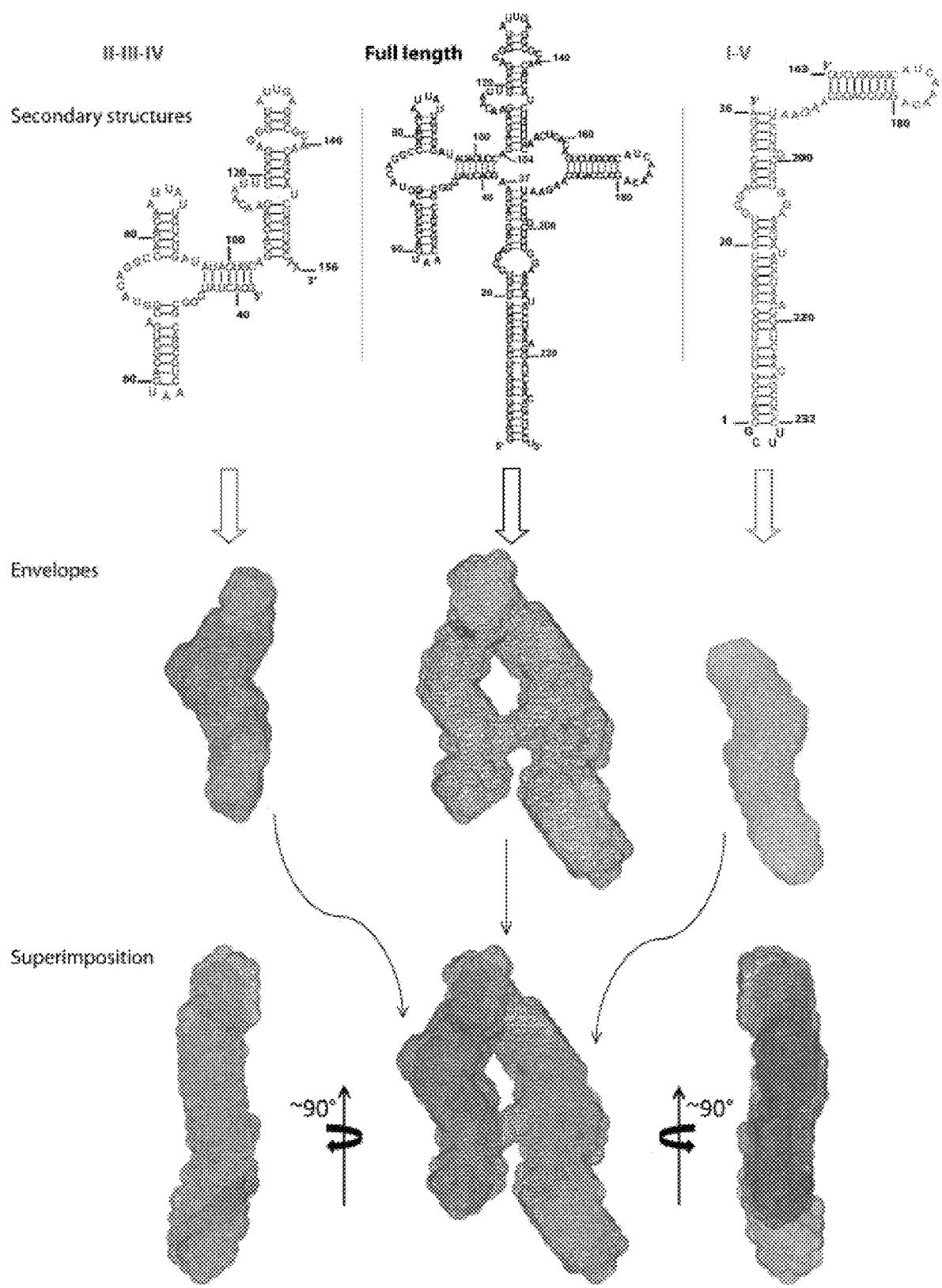
FIG. 3 is a series of panels showing the identification of the RRE domain locations. The top and middle panels are respectively the secondary structures and envelopes of the domain constructs (domains II, III and IV (left, SEQ ID NO: 31); domains I and V (right, SEQ ID NO: 32)) and the full length RRE (center, SEQ ID NO: 30). The bottom panel shows three views of superimposition of the envelopes.
Figure 10:
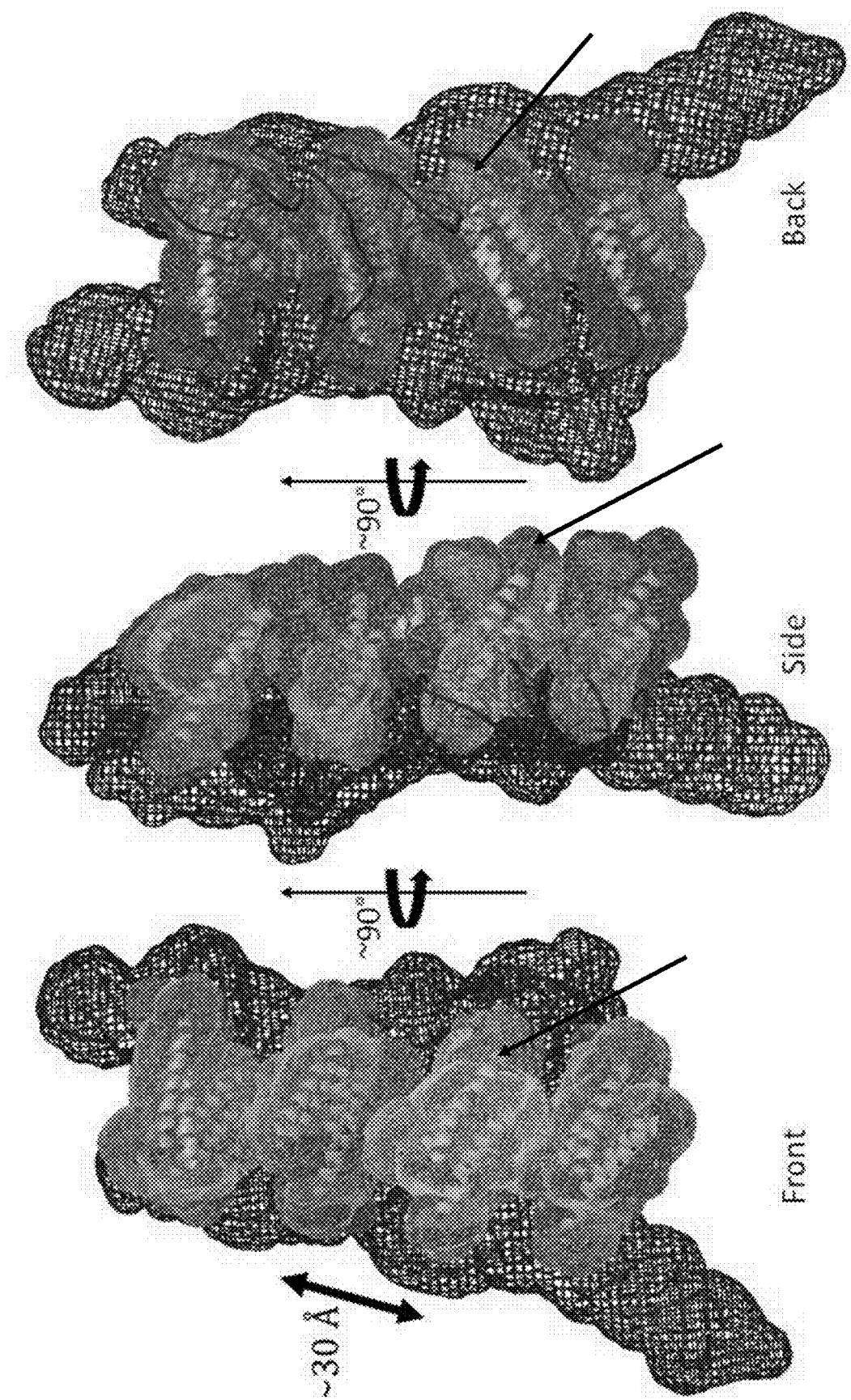

FIG. 10 shows three views of the proposed model for Rev oligomerization. The total number of Rev molecules in the model is somewhat arbitrary. The initial binding of two Rev molecules (arrow) to the IIB and IA sites results in nucleation, followed by oligomerization of additional Rev molecules (light gray) along the two major structural elements of RRE (ribbon diagram under mesh), driven by interactions between ARMs and major grooves as well as hydrophobic contacts between Rev monomers. Both the RRE and Rev dimer interfaces most likely undergo slight conformational changes in order to accommodate additional Rev binding for oligomerization (e.g., the RRE could change from an A-shaped to an H-shaped molecule as Rev molecules bind). The contact interfaces between IIB and Rev monomer 1, and between IA and Rev monomer 2, are modeled using data from the literature (Daugherty et al., *Mol Cell* 31:824-834, 2008) and the rest of the Rev molecules were added to the RRE so that the ARMs of these Rev molecules insert into major grooves on both domains II-III-IV and I-V. As a result, the Rev dimers bridge domains II-III-IV and I-V. The Rev dimers from a crystal structure (PDB Accession No. 3LPH) and the putative RRE structure (FIG. 3) were used for this modeling without any changes. This oligomerization model illustrates the maximum number of Rev molecules that could potentially bind to this 233-nt RRE molecule based on spatial constraints. The distance between the Rev dimers is approximately 30 Å, roughly the distance between two adjacent major grooves of an RNA helix.

Figure 11:
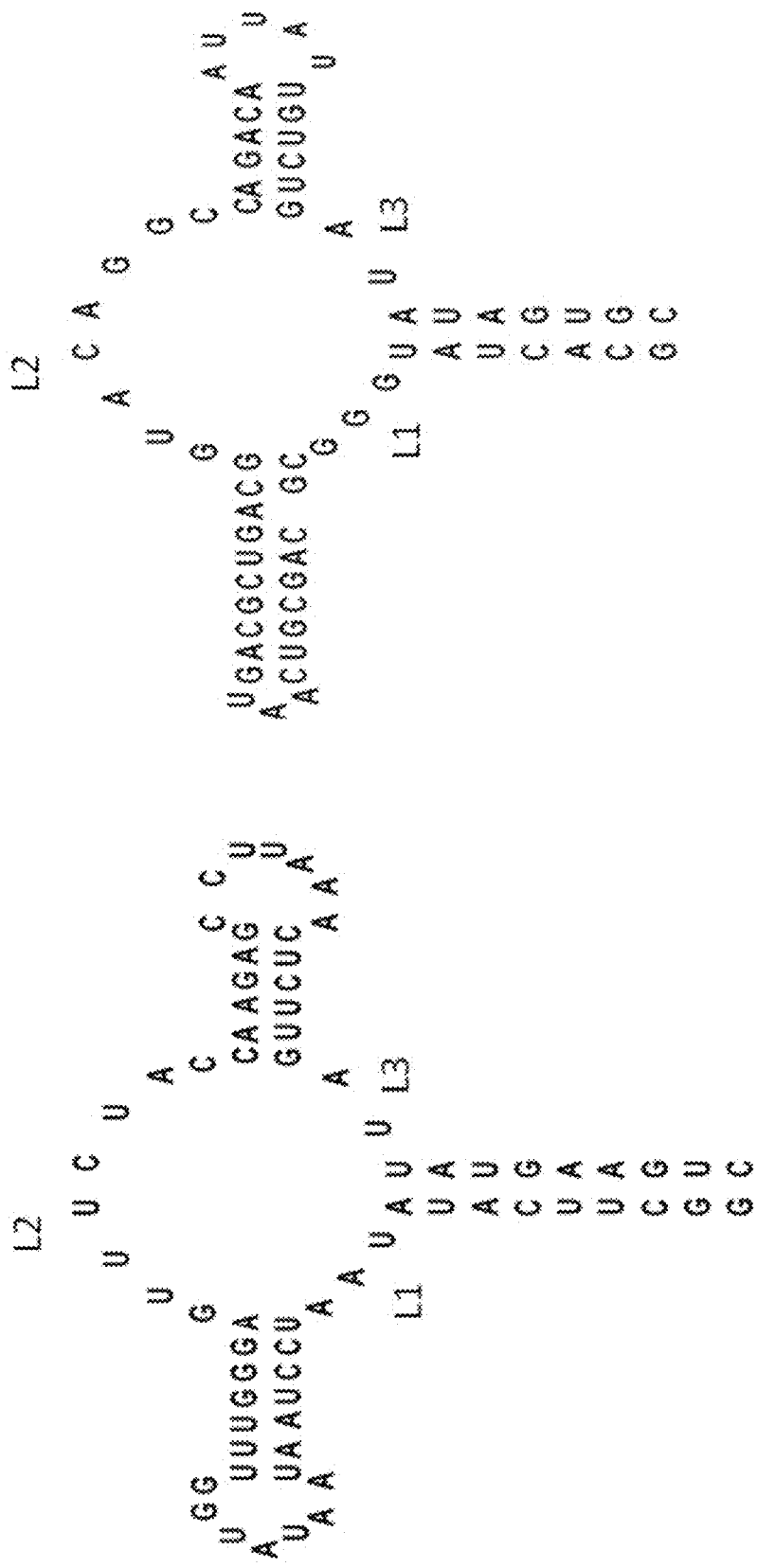

FIG. 11 shows similarities between the two secondary structures of RRE Domain II and the adenine riboswitch (Serganov et al., *Chem and Bio* 11:1729-1741, 2004). The secondary structures of the adenine riboswitch (SEQ ID NO: 38; left) (Serganov et al., *Chem and Bio* 11:1729-1741, 2004) and domain II (SEQ ID NO: 39; right) share some key characteristics, such as identical numbers of residues in respective linkers L1, L2 and L3, and types of residues in these linkers.

Figure 12:
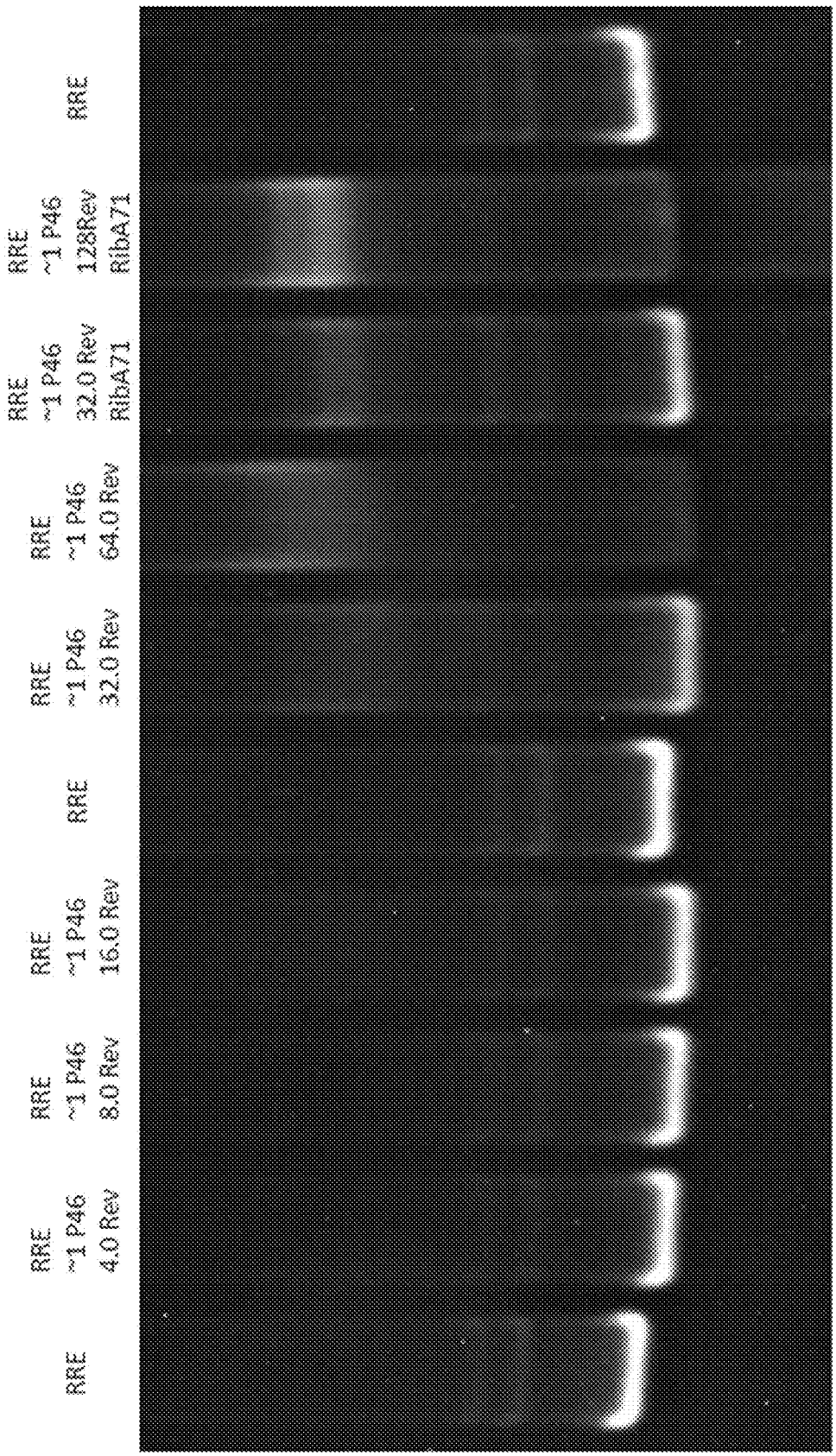

FIG. 12 is a digital image showing EMSA of peptide P46 competitive binding to RRE in presence of excess amount of the HIV-1 Rev protein on a 6% nondenaturing TBE gel with 1 mM Mg$^{2+}$. Even at 1:16 RRE:Rev, peptide P46 almost completely blocks the binding of Rev to RRE as reflected in the lack of shift (RRE:Rev complex). RibA71 is a riboswitch RNA and was included in some cases in a 100-fold excess.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 25, 2019, and is ~12 kilobytes, which is incorporated by reference herein.

SEQ ID NOs: 1-20 are amino acid sequences of exemplary Rev response element binding peptides.

SEQ ID NOs: 21-27 are nucleic acid sequences of insertions in RRE mutant subconstructs.

SEQ ID NOs: 28 and 29 are nucleic acid sequences of RRE forward and reverse primers, respectively.

SEQ ID NO: 30 is the nucleic acid sequence of an exemplary RRE.

SEQ ID NO: 31 is the nucleic acid sequence of an RRE domain II-III-IV subconstruct.

SEQ ID NO: 32 is the nucleic acid sequence of an RRE domain I-V subconstruct.

SEQ ID NO: 33 is the nucleic acid sequence of an RRE domain II-III-IV-X subconstruct.

SEQ ID NO: 34 is the nucleic acid sequence of an RRE domain II-III-IV-C subconstruct SEQ ID NO: 35 is the nucleic acid sequence of an RRE 1-turn insertion construct.

SEQ ID NO: 36 is the nucleic acid sequence of an RRE 1.5-turn insertion construct.

SEQ ID NO: 37 is the nucleic acid sequence of an RRE 2-turn insertion construct.

SEQ ID NO: 38 is the nucleic acid sequence of an adenine riboswitch.

SEQ ID NO: 39 is the nucleic acid sequence of an RRE domain II.

DETAILED DESCRIPTION

I. Terms

Unless otherwise noted, technical terms are used according to conventional usage. Definitions of common terms in molecular biology may be found in Benjamin Lewin, Genes VII, published by Oxford University Press, 2000 (ISBN 019879276X); Kendrew et al. (eds.), The Encyclopedia of Molecular Biology, published by Blackwell Publishers, 1994 (ISBN 0632021829); Robert A. Meyers (ed.), Molecular Biology and Biotechnology: a Comprehensive Desk Reference, published by Wiley, John & Sons, Inc., 1995 (ISBN 0471186341); and George P. Rédei, Encyclopedic Dictionary of Genetics, Genomics, and Proteomics, 2nd Edition, 2003 (ISBN: 0-471-26821-6).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. All sequences associated with the GenBank Accession Nos. mentioned herein are incorporated by reference in their entirety as were present on Jan. 16, 2014, to the extent permissible by applicable rules and/or law. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administering: To provide or give a subject an agent, such as a compound, a prodrug of a compound, or a pharmaceutical composition as described herein, by any effective route. Exemplary routes of administration include, but are not limited to, injection (such as subcutaneous, intramuscular, intradermal, intraperitoneal, and intravenous), oral, sublingual, rectal, transdermal, and intranasal routes.

Arginine-rich motif (or arginine-rich sequence): An amino acid sequence that is densely populated with arginine and/or lysine residues. In some examples, the motif is about 8-20 amino acids in length and is particularly rich in arginine residues. Positively charged amino acid side chains are involved in binding of many proteins to nucleic acids (such as RNA), by contributing to recognition of the major groove of RNA. Arginine-rich motifs are described, for example, in Tan and Frankel, Proc. Natl. Acad. Sci. USA 92:5282-5286, 1995 and Weiss and Narayana, Biopolymers 48:167-180, 1998, both of which are incorporated by reference herein. Exemplary peptides including arginine-rich motifs are also disclosed herein, such as SEQ ID NOs: 1-20.

Cargo moiety: A molecule (such as a peptide or other molecule) that can function to significantly reduce or inhibit the growth of a cell, or even kill a cell (for example, by inducing apoptosis). In some examples, the cargo moiety can inhibit the growth of or kill a cell containing HIV (such as a cell containing HIV). Exemplary cargo moieties include radioisotopes, free radical generators, nucleic acid crosslinking agents, and toxins, such as bacterial, plant, or animal toxins. Additional cargo moieties include molecules that trigger cell death by apoptotic or non-apoptotic pathways.

Contacting: Placement in direct physical association, including both a solid and liquid form. Contacting can occur in vitro or ex vivo, for example with isolated cells or tissue, or in vivo by administering to a subject.

Control: A "control" refers to a sample or standard used for comparison with an experimental sample. In some embodiments, the control is a sample that is not contacted with a compound disclosed herein or a subject that is not treated with a compound disclosed herein. In some embodiments, the control is a historical control or standard reference value or range of values (such as a previously tested control sample or group of samples, or a control subject or group of subjects).

Detectable label: A compound or composition that is conjugated directly or indirectly to another molecule (such as an HIV RRE binding compound disclosed herein) to facilitate detection of that molecule. Specific, non-limiting examples of detectable labels include fluorescent and fluorogenic moieties, chemiluminescent molecules, chromogenic moieties, haptens, affinity tags, and radioactive isotopes. The label can be directly detectable (e.g., optically detectable) or indirectly detectable (for example, via interaction with one or more additional molecules that are in turn detectable).

Free radical generator: A compound that produces free radicals. Free radicals are chemically reactive species which possesses one or more single unpaired electrons. Free radicals include reactive oxygen species and reactive nitrogen species. In some examples, the free radical generator produces a reactive oxygen species, such as a hydroxyl radical (*OH).

Inhibiting, treating, or preventing a disease: Inhibiting the full development of a disease or condition, for example, in a subject who is at risk for a disease such as acquired immune deficiency syndrome (AIDS), AIDS related conditions (such as AIDS related complex; ARC), HIV infection (such as HIV-1 infection), or combinations thereof. "Treatment" refers to a therapeutic intervention that ameliorates a sign or symptom of a disease (such as AIDS or AIDS related conditions) after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. Preventing a disease means inhibiting development of a disease in a subject who would normally be expected to develop the disease or be at increased risk for the disease.

Isolated: An "isolated" biological component (such as a protein, for example a disclosed polypeptide or nucleic acid encoding such a polypeptide) has been substantially separated or purified away from other biological components in which the component occurs, such as other chromosomal and extrachromosomal DNA, RNA, and proteins. Proteins, peptides, and nucleic acids that have been "isolated" include proteins or nucleic acids purified by standard purification methods. The term also embraces proteins or peptides prepared by recombinant expression in a host cell as well as chemically synthesized proteins, peptides, and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Linking, joining, or conjugating: Coupling a first moiety to a second moiety. This includes, but is not limited to, covalently bonding one moiety to another moiety (for example, directly or via a linker molecule), non-covalently joining one moiety to another (e.g. by electrostatic bonding, hydrogen bonding, or van der Waals forces), and any and all combinations of such couplings Linker or spacer: A molecule that joins together (for example, covalently joins) two or more moieties but does not have specific biological activity and does not significantly negatively affect the activity or the function of the moieties. The linker preferably is bio-compatible. The linker can be selected to provide or affect a property of the joined moieties, for example, folding, conformation, hydrophobicity, and/or spacing of the moieties. In some examples, the linker includes reactive sites at each end that each can form a covalent bond with one of the moieties included in the compounds described herein. In some examples, a linker includes a peptide, a straight or branched chain carbon linker, or a heterocyclic carbon linker.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the proteins, nucleic acids, and other compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions, powder, pill, tablet, or capsule forms, conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide or peptide: Any compound composed of amino acids, amino acid analogs, chemically bound together. "Polypeptide" or "peptide," as used herein, includes oligomers of amino acids, amino acid analog, or small and large peptides, including proteins. Any chain of amino acids, regardless of length or post-translational modification (such as glycosylation or phosphorylation) is referred to as a polypeptide or peptide. The term polypeptide applies to amino acid polymers including naturally occurring amino acid polymers and non-naturally occurring amino acid polymers as well as polymers in which one or more amino acid residue is a non-natural amino acid, for example an artificial chemical mimetic of a corresponding naturally occurring amino acid.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

Rev: An HIV gene encoding the "regulator of expression of virion proteins." The Rev protein binds to an element in the env-coding region of HIV RNA, known as the Rev response element (RRE). The Rev-RRE complex mediates transport of unspliced or singly spliced HIV RNAs through the nuclear pore complex from the nucleus to the cytoplasm. The RRE includes stems I, II, III/IV, and V, arranged around a central four-way junction, with stem-loop II split into a proximal stem (IIA) and distal stem-loops (IIB and IIC) around a three-way junction (Legiewicz et al., *Proc. Natl. Acad. Sci. USA* 105:14365-14370, 2008).

Rev protein and nucleic acid sequences are publicly available. Exemplary Rev amino acid sequences include GenBank Accession Nos. NP_057854, AAC82592, and Q77YF8, and exemplary Rev nucleic acid sequences include GenBank Accession Nos. NC_001802 and AF033819, all of which are incorporated by reference herein as present in GenBank on Jan. 16, 2014. Exemplary RRE nucleic acid sequences include nucleotides 7760-7792 of GenBank Accession No. AF324493, nucleotides 1534-1766 of GenBank Accession No. AY426103, and GenBank Accession Nos. FJ649330 and FJ649326, all of which are incorporated by reference herein as present in GenBank on Jan. 16, 2014.

Small organic molecule: An organic molecule with a molecular weight of about 1000 daltons or less (for example about 900 daltons or less, about 800 daltons or less, about 700 daltons or less, about 600 daltons or less, about 500 daltons or less, about 400 daltons or less, about 300 daltons or less, about 200 daltons or less, or about 100 daltons or less). In some examples, a small organic molecule has a molecular weight of about 100-1000 daltons, about 200-900 daltons, about 300-700 daltons, about 200-500 daltons, or about 400-700 daltons.

Subject: Living multi-cellular vertebrate organisms, a category that includes both human and non-human mammals (including non-human primates).

Therapeutically effective amount or Effective amount: The amount of agent, such as nucleic acid, polypeptide, or other therapeutic agent, that is sufficient to prevent, treat (including prophylaxis), reduce and/or ameliorate the symptoms and/or underlying causes of any of a disorder or disease, for example to prevent, inhibit, and/or treat HIV infection. In some embodiments, an "effective amount" is sufficient to reduce or eliminate a symptom of a disease, such as AIDS or ARC. For instance, this can be the amount necessary to inhibit viral replication or to measurably alter outward symptoms of the viral infection, such as increase of T cell counts in the case of an HIV infection. In general, this amount will be sufficient to measurably inhibit virus (for example, HIV) replication or infectivity. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

II. Inhibitors of Rev Binding to RRE

Disclosed herein is the three-dimensional topological structure of the HIV RRE RNA. This RNA folds into an unusual structure that serves as a "molecular beacon" for viral recognition. The RRE structure identified by the inventors and disclosed herein revealed two Rev binding sites and their spatial arrangement and made it possible to design compounds that simultaneously bind to the two binding sites of the RRE RNA with high affinity and specificity and inhibit binding of Rev to the RRE RNA. The RRE is located in the reading frame coding for the Env protein. Thus, as disclosed in some examples herein, simultaneous disruption of the Rev-RRE interaction and destroying the RRE RNA may represent an extremely specific method of treating or inhibiting HIV infection, potentially even eliminating HIV from an infected individual. In addition, the unique structure of the HIV-1 RRE described herein provides for compounds that permit detection of HIV infection with extremely high sensitivity and specificity, even at very early time points in the infection.

In some embodiments, the compound that binds to RRE RNA includes two moieties, each of which bind to one of the Rev RRE binding sites. The two moieties are linked (for example covalently linked) together. The linkage between the moieties is selected to provide a spacing of about 30-80 Å (such as about 30-75, about 40-70, about 50-65, or about 50-60 Å). In some examples, the spacing between the two moieties is about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 Å. In some examples, the spacing between the two moieties is provided by a linker (for example, one or more of the linkers discussed below). In other examples, the spacing between the two moieties results from the flexibility of the two moieties that allows for binding to the Rev RRE binding sites with high affinity and/or specificity.

Without being bound by theory, it is believed that this spacing allows the high affinity binding of the two moieties to the RRE Rev binding sites. In some examples, the compound binds to at least one RRE Rev binding site with an affinity of about 1 mM to about 1 fM (such as about 100 µM to about 1 pM, about 10 µM to about 100 pM, about 1 µM to about 10 pM). In other examples, the compound binds to at least one RRE Rev binding site with an affinity of at least about 1 mM, at least about 100 µM, at least about 10 µM, at least about 1 µM, at least about 100 nM, at least about 10 nM, at least about 1 nM, at least about 100 pM, at least about 10 pM, at least about 1 pM, at least about 100 fM, at least about 10 fM, or at least about 1 fM. In some examples, one of the moieties binds to one of the Rev RRE binding sites with a high affinity (for example nM affinity) while the other binds to one of the Rev RRE binding sites with a lower affinity (for example, µM affinity). The combination of binding of these two moieties provides very high affinity binding (such as fM affinity) and/or very high specificity binding to the RRE RNA.

In some embodiments, the compounds include two moieties, each of which is a peptide or peptide mimetic that binds to a Rev binding site in the RRE RNA. In some examples, the peptides include L-amino acids and/or D-amino acids. In some examples, the peptides include an inverso-peptide (a peptide composed of D-amino acids having the same sequence but a mirror confirmation of a peptide of interest), a retro-peptide (a peptide composed of L-amino acids in the reverse order from the peptide of interest), or a retro-inverso peptide (a peptide composed of D-amino acids in the reverse order from the peptide of interest). In other examples, the peptides may be stabilized peptides, such as peptides including one or more non-standard amino acids (such as ornithine, homolysine, norleucine, or norvaline, or D-amino acids, as discussed above), peptides with chemically modified N- and/or C-termini (such as modification by acetylation and/or amidation), or stapled peptides (see, e.g., U.S. Pat. No. 7,723,469, incorporated by reference herein). In additional examples, peptides (such as alpha-helical peptides) are stabilized by adding one or more (for example, 1, 2, 3, 4, 5, or more) hydrophobic residues at the end of the peptide. The two moieties may each be the same peptide, or in some examples are each a different peptide. In some examples, the peptides include an arginine-rich motif.

Exemplary peptides include or consist of the following (shown in N-terminal to C-terminal orientation):

```
                            (SEQ ID NO: 1)
TRQARRNRRRRWRERQRAAAA (SEQ ID NO: 2)
RRRDRRLRQRARRRAAAA (SEQ ID NO: 3)
TRQARRNRRRRWRERQRCAAAA (SEQ ID NO: 4)
TRQARRNRRRRWRECQRAAAAR (SEQ ID NO: 5)
TRQARRNRRRRWREKQRAAAAR (SEQ ID NO: 6)
TRQARRNRRRRWRERQRAAAAR (SEQ ID NO: 7)
DTRQARRNRRRRWRECQRAAAAR (SEQ ID NO: 8)
RRRDRRLRQRARRRAAAAR (SEQ ID NO: 9)
RRRDRRLRQRARRRAAAAG (SEQ ID NO: 10)
TRQARRNRRRRWRERQRAAAAG (SEQ ID NO: 11)
AAAARQRERWRRRNRRAQRT (SEQ ID NO: 12)
AAAARRRARQRLRRDRRR (SEQ ID NO: 13)
AAAACRQRERWRRRNRRAQRT (SEQ ID NO: 14)
RAAAARQCERWRRRRNRRAQRT (SEQ ID NO: 15)
RAAAARQKERWRRRRNRRAQRT (SEQ ID NO: 16)
RAAAARQRERWRRRRNRRAQRT (SEQ ID NO: 17)
RAAAARQCERWRRRRNRRAQRTD (SEQ ID NO: 18)
RAAAARRRARQRLRRDRRR (SEQ ID NO: 19)
GAAAARRRARQRLRRDRRR (SEQ ID NO: 20)
GAAAARQRERWRRRRNRRAQRT
```

In some examples, the peptides include or consist of any one of SEQ ID NOs: 1-20. In other examples, the peptides include or consist of at least 14-22 residues of SEQ ID NOs: 1-20. In particular examples, one to five of the C-terminal residues of SEQ ID NOs: 1-10 or one to five of the N-terminal residues of SEQ ID NOs: 11-20 are removed. In still further examples, the peptides are at least 90% identical to the amino acid sequence of SEQ ID NOs: 1-20 (such as at least 91%, at least 92%, at least 93%, at least 94%, at least 95%, at least 96%, at least 97%, at least 98%, at least 99%, or even 100% identical). In some specific examples, the peptides of SEQ ID NOs: 1-20 are synthesized as inverso peptides, retro peptides, or retro-inverso peptides. Without being bound by theory, it is believed that these modified versions of the peptides may enhance their cellular stability (including, but not limited to, having increased resistance to proteolytic degradation).

In some embodiments, two ARM containing peptides (such as SEQ ID NOs: 1-20) are linked or joined to produce an RRE binding compound of the disclosure. Methods of linking peptides are known to one of skill in the art and include direct or indirect covalent linkage. In some examples, the linkage is a direct linkage between the peptides, such as through a sulfhydryl group, a primary amine, a carboxyl group, or a carbonyl group. In some examples, the linkage is via a disulfide bond, an amide bond, or a thioester bond. In still further examples, the linkage is via a crosslinker, for example, a crosslinker including a spacer arm providing the desired spacing or distance between the two peptides (such as about 30-80 Å, as discussed above). In particular examples, the linker can comprise or consist of a lysine, aspartic acid, glutamic acid, or succinic acid, which contain bipartite groups.

Crosslinking reagents that can be used to join the two peptides include those with amine-reactive groups (such as N-hydroxysuccinimide esters or imidoesters), carboxylic acid-reactive groups (such as carbodiimides), sulfhydryl-reactive groups (such as maleimides, haloacetyls, or pyridyl disulfides), and carbonyl-reactive groups (such as hydrazides, alkoxyamines, or reductive amination with sodium cyanoborohydride). In some examples, the crosslinking reagent utilizes a reactive group present in the peptide. In other examples, the peptide is modified to introduce the desired reactive group(s) (for example, oxidation to introduce one or more aldehyde groups) prior to crosslinking.

Crosslinking reagents may include a spacer that is included in the linkage between the two linked moieties. In some examples, the crosslinking reagent is homobifunctional (having identical reactive groups at either end of a spacer) and in other examples, the crosslinking reagent is heterobifunctional (having different reactive groups at either end of a spacer). A spacer of a desired length can be selected. In some examples, the spacer arm includes a peptide, a hydrocarbon chain or a heterocyclic carbon chain. The length of the spacer arm is determined by the length of the peptide, the hydrocarbon chain, or heterocyclic carbon chain. In one example, the spacer includes one or more polyethylene glycol (PEG) subunits. The number of PEG subunits is selected to obtain a spacer of the desired length. For example, a spacer including 12 PEG subunits ($PEG_{12}$) is about 45-50 Å in length.

In some embodiments, each of the two moieties in the compound are the same, while in other examples, the two moieties are different. In several, non-limiting embodiments, the RRE binder includes the following:

(a) Linkage of two peptides each comprising the amino acid sequence of SEQ ID NO: 1 between the carboxyl termini using a dual carboxyl reactive cross linker:

TRQARRNRRRRWRERQRAAAA-LINKER-AAAARQRERWRRRRNRRAQRT (b) Linkage of two peptides each comprising the amino acid sequence of SEQ ID NO: 2 between the carboxyl termini using a dual carboxyl reactive cross linker:

RRRDRRLRQRARRRAAAA-LINKER-AAAARRRARQRLRRDRRR

In particular embodiments of the previous two examples, the linker can include or consist of a lysine residue.

(c) Linkage of two peptides each comprising the amino acid sequence of SEQ ID NO: 3, via a disulfide bond:

TRQARRNRRRRWRERQRCAAAA
|
AAAACRQRERWRRRRNRRAQRT (d) Linkage of two peptides each comprising the amino acid sequence of SEQ ID NO: 4, via a disulfide bond:

TRQARRNRRRRWRECQRAAAAR
|
RAAAARQCERWRRRRNRRAQRT (e) Linkage of two peptides each comprising the amino acid sequence of SEQ ID NO: 5, via a lysine-glutamic acid linkage:

TRQARRNRRRRWREKQRAAAAR
|
RAAAARQEERWRRRRNRRAQRT (f) Linkage of two peptides, one comprising the amino acid sequence of SEQ ID NO: 9, and one comprising the amino acid sequence of SEQ ID NO: 19:
RRRDRRLRQRARRRAAAAG-LINKER-GAAAARR-RARQRLRRDRRR (g) Linkage of two peptides, one comprising the amino acid sequence of SEQ ID NO: 9, and one comprising the amino acid sequence of SEQ ID NO: 20:
RRRDRRLRQRARRRAAAAG-LINKER-GAAAARQR-ERWRRRRNRRAQRT In particular embodiments of the two previous examples, the linker can include or consist of succinic acid or succinate.

Additional exemplary compounds include linkage of two peptides each comprising the amino acid sequence of any one of SEQ ID NOs: 1-20. Further examples include linkage of SEQ ID NO: 1 and SEQ ID NO: 2, SEQ ID NO: 3 and SEQ ID NO: 4, SEQ ID NO: 5 and SEQ ID NO: 6, and so on. Other combinations include SEQ ID NO: 1 and SEQ ID NO: 11, SEQ ID NO: 2 and SEQ ID NO: 12, SEQ ID NO: 3 and SEQ ID NO: 13, and so on. These combinations are only examples, and are non-limiting.

In additional examples, the two moieties included in the compound are not peptides. The moieties can be, for example, small molecules (such as small organic molecules) that are capable of binding RNA, such as a Rev binding site of a RRE, and that can be linked or joined with the appropriate spacing (such as about 30-80 Å, about 40-70 Å, about 40-65 Å, about 50-65 Å, or about 50-60 Å). The two moieties may each be the same small molecule, or in some examples may each be a different small molecule. Exemplary small molecules (for example, small organic molecules) that can bind RRE RNA, include aminoglycoside antibiotics. In some examples, the small molecule includes aminoglycoside antibiotics neomycin B, tobramycin, or lividomicin A. Additional small molecules that bind to RRE and/or inhibit Rev binding to RRE include heterocyclic compounds (e.g., Shuck-Lee, et al., *Antimicrob Agents Chemother* 52:3169-3179, 2008; U.S. Pat. App. Publ. 2008/0318959, both of which are incorporated herein by reference in their entirety) and small molecules with an acidic moiety at the end of a linear aromatic system (e.g., Chapman et al., *Antiviral Res* 54:149-162, 2002, incorporated herein by reference in its entirety). RNA binding compounds are known to one of skill in the art and can be tested for their ability to bind RNA (such as RRE RNA) using the electrophoretic mobility shift assay (EMSA) described in Example 1, surface plasmon resonance, fluorescence anisotropy, or other methods known to one of skill in the art.

In still further examples, the compound includes one moiety that is a peptide (for example, one of SEQ ID NOs: 1-20) and one moiety that is not a peptide, for example an RNA binding small molecule (such as an aminoglycoside antibiotic). In particular examples, the compound includes a peptide comprising the amino acid sequence of one of SEQ ID NOs: 1-20 and neomycin B linked or joined with a spacing of about 30-80 Å.

Also disclosed herein are compounds that bind HIV RRE and/or inhibit Rev binding to RRE (such as those above) that further include a detectable label linked to the compound (for example, covalently linked to the compound). Detectable labels include radioisotopes (such as $^3$H, $^{35}$S, $^{32}$P, $^{14}$C, $^{125}$I, $^{11}$C, $^{15}$O, $^{13}$N, $^{18}$F, $^{76}$Br, $^{123}$I, $^{124}$I), fluorescent molecules (such as Cy3®, Cy5®, Alexa Fluor® dyes, rhodamine, fluorescein isothiocyanate), magnetic or paramagnetic labels (such as iron oxide nanoparticles), nanoparticles (such as gold or silver nanoparticles), enzymes (such as alkaline phosphatase or horseradish peroxidase), or haptens (such as biotin, digoxigenin, or fluorescein). One of ordinary skill in the art can select additional detectable labels for use in the compounds and methods described herein.

In some examples, linkage of the detectable label to the compound (for example by covalent or non-covalent linkage) is through crosslinkers and spacers as described above. In other examples, the detectable label is directly included in the compound itself, for example in the case of some radiolabels (such as $^3$H, $^{14}$C, $^{15}$O, or $^{13}$N). In further examples, the label may be attached (for example, covalently linked) to the RRE binder through the linkage between the two moieties of the compound. In other examples, the label may be incorporated in the RRE binder during synthesis of a peptide moiety or covalently incorporated into the peptide at specific residue(s) after peptide synthesis. Synthetic peptides may be covalently labeled by inclusion of an amine- or thiol-reactive detectable label. Similar strategies may be used to link a detectable label to a small organic molecule.

The detectable label is linked to the compound such that the activity of the compound (for example, binding to RRE and/or inhibiting Rev binding to RRE) is not substantially affected. In some examples, the linkage of the detectable label decreases binding affinity of the compound including the detectable label for RRE by no more than about 50% (for example, no more than about 40%, about 30%, about 20%, about 15%, about 10%, about 5%, or less) compared to the affinity of the compound not including the detectable label. In other examples, the linkage of the detectable label decreases inhibition of Rev binding to RRE by the compound including the detectable label by no more than about 50% (for example, no more than about 40%, about 30%, about 20%, about 15%, about 10%, about 5%, or less) compared to inhibition of Rev binding to RRE by the compound that does not include the detectable label.

Also disclosed herein are compounds that bind HIV RRE and/or inhibit Rev binding to RRE (such as those above) that further include a cargo moiety linked to the compound (for example, covalently linked to the compound). In some examples, the cargo moiety is a compound or molecule that can reduce or inhibit the growth of, or kill a cell containing HIV (such as a radioisotope, free radical generator, RNA cleavage agent, or RNA cross-linking agent, toxin, or apoptosis-promoting molecule). In particular examples, the cargo moiety includes a free radical generating moiety (such as a hydroxyl radical generating moiety). The free radical can cleave RNA. Without being bound by theory, it is believed that when the RRE binder is bound to the Rev binding site of an RRE, the free radicals (for example, hydroxyl radicals) generated can cleave viral RNA, thereby destroying the viral genome in the cell. In one particular example, the free radical generating moiety includes Fe(II)EDTA (see, e.g., Samaha et al., *Proc. Natl. Acad. Sci. USA* 96:366-370, 1999) or a metal oxide (see, e.g., U.S. Pat. App. Publ. 2010/0329971). Additional free radical (e.g., hydroxyl radical) generating agents include phosphonoformic acid-Fe$^3$ complex (see, e.g., Lindqvist and Nordstrom, *Pharmacol. Toxicol.* 89:49-55, 2001) and Cu(I) iodide particles (see, e.g., Fujimori et al., *Appl. Environ. Microbiol.* 78:951-955, 2011). One of ordinary skill in the art can identify additional free radical generators that can be used in the disclosed compositions and methods.

In other examples, the cargo moiety is a nucleic acid crosslinking agent, such as an RNA crosslinking agent. In some examples, the crosslinking agent includes 1,4-phenyl diglyoxal (see, e.g., Wagner and Garrett, *Nucl. Acids Res.* 5:4065-4075, 1978) or N-acetyl-N'-(p-glyoxylyl-benzoyl) cystamine (see, e.g., Expert-Bezancon et al., *Eur. J. Biochem.* 136:267-274, 1983). Additional nucleic acid crosslinkers are known to one of skill in the art. See, e.g., Harris and Christian, *Meth. Enzymol.* 468:127-146, 2009.

In further examples, the cargo moiety is a bacterial toxin, including but not limited to *Pseudomonas aeruginosa* exotoxin (e.g., GenBank Accession Nos. IIKP A, AAB59097.1, and AAF90003.1; see also U.S. Pat. No. 6,011,002), diphtheria toxin (e.g., GenBank Accession Nos. NP_938615 and YP_005132731), pertussis toxin, cholera toxin (e.g., GenBank Accession Nos. BAA06291.1, ACF35010.1, and BAA06288.1; as well as variant sequences provided in WO 2009/149281), heat-labile enterotoxin, or fragments or variants thereof. Additional bacterial toxins include pore-forming toxins, such as proaerolysin (e.g., GenBank Accession Nos. AAA21938.1 and P09167.2; see also, U.S. Pat. No. 7,282,476), aerolysin (e.g., GenBank Accession Nos. ABR14715.1 and ABR14714.1), or *Clostridium septicum* alpha toxin (e.g., GenBank Accession Nos. AAB32892, ADR70993, and ACA60985), or fragments or variants thereof. In other examples, the cargo moiety includes pro-apoptotic compounds or inhibitors of anti-apoptotic molecules. Exemplary pro-apoptotic compounds include apoptosis-promoting members of the Bcl-2 family, such as Bax (e.g., GenBank Accession Nos. CAE52909.1, AAO22992.1, and EAW52418.1), Bad (e.g., GenBank Accession Nos. CAG46757, AAH01901.1, and CAG46733.1; and sequences provided in U.S. Pat. No. 6,737,511), Bak (e.g., GenBank Accession Nos. NP_001179, XP_005249310, and XP_005249311), and Bik (e.g., GenBank Accession Nos. NP_001188, ABM92195, and EAW73283). Inhibitors of anti-apoptotic molecules include inhibitors or antagonists of anti-apoptotic members of the Bcl-2 family, such as inhibitors of Bcl-2, Bcl-XL, Bcl-w, Mcl-1, Bfl1/A-, and Bcl-B. Inhibitors of these anti-apoptotic members of the Bcl-2 family include gossypol (AT-101), apogossypol, HA-14, antimycin A, BH3Is, oblimersen sodium, ABT-737 (ABT-263), and GX15-080 (see, e.g., Kang and Reynolds, *Clin. Cancer Res.* 15:1126-1132, 2009). An additional cargo moiety includes granzyme B.

In some examples, linkage of the cargo moiety to the compound (for example by covalent or non-covalent linkage) is through crosslinkers and spacers as described above. In further examples, the cargo moiety may be attached (for example, covalently linked) to the RRE binder through the linkage between the two moieties of the compound. In other examples, the cargo moiety may be incorporated in the RRE binder during synthesis of a peptide moiety or covalently incorporated into the peptide at specific residue(s) after peptide synthesis. The cargo moiety may also be covalently linked to a peptide by inclusion of an amine- or thiol-reactive detectable label. Similar strategies may be used to link a cargo moiety to a small organic molecule.

The cargo moiety is linked to the compound such that the activity of the compound (for example, binding to RRE and/or inhibiting Rev binding to RRE) is not substantially affected. In some examples, the linkage of the cargo moiety decreases binding affinity of the compound including the cargo moiety for RRE by no more than about 50% (for example, no more than about 40%, about 30%, about 20%, about 15%, about 10%, about 5%, or less) compared to the affinity of the compound that does not include the cargo moiety. In other examples, the linkage of the cargo moiety decreases inhibition of Rev binding to RRE by the compound including the cargo moiety by no more than about 50% (for example, no more than about 40%, about 30%, about 20%, about 15%, about 10%, about 5%, or less) compared to inhibition of Rev binding to RRE by the compound not including the cargo moiety.

III. Methods of Inhibiting Rev Binding to RRE

Also disclosed herein are methods of inhibiting binding of Rev to a RRE RNA. The methods include contacting an RRE RNA with an inhibitor of Rev binding, such as one or more of the inhibitors disclosed herein. The methods can be in vitro or in vivo. For example, in some embodiments, the methods include contacting an isolated RRE RNA with an inhibitor compound, such as an RRE binding compound disclosed herein. In other examples, the methods include contacting a cell including an RRE RNA with the RRE binding compound (for example, in vitro or ex vivo), or even by administering the compound to a subject (such as a subject infected with HIV or suspected to be infected with HIV).

In some examples, the disclosed compounds decrease binding of Rev to an RRE RNA by at least 10% (such as at least 20%, 30%, 40%, 50%, 60%, 70%, 80%, 90%, 95%, 98%, or even 100%) compared to a control. The control may be binding of Rev to an RRE RNA in the absence of the compound or may be a reference value. Methods for determining binding of Rev to an RRE include electrophoretic mobility shift assays (EMSA), such as those described in Examples 1 and 2 herein. Additional methods for determining binding of Rev to an RRE include assays that measure the nuclear export activity of RRE, for example in a cell culture assay. In some examples, the assay includes an assay measuring synthesis of an HIV protein (such as Gag) that depends on binding of Rev to RRE. Another method for determining binding of Rev to an RRE utilizes surface plasmon resonance (SPR) to measure high affinity binding. Exemplary methods for determining nuclear export activity of RRE or HIV protein synthesis are provided in Examples 1 and 3 below. One of ordinary skill in the art can identify additional methods for determining binding of Rev to RRE or inhibition of Rev binding to RRE.

In some embodiments, the methods include treating or inhibiting HIV-1 infection in a subject by administering an inhibitor of Rev binding to RRE to the subject. In some examples, the compound includes those described in Section II above. Compositions and methods of administration to a subject (for example, to treat or inhibit HIV infection) are described in Section V, below.

IV. Methods of Identifying Cells Containing HIV or Delivering a Cargo Moiety to Cells Containing HIV Further disclosed herein are methods of identifying cells containing HIV RRE and/or delivering a cargo moiety to cells containing HIV RRE. In some examples, the cells are infected with HIV. For example, the RRE binders linked to a detectable label disclosed herein can be used in assays to determine whether cells contain or are infected with HIV (for example, to diagnose a subject infected with HIV). In other examples, the RRE binders can be used in assays to determine the viral load of a subject known or suspected to be infected with HIV, or to determine the effectiveness of treatment for HIV infection (for example, detecting a reduction in viral load in a patient following therapy). In addition, the RRE binding compounds linked to a cargo moiety disclosed herein can be used to deliver the cargo to HIV-containing cells. The cargo moiety can be a molecule that is toxic to cells (such as a radioisotope, RNA cleavage reagent, crosslinking agent, toxin, or molecule that increases apoptosis). By targeting delivery of the cargo to HIV-infected cells with the RRE binding compound, in some examples, the toxic effects of the cargo on non-infected cells can be minimized.

In some embodiments, methods of identifying cells that contain HIV RRE include contacting cells with one or more of the disclosed compounds that include a detectable label and detecting the label. Presence of the detectable label in a cell indicates that the cell contains HIV RRE (e.g., is infected with HIV). In some examples, the methods include contacting cells with the compound in vitro or in vivo (such as administering the compound including the detectable label to a subject).

In some examples, cells that contain or are suspected to contain HIV RRE are contacted with one or more of the disclosed compounds that are linked to a detectable label under conditions sufficient for the compound to enter the cells and bind to RRE in the cells. The cells may be in a sample obtained from a subject infected with HIV or suspected to be infected with HIV, such as a blood sample (for example, blood containing T cells) or lymph node sample (such as a lymph node fluid sample) collected from a subject. In particular examples, the methods include collecting the sample from a subject. In some examples, after contacting the cells with the compound linked to a detectable label, a washing step is performed, for example to reduce background fluorescence, remove any compound that has not entered the cells, and/or any non-specifically bound compound.

The detectable label is then detected by any suitable method, depending on the detectable label utilized. For example, if the detectable label is a radioisotope, the label can be detected by radiographic methods (for example, scintillation counting, gamma counting, or exposure to x-ray film or a phosphorimager screen). If the detectable label is a fluorescent label, the label can be detected by, for example, fluorescence microscopy or flow cytometry. In some examples, the label is detected by flow cytometry, which allows for identification of specific cell types, such as $CD4^+$ T cells, which are most likely to contain HIV.

In one non-limiting example, the label is detected with fluorescence anisotropy (such as fluorescence anisotropy microscopy). This technique allows discrimination of target bound and free fluorescent molecules (such as free detectably labeled RRE binders and detectably labeled RRE binders that are bound to an RRE RNA) and also can detect as little as a single fluorescent molecule. See, e.g., Luedtke and Tor (*Biopolymers* 70:103-119, 2003).

In other examples, one or more of the disclosed compounds linked to a detectable label is administered to a subject who is infected with or suspected to be infected with HIV. The detectable label is one that can be detected by in vivo imaging, such as by positron emission tomography (e.g., $^{11}C$, $^{13}N$, $^{18}F$, or $^{82}Rb$), scintigraphy (such as $^{99}Tc$ or $^{131}I$) or single-photon emission computed tomography (e.g., $^{131}I$, $^{99}Tc$, or $^{111}In$). Detection of the label in cell(s) indicates that the cell(s) contain HIV, for example, are infected with HIV.

Due to the sensitivity and specificity of the disclosed methods, cells infected with HIV can in some examples be detected within a short time of infection. In some examples, the disclosed methods can detect HIV (for example HIV RRE RNA) in cells in a sample from a subject who was exposed to or infected with HIV within about 6 months or less of exposure or infection (for example, within about 5 months, about 4 months, about 3 months, about 10 weeks, about 8 weeks, about 6 weeks, about 4 weeks, or about 2 weeks of exposure or infection). In addition, in some examples, the disclosed methods can detect about 10,000 copies or less of HIV genomic RNA in a sample or even in a single cell (such as about 5000, about 1000, about 100, about 10, or even about 1 copy of HIV genomic RNA in a sample or a cell).

In other embodiments, the methods include delivering a cargo moiety to cells containing HIV RRE (for example delivering a cargo moiety, such as a radioisotope, RNA cleavage agent, crosslinking reagent, or toxin to HIV RNA-containing cells). In some examples, the methods include contacting cells with one or more of the disclosed compounds that includes a cargo moiety. In some examples, the method includes contacting cells with the compound in vitro or in vivo (such as administering the compound including the cargo moiety to a subject).

V. Pharmaceutical Compositions and Administration

The presently described compounds, and pharmaceutically acceptable salts thereof, are useful for treating subjects (such as humans or animals) suffering from a condition characterized by a replication or integration of HIV and for helping to inhibit, delay, or in some cases prevent, the onset of such a condition. For example, the compounds are useful for treating or inhibiting infection by HIV, AIDS, or ARC. When treating, inhibiting, or preventing these diseases, the compounds can either be used individually or in combination, as is best for the subject. Appropriate subjects can be selected for administration of the disclosed compounds, as described in more detail below.

The compounds and pharmaceutical compositions are especially useful in the inhibition of Rev binding to the HIV RRE, the prevention or treatment of infection by HIV and the treatment of consequent pathological conditions such as AIDS. Treating AIDS or preventing, inhibiting, or treating infection by HIV is defined as including, but not limited to, treating a wide range of stages of HIV infection: AIDS, ARC (AIDS related complex), both symptomatic and asymptomatic, and actual or potential exposure to HIV. For example, the compounds are useful in treating infection by HIV after suspected past exposure to HIV by e.g., blood transfusion, exchange of body fluids, bites, accidental needle stick, or exposure to a patient's blood during surgery.

In treating or preventing the above diseases, the compounds (including compounds linked to a detectable label or a cargo moiety) are administered in a therapeutically effective amount. The therapeutically effective amount will vary depending on the particular compound used and the route of administration, as is well known. In treating a subject displaying any of the conditions discussed above, a clinician may administer a compound immediately and continue administration indefinitely, as needed. Upon HIV infection or exposure, even though the patient does not have symptoms of disease, administration of the compounds may be started before symptoms appear, and treatment may be continued indefinitely to prevent or delay onset or recurrence of disease.

In some embodiments, the methods disclosed herein involve administering to a subject in need of treatment (such as a subject infected with, or suspected to be infected with, HIV) a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

In some embodiments, one or more of the disclosed compounds (including compounds linked to a detectable label or cargo moiety) are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., 21$^{st}$ Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent (such as an anti-retroviral agent) for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The active compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound (such as a disclosed compound that binds HIV RRE, including such compounds linked to a detectable label or a cargo moiety), a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data (such as testing in an animal model of HIV infection). It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. When administered orally, an administered amount therapeutically effective to inhibit binding of Rev to RRE, to inhibit HIV replication, to inhibit, prevent, or treat HIV infection, and/or to treat or prevent AIDS is from about 0.1 mg/day to about 1,000 mg/day. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds disclosed herein may also be used in combination with a therapeutically effective amount of one or more additional HIV treatment agents such as nucleoside analog reverse transcriptase inhibitors, non-nucleoside reverse transcriptase inhibitors, protease inhibitors, integrase inhibitors, other antivirals, immunomodulators, anti-infectives, other antibiotics, or other medications useful against HIV infection or AIDS. Exemplary antivirals include amprenavir, abacavir, acyclovir, adefovir dipivoxil, alpha interferon, retrovir, ansamycin, beta-fluoro-ddA, cidofovir, curdlan sulfate, cytovene, ganciclovir, delaviridine, dideoxycytidine (ddC), dideoxyinosine (ddI), efavirenz, famciclovir, hypericin, interferon beta, interferon alfa-n3, indinavir, lamivudine (3TC), lobucavir, nelfinavir, nevirapine, novapren, phosphonoformate, probucol, ritonavir, saquinavir, didehydrodeoxythymidine, valaciclovir, virazole, ribavirin, zalcitabine, and zidovudine (AZT). Exemplary immunomodulators include bropirimine, acemannan, interferons such as gamma interferon and alpha interferon, tumor necrosis factor, granulocyte macrophage colony stimulating factor, interleukin-2, recombinant or soluble CD4. Exemplary anti-infectives include clindamycin, primaquine, fluconazole, nystatin, ornidyl, eflornithine, pentamidine, trimethoprim, trimethoprim/sulfa, piritrexim, spiramycin, trimetrexate.

Examples of combination therapy are simultaneous or alternating treatments with a presently described compound and an inhibitor of HIV protease, inhibitor of HIV integrase, and/or a non-nucleoside inhibitor of HIV reverse transcriptase. An optional fourth component in the combination is a nucleoside inhibitor of HIV reverse transcriptase, such as AZT, 3TC, ddC or ddI. Suitable HIV protease inhibitors include indinavir, nelfinavir, ritonavir, and saquinavir. Suitable non-nucleoside inhibitors of HIV reverse transcriptase include nevirapine and efavirenz. In such combinations the compounds and other active agents may be administered separately or in conjunction. In addition, the administration of one element may be prior to, concurrent to, or subsequent to the administration of other agent(s).

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians who are skilled in therapy of retroviral infections, diseases, and associated disorders.

EXAMPLES

The following examples are illustrative of disclosed methods. In light of this disclosure, those of skill in the art will recognize that variations of these examples and other examples of the disclosed methods would be possible without undue experimentation.

Example 1

Topological Structure of the HIV-1 Rev Response Element

Introduction

Virtually all mRNAs in mammalian cells are spliced before leaving the nucleus. However, retroviral replication requires that some viral RNAs be exported while retaining some or all of their introns, since these RNAs will serve as mRNAs for the gag, gag-pol and env gene products and as genomes to be encapsidated in progeny virions. HIV-1 fulfills this requirement by encoding the Rev protein; this protein binds to an element within the env-coding region of the viral RNA, called the Rev response element (RRE). The Rev-RRE complex then engages Crm1 (Xpol1) and RanGTP to form a host export complex enabling the translocation through the nuclear pore complex. The secondary structure of the HIV-1 RRE includes a series of stems. Stems I, II, III/IV, and V are arranged around a central 4-way junction, with stem-loop II split into a proximal stem (IIA) and two distal stem-loops (IIB and IIC) around a 3-way junction (Legiewicz et al., *Proc Natl Acad Sci USA* 105: 14365-14370, 2008). There is a high-affinity site for Rev in stem-loop IIB (Battiste et al., *Science* 273: 1547-1551, 1996; Cook et al., *Nucleic Acids Res* 19:1577-1583, 1991; Heaphy et al., *Cell* 60:685-693, 1990; Heaphy et al., *Proc Natl Acad Sci USA* 88:7366-7370, 1991; Kjems et al., *Proc Natl Acad Sci USA* 88:683-687, 1991; Lusvarghi et al., *Nucleic Acids Res* 41:6637-6649, 2013; Malim et al., *Nature* 338:254-257, 1989; Malim et al., *Cell* 60:675-683, 1990; Pond et al., *Proc Natl Acad Sci USA* 106:1404-1408, 2009) and a second Rev-binding site (IA) in stem I (Daugherty et al., *Mol Cell* 31:824-834, 2008). Initial occupancy of the IIB site (Cook et al., *Nucleic Acids Res* 19:1577-1583, 1991; Tiley et al., *Proc Natl Acad Sci USA* 89:758-762, 1992) is considered a prerequisite to Rev oligomerization (Daly et al., *Nature* 342:816-819; 1989; Daly et al., *Biochemistry* 32:10497-10505, 1993; Malim and Cullen, *Cell* 65:241-248, 1991; Mann et al., *J Mol Biol* 241:193-207, 1994), in which as many as 10 to 12 Rev molecules may bind to a single RRE (Mann et al., *J Mol Biol* 241:193-207, 1994), and this assembly is necessary for Rev-mediated nuclear export of RRE-containing viral transcripts (Hoffman et al., *PloS One* 7:e38305, 2012).

Recent structures of Rev-Rev dimers reveal a hydrophobic core that drives Rev-Rev dimer formation and an arrangement in which two 17-residue arginine-rich motifs (ARMs) in the two monomers point away from each other, with a separation distance of approximately 55 Å and an angle of 120-140° (Daugherty et al., *Nat Struct Mol Biol* 17:1337-1342, 2010; DiMattia et al., *Proc Natl Acad Sci USA* 107:5810-5814, 2010). Oligomerization is essential for Rev function, as demonstrated by analyses of Rev mutants that are deficient in dimerization (Malim and Cullen, *Cell* 65:241-248, 1991; Zapp et al., *Proc Natl Acad Sci USA* 88:7734-7738, 1991); indeed, the C-terminal dimerization domain of the protein can be replaced by unrelated dimerization domains without loss of function (Hoffman et al., *PloS One* 7:e38305, 2012). Formation of the multimeric Rev-RRE complex is driven in part by hydrophobic Rev-Rev interactions (Cook et al., *Nucleic Acids Res* 19:1577-1583, 1991; Daugherty et al., *Mol Cell* 31:824-834, 2008; Daugherty et al., *Nat Struct Mol Biol* 17:1337-1342, 2010; DiMattia et al., *Proc Natl Acad Sci USA* 107:5810-5814, 2010; Mann et al., *J Mol Biol* 241:193-207, 1994; Pond et al., *Proc Natl Acad Sci USA* 106:1404-1408, 2009), in addition to the binding of multiple Rev proteins to less well-defined binding sites on the RRE. The cooperative binding has an affinity about 500 times greater than that of the tightest single Rev-IIB interaction (Daugherty et al., *Proc Natl Acad Sci USA* 107:12481-12486, 2010; Daugherty et al., *Mol Cell* 31:824-834, 2008), and the multiple Rev-binding events may be driven and dictated by overall topological constraints (Daugherty et al., *Proc Natl Acad Sci USA* 107: 12481-12486, 2010). While significant progress has been made in the past two decades in understanding the Rev-RRE interaction, little is known about the role of the RRE architecture in the specificity and cooperativity of Rev-RRE interactions. Since the Rev-RRE interaction lacks high sequence specificity, with only preferential binding to purine-rich major grooves, and Rev could potentially interact with other RNA targets with various affinities (Bayer et al., *RNA* 11:1848-1857, 2005; Landt et al., *J Mol Biol* 351:982-994, 2005; McColl et al., *Proc Natl Acad Sci USA* 96:9521-9526, 1999; Mishra et al., *J Mol Biol* 393:369-382, 2009; Wang et al., *Biophys J* 99:3454-3462, 2011; Xu and Ellington, *Proc Natl Acad Sci USA* 93:7475-7480, 1996), the basis for selection of HIV-1 mRNA for nucleocytoplasmic transport remains a mystery (Hammarskjold and Rekosh, *Viruses* 3:484-492, 2011). The key to resolving this mystery is the three-dimensional structure of the RRE.

Despite recent progress in both X-ray crystallography and solution NMR spectroscopy, the RRE overall topology and three-dimensional structure has remained unknown. Therefore, alternative strategies are warranted. Small angle X-ray scattering (SAXS) is a solution-based method, does not require crystallization, and has almost no size limitation. Meaningful protein structural models of large systems have been constructed from high-resolution domain structures and SAXS data using rigid body refinement (Koch et al., *Q Rev Biophys* 36:147-227, 2003). Thus, almost in parallel, heuristic topological structural models of RNAs can be constructed when accurate information about the secondary structure, relative accessibility of individual residues in an RNA, and other structural information are available (Funari et al., *J Biol Chem* 275:31283-31288, 2000; Hajdin et al., *RNA* 16:1340-1349, 2010; Lipfert et al., *Structure* 16:1357-1367, 2008). In particular, construction of RNA structural models based on SAXS-derived envelopes is feasible, because the main structural RNA elements are duplexes that exist almost exclusively in A-form conformation with a root-mean-square-deviation (RMSD) of backbone heavy atoms within 1±0.5 Å over all known structures in structural databases (Wang et al., *Biophys J* 99:3454-3462, 2009). The possible resolution of such an envelope is approximately defined by $2\pi/q$, where q is the momentum transfer. Thus, in principle, scattering data recorded for q ranging up to 0.3 $\text{Å}^{-1}$ is sufficient to identify an A-form duplex that has a diameter of 20-25 Å, q ranging up to 0.8 $\text{Å}^{-1}$ can clearly delineate the major groove of an RNA (unpublished data), and high-resolution and quality SAXS/WAXS data with q up to 2.3 $\text{Å}^{-1}$ can even reveal fine structural features such as the spacing between phosphate groups in DNA at a ~2 Å resolution (Zuo et al., *Proc Natl Acad Sci USA* 103:3534-3539, 2006). Thus, SAXS/WAXS is a bona fide tool for structure determination and characterization. When used in combination with biochemical and functional studies, as illustrated herein, it can address important biological questions and becomes very useful especially when high-resolution structures of RNA are unattainable using conventional methods.

Results

A Unique Global Topological Structure of the RRE RNA.

Figure 1A:
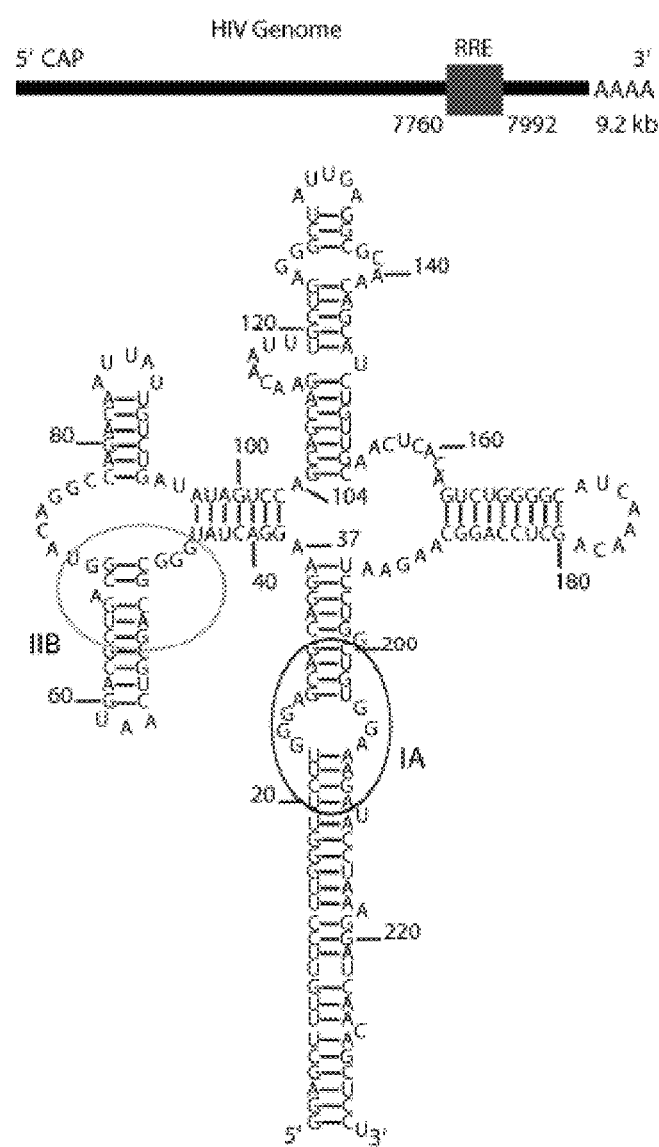
Figure 1D:
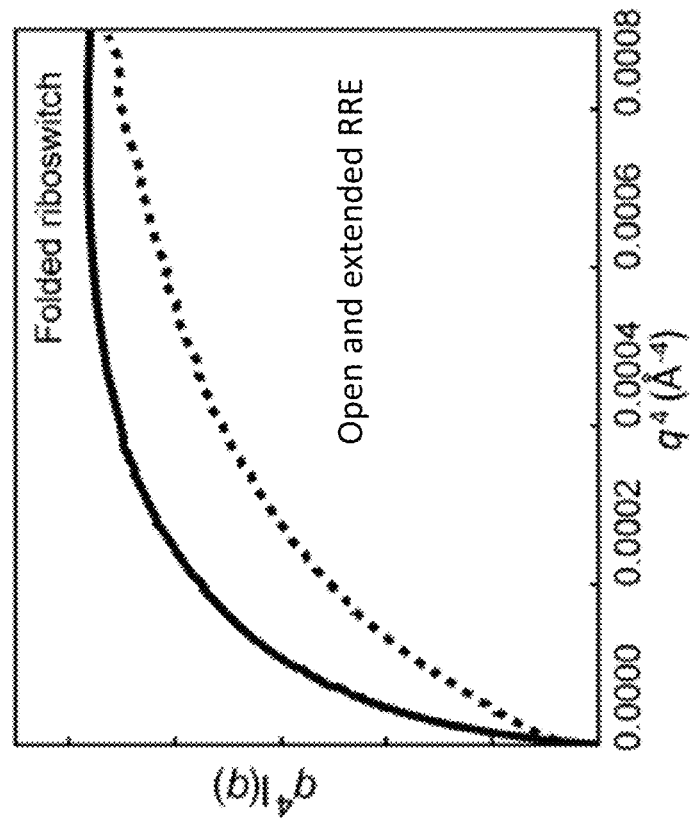
Figure 1E:
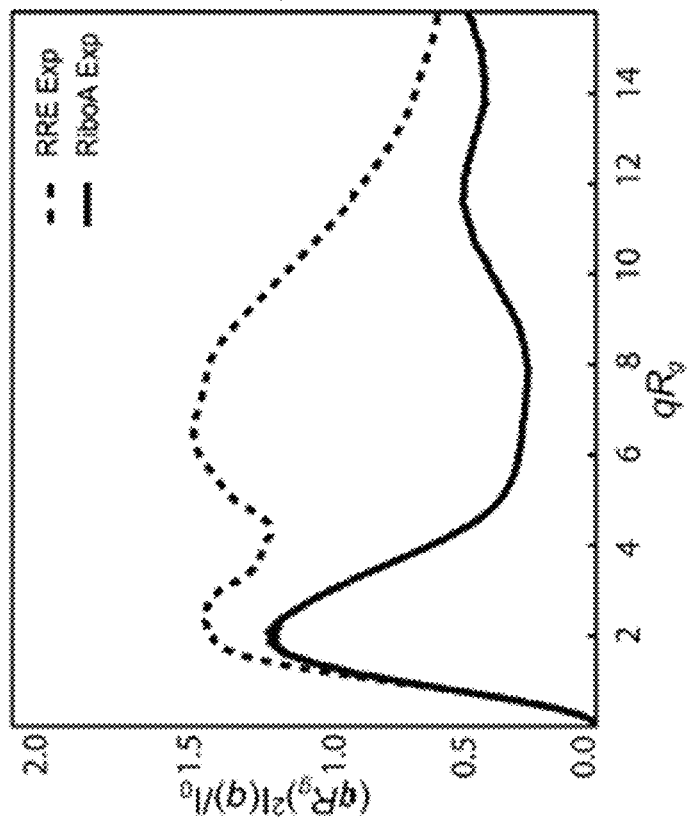

The genomic location of the RRE and the secondary structure of the RRE fragment used in this study are illustrated in FIG. 1A. This construct is identical to one whose secondary structure was mapped using SHAPE technology (Legiewicz et al., *Proc Natl Acad Sci USA* 105:14365-14370, 2008); the RRE in genomic RNA from virus particles also has the same general secondary structure as that studied here (Watts et al., *Nature* 460:711-716, 2009; Wilkinson et al., *PLoS Biol* 6:e96, 2008). The 3D structure of RRE RNA as analyzed by SAXS. The experimental SAXS curve, with scattering intensity I(q) plotted versus momentum transfer q, together with the pair distance distribution function (PDDF) and the Kratky and Porod-Debye plots of the RRE, are shown in FIG. 1B-1E, respectively. The Guinier region of the scattering curve (inset in FIG. 1B) is linear, indicating that RRE is monodisperse and homogeneous in solution (Jacrot, *Rep Prog Phys* 39:43, 1976). The scattering curve in the high-q region has fine features typical of nucleic acids, such as P1 and P2 peaks (FIG. 1B) (Zuo et al., *Proc Natl Acad Sci USA* 103:3534-3539, 2006), albeit with attenuated peak intensity compared to those of a simple duplex. This is likely due to the presence of non-duplex structure elements as well as dynamic conformational averaging within RRE molecules. The PDDF shows that the RRE has two main distance populations, one at ~25 Å (the shoulder at the left side of the curve in FIG. 1C) and one at 50-60 Å. The second derivative of the PDDF (the inset in FIG. 1C) indicates that the most populated distances in the RRE are ~10, ~25 and ~55 Å. The first two are related to the dimensions across an A-form RNA duplex, whose diameter is about 25 Å, while the latter suggests the presence of a structural feature in which two major structural segments are separated by 50-60 Å. The dimensionless Kratky (Rambo and Tainer, *Nature* 496, 477-481, 2013) and Porod-Debye plots (FIGS. 1D and 1E), plotted as $(qRg)^2 I(q)/I_0$ vs. $qR_g$ and $I(q) \cdot q^4$ vs. $q^4$ (Rambo and Tainer, *Biopolymers* 95:559-571, 2011), respectively, suggest that the RRE RNA is extended and open, rather than bundled double helices such as in the adenine riboswitch RNA (Serganov et al., *Chem and Bio* 11:1729-1741, 2004) (FIGS. 1D and 1E). These structural features are direct observables, not subject to possible bias due to limitations of software, and are therefore important in guiding the interpretation presented below.

Figure 1F:
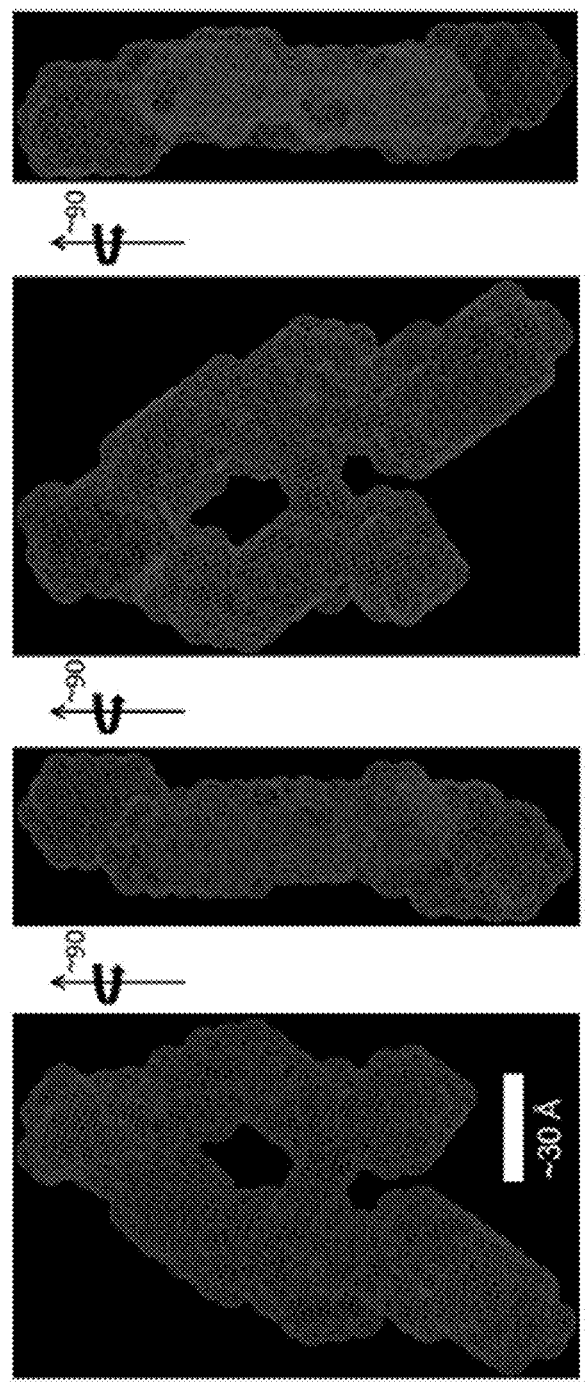

The three-dimensional structure of the RRE was determined from the SAXS data using a two-step protocol. The resulting average envelope is shown in FIG. 1F. The RRE adopts an 'A'-like topology, with one leg longer than the other. This open and extended structure appears to represent the native structure at physiological $Mg^{2+}$ concentration. Even at higher $Mg^{2+}$ concentrations, the overall topology remains similar (FIGS. 2A-2C). The major portions of the two legs, i.e. the two main structural segments, are separated by 50-60 Å, in agreement with the PDDF (FIG. 1C). Such an extended and open structure may permit the binding by multiple copies of Rev.

Locations of the RRE RNA Domains.

Figure 4E:
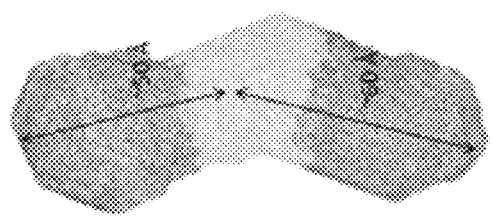

The locations of the individual RRE domains were identified using a SAXS-aided divide-and-conquer approach (FIGS. 3, 4A-4F). Briefly, the construct composed of domains II, III and IV (referred to from now on as "domains II-III-IV"), has an overall shape and size that exclusively matches the short side of the "A" (FIGS. 3; 4A-4D), whereas the construct consisting of domains I and V (called "domains I-V" below) (FIG. 3), with its unique, long stem I, matches the long side of the 'A' in both shape and length. The ~25 Å envelope thickness of the magenta construct is similar to that of a duplex, indicating that domains II and III, which are linked by a single residue, A104 (FIG. 3), along with IV may be co-axially stacked with a possible kink. The notion that domains II, III and IV may be co-axially stacked was further supported by SAXS analysis of two more subconstructs, II-III-IV-X and II-III-IV-C(FIGS. 4B-4D). The sequences of subconstructs II-III-IV-X and II-III-IV-C(FIG. 4B) are identical to that of subconstruct II-III-IV except for a 7-bp insertion at region IIB in sub-construct II-III-IV-X and an addition of 5 bp at the junction between domain II and domains III-IV in subconstruct II-III-IV-C (FIGS. 4B-4D, Table 1). The subconstructs of II-III-IV-X and II-III-IV-C share very similar global shape with that of subconstruct II-III-IV (FIGS. 4B-4D), indicating that the possible coaxial stacking between domain II and III-IV prevails in all 3 subconstructs. Lastly, the elongated and bent envelope (right side of FIG. 3) suggests that domains I and V may be arranged via either a coaxial stacking or helix-loop-helix interaction, the type of structure that has generally been observed for four-way junctions (Laing and Schlick, *J Mol Biol* 390:547-559, 2009).

Figure 4F:
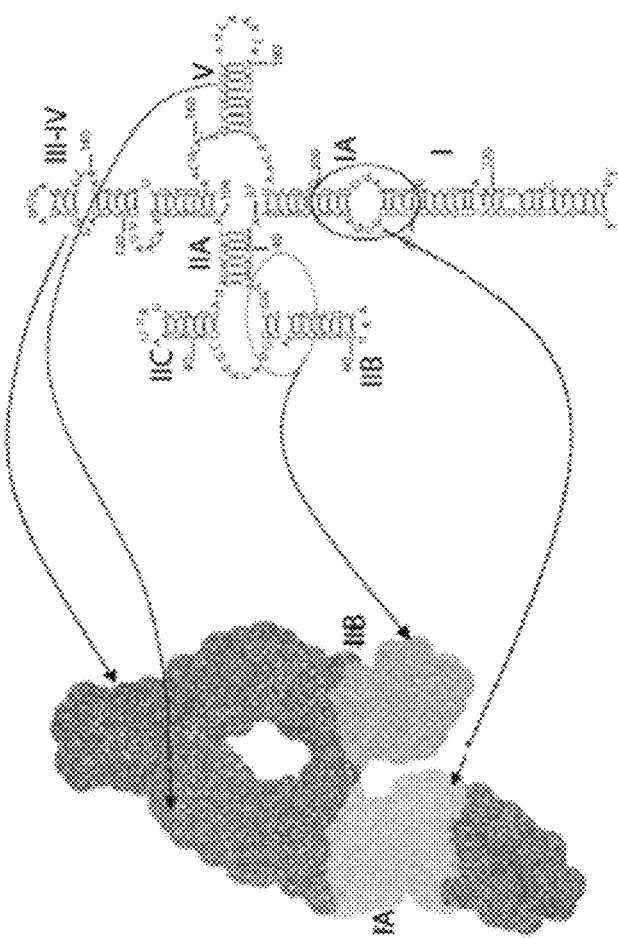

(FIG. 3) is ~60 Å, assuming a standard A-form duplex (FIG. 4E). This distance places site IA in the long leg, across from site IIB on the opposing leg of the 'A' with a separation of ~55 Å (FIG. 5A). A summary of the RRE domain locations is illustrated in FIG. 4F. These combined SAXS envelopes, together with the approximate layout of the domains, make it possible to construct a 3D structural model of the RRE using the software package G2G (Wang et al., *Biophys J* 99:3454-3462, 2009). An overlay of the 3D model, drawn in ribbon diagrams, with the 3D RRE SAXS envelope is shown in FIG. 5A.

The Conformation Space of the RRE Characterized by SAXS.

The RRE can be recognized by a chimeric Rev (Hoffman et al., *PloS One* 7:e38305, 2012), as well as by wild-type (WT) Rev. This suggests that the RRE structure retains some flexibility. The possible conformation space of the RRE was therefore investigated. SAXS has been used to characterize the conformation space of flexible or disordered proteins (Bernado and Svergun, *Mol Biosyst* 8:151-167, 2012;

TABLE 1

Primary Sequences of RRE Mutant Subconstructs Referenced to RRE Wild Type Sequence.

| | |
|---|---|
| RRE Insertion of 1 Turn | Insertion of one turn of a duplex between $^{36}$A and $^{37}$A ($^{36}$A-CGGGCAUGGG-$^{37}$A) (SEQ ID NO: 21) and $^{155}$A and $^{156}$A ($^{155}$A-CCCAUGCCCG-$^{156}$A) (SEQ ID NO: 22) |
| RRE Insertion of 1.5 Turns | Insertion of one and a half turns of a duplex between $^{36}$A and $^{37}$A ($^{36}$A-CGGAUCGGGCAUGGG-$^{37}$A) (SEQ ID NO: 23) and $^{155}$A and $^{156}$A ($^{155}$A-CCCAUGCCCGAUCCG-$^{156}$A) (SEQ ID NO: 24) |
| RRE Insertion of 2 Turns | Insertion of two turns of a duplex between $^{36}$A and $^{37}$A ($^{36}$A-CGUGACGGAUCGGGCAUGGG-$^{37}$A) (SEQ ID NO: 25) and $^{155}$A and $^{156}$A ($^{155}$A-CCCAUGCCCGAUCCGUCACG-$^{156}$A) (SEQ ID NO: 26) |
| Domain I | RRE domains I from $^1$G to $^{35}$G UUCG $^{195}$C to $^{233}$U |
| Domains I-V | RRE domains I and V from $^{163}$G to $^{232}$C UUCG $^1$G to $^{36}$A |
| Domains II-III-IV | RRE domains II-III-IV from $^{38}$G to $^{156}$A |
| Domains II-III-IV-X | Insertion of 7 bp (underlined residues) between $^{56}$C and $^{60}$G ($^{56}$C-<u>UCCGCGC</u>GUA<u>AGCGCGGA</u>-$^{60}$G) (SEQ ID NO: 27) in Domains II-III-IV |
| Domains II-III-IV-C | Addition of a 5 bp-duplex which links $^{37}$A and $^{156}$A (GGAGGA-$^{37}$A, $^{156}$A-UCCUCG) in Domains II-III-IV |

The construct II-III-IV-X with the 7-bp extension of stem-loop IIB (FIGS. 4A-4D) was also used to determine whether stem-loop IIB is located at the top or the bottom of the shorter leg of the 'A.' Comparison of the shape of this construct with that of the RRE envelope confirmed the location of IIB as the lower part of the short leg of the 'A' (FIG. 4A). Next, the location of domain IA was derived by the following rationale: excluding single bulges, the distance spanned by the 23 bp between the end of Stem I and the beginning of the purine-rich IA internal asymmetrical loop Rambo and Tainer, *Biopolymers* 95:559-571, 2011) and DNA (Schwieters and Clore, *Biochemistry* 46:1152-1166, 2007) using SAXS-restrained ensemble calculation approaches, where the scattering intensity is calculated as:

$$I(q) = \sum_i w_i I_i(q)$$

$w_i$ is the weight of ensemble member i, taken as $1/N_e$ here, and $I_i(q)$ is the contribution to the scattering intensity from ensemble member i. If the surface-bound solvent contribution is omitted, the $I_i(q)$ of an individual member i can be calculated using the Debye formula (Debye, *Annalen der Physik* 46:809-823, 1915). A detailed description of the ensemble calculation is presented in the Extended Experimental Procedures (below). This calculation reveals that a minimum ensemble size of three is sufficient for a good fit with the experimental scattering data (FIG. 5B), indicating conformational flexibility of the RRE RNA in solution. This flexibility may originate from pivot points, such as loops, internal loops, junctions and bulges (Bailor et al., *Curr. Opin. Struct. Biol.* 21:296-305, 2011). Because of flexibility, the characteristic dimensional parameters of the RRE, such as radius of gyration $R_g$ and maximum distance $D_{max}$, are better represented by distance distributions than by single values (FIG. 6).

The pattern of the pairwise RMSD among the top 20 ensemble structures vs. residue number coincides with that of flexibility probed by chemical reactivity (FIG. 5C) (Legiewicz et al., *Proc Natl Acad Sci USA* 105:14365-14370, 2008). The relative distance between the two known Rev binding sites ($D_{duet}$ in FIG. 5D) distributes within a narrow range, 54±4 Å, among all structures of the ensembles. The relatively restricted positioning of these two Rev binding sites is likely due to the constraint imposed by the one-residue linker, A37, between domains I and II in the four-way junction (FIG. 1A). Furthermore, histograms of distances between points A and B at the top of the "A" suggest a possible subset of conformations with an "H-like" topology, due to relative movement of the two legs of the "A" (FIG. 5E). The distance distribution between the two main structural segments varies between 45-60 Å, and these two structural segments may constitute two tracks of a scaffold for RRE-directed oligomerization of Rev.

Structural Determinants for Formation of High-Order Rev-RRE Complexes.

To test the significance of the RRE topology and its structural determinants, the binding and oligomerization of the Rev protein to several RRE mutants, as well as to WT RRE was characterized by electrophoretic mobility shift assay (EMSA) and functional studies (see below). The RRE mutants included two truncation mutants (FIG. 3) and three insertion mutants (FIG. 7A). The insertion mutants were made by inserting 10- or 20-basepairs into the "crossbar" between the two legs of the "A." SAXS analysis showed, as expected, that these mutant RREs retained their two-legged structure, but the insertions increased the distance between the two legs, presumably by forming a 10- or 20-bp double helix within the crossbar (FIGS. 7A and 7B). A mutant RRE with a 15-bp insertion in the crossbar (FIGS. 7A and 7B) was also constructed; this insertion represents 1/2 turns of a double helix, so that one of the two legs is presumably inverted with respect to the other. This is confirmed by superimposition and comparison of the envelopes of domains II-III-IV and the 15-bp insertion mutant (FIGS. 7C and 7D). The two envelopes match in the domain II region only after rotating the envelope of domains II-III-IV by 180° around a horizontal axis (FIG. 7C); without such a rotation, the envelopes do not match (FIG. 7D). FIG. 7B also shows that the distance between sites IA and IIB is increased in this mutant, as well as in the 10- and 20-bp insertion mutants. The agreement of these results with predictions is a strong validation of the overall SAXS-derived topology for the RRE.

To assess the binding of Rev to these RREs, WT or mutant RRE RNAs were incubated with increasing amounts of the Rev protein. As shown in FIG. 8A (top panel), some WT RRE RNA was shifted at Rev:RRE ratios as low as 2:1. The shifted RNA was resolved into 6-7 distinct bands. These Rev-RRE complexes were grouped into low-(bands 1 and 2), mid-(bands 3-5), and high-order complexes (above band 5). At higher Rev:RRE ratios, the intensity of high-order bands is increased, and at approximately 30:1 stoichiometry, all or nearly all of the RRE has been shifted to high-order Rev-RRE complexes.

A truncated RRE containing domains II-III-IV, which harbors the primary high affinity Rev-binding site on domain IIB, showed several faint shifted bands only at ratios of 16:1-32:1 (FIG. 8A, second panel). However, the high-order complexes formed at high ratios with WT RRE were never seen with this mutant (FIG. 8B, magenta plot). In dramatic contrast, with the I-V mutant RRE, which harbors the secondary binding site IA in domain I, a faint shifted band appeared at about 32:1, but no other bands were ever formed, even at higher stoichiometries (FIG. 8A, third panel; FIG. 8B). Thus, neither leg alone binds Rev with affinity or cooperativity comparable to that of the intact RRE; both legs are required for formation of high-order complexes. The difference between the two RRE fragments is also consistent with the well-established significance of site IIB for Rev binding.

EMSAs were performed using the three RRE insertion mutants and they also began to shift at 2:1 stoichiometries (bottom three panels, FIG. 8A). However, unlike the results with WT RRE, only low-order complexes appeared at low Rev:RRE ratios, and intermediate complexes did not appear until the Rev:RRE ratio was ~30:1. At even higher Rev:RRE ratios, high-order complexes were observed, though often as a smear rather than discrete bands (FIG. 8B). Presumably, the impaired ability of these insertion mutants to form high-order complexes is due to the increased distance between the two legs. The residual binding affinity of Rev for the insertion mutants might be due to the presence of the major grooves in the inserted duplex, which are also positioned near the high-affinity IIB site. These major grooves might serve as structural analogs of the IA site, resulting in formation of a distorted initial Rev:RRE mutant complex. In summary, both legs of the "A" as well as the optimal separation of the two legs are important for formation of high order Rev:RRE complexes.

Functional Implications of the RRE Structural Determinants.

To further test the functional relevance of these topological arrangements, the effects of these mutations on the nuclear export activity of the RRE was determined in 293T human cells. As shown in FIGS. 8C and 8D, an assay in which the Gag mRNA contained WT RRE was devised, so that synthesis of Gag protein was completely dependent upon the co-expression of Rev. Gag protein production was measured by immunoblotting of cell lysates using antiserum against a fragment of Gag. Mutations in the reporter plasmid ensured that the Gag protein, which is the "readout" of the assay, is not cleaved in or exported from the cells, but remains as a single band in the immunoblot. Using this assay, the nuclear export activity of mutant RREs in which either domains II-III-IV or domains I-V had been deleted was measured. Neither mutant exhibited detectable activity in this RRE activity assay (Lanes under I-V and II-III-IV, FIG. 8D). As these isolated domains both maintained the same overall structures as in the intact RRE (FIG. 3) and since the II-III-IV RNA retained the IIB site and multiple major grooves, these results show that neither of the single legs alone is sufficient for RRE function in vivo; rather, both legs of the "A" are required.

Three insertion mutants were tested in the functional RRE assay. Each insertion reduced the level of Gag synthesis by 6- to 9-fold (Lanes under 1, 1.5 and 2 Turns, FIG. 8D). These results suggest that the 55 Å distance between the two legs of the "A" is optimal for RRE function in vivo. The residual activity might be attributed partly to the flexibility of the RRE structure and/or the flexibility of the Rev protein, as suggested by the differences in the angles and distances between the two ARMs observed in the two crystal structures of Rev dimer (Daugherty et al., *Nat Struct Mol Biol* 17:1337-1342, 2010; DiMattia et al., *Proc Natl Acad Sci USA* 107:5810-5814, 2010). As noted above, the structural versatility of the RRE RNA is also evident in its ability to form functional complexes with chimeric proteins in vivo (Hoffman et al., *PloS One* 7:e38305, 2012). In summary, the in vivo functional assays data correlate very well with the in vitro results, suggesting that under our assay conditions, only the high-order complexes are capable of supporting RNA export; both the in vitro and in vivo studies illustrate that both legs of the "A" structure are required for the formation of high-order Rev:RRE complexes and optimal RRE function, with a preferred distance between the two legs of approximately 55 Å.

Discussion

The "match" between the distance separating the primary Rev-binding sites in the RRE of this report and that between ARMs in Rev dimers (Daugherty et al., *Nat Struct Mol Biol* 17:1337-1342, 2010; DiMattia et al., *Proc Natl Acad Sci USA* 107:5810-5814, 2010) suggested a solution to the conundrum of how Rev discriminates between RRE-containing RNAs and other RNAs, specifically promoting nuclear export of the former. The role of the novel "A" shape in the specific binding of Rev to the RRE and in RRE function was tested. Removal of either of the two legs of the "A" eliminated both specific binding (the second and third panels, FIG. 8A) and RRE function (FIG. 8D). Moreover, insertions in the "crossbar" of the RRE which increased the distance between the two binding sites impaired, but did not completely prevent, both specific binding (FIGS. 8A and 8B) and RRE function (FIG. 8D). Taken together, these results provide strong support for the idea that the spatial opposition of the two sites is essential for Rev binding and function, and that the distance between them, corresponding to the "span" of the two ARMs in a Rev dimer, is optimal for binding and function.

Based on these observations and the structural features of the RRE presented here, the following model for Rev-RRE interactions is proposed. The overall RRE architecture positions the IIB and IA Rev binding sites at an optimal distance and orientation for initial binding of two Rev molecules. Subsequently, hydrophobic Rev-Rev interactions and general affinity of ARMs for the major grooves along the two legs facilitate the formation of a functional complex between an RRE RNA and multiple Rev molecules (FIG. 9). A structural model is presented in FIG. 10.

The results and model presented herein are consistent with a number of properties of the Rev-RRE system. It is known that IIB alone is insufficient for initiation of nuclear export (Daugherty et al., *Mol Cell* 31:824-834, 2008; Malim and Cullen, *Cell* 65:241-248, 1991; Mann et al., *J Mol Biol* 241:193-207, 1994) and that mutating a single residue in IA reduces Rev affinity for RRE ~5-fold (Daugherty et al., *Mol Cell* 31:824-834, 2008), while affinity of Rev for the intact RRE is 500 times greater than its affinity for an isolated IIB motif (Daugherty et al., *Proc Natl Acad Sci USA* 107:12481-12486, 2010; Daugherty et al., *Mol Cell* 31:824-834, 2008; Daugherty et al., *Nat Struct Mol Biol* 17:1337-1342, 2010). In fact, it has been speculated that a 'composite binding site' may exist that contributes to specificity and cooperativity (Daugherty et al., *Nat Struct Mol Biol* 17:1337-1342, 2010; DiMattia et al., *Proc Natl Acad Sci USA* 107:5810-5814, 2010). More specifically, two ARMs in a Rev dimer have previously been proposed to bind to IIB on one side and an unknown stem loop, presumably IA, on the opposing side (DiMattia et al., *Proc Natl Acad Sci USA* 107:5810-5814, 2010). Furthermore, two different sets of residues in Rev are involved in binding to the IIB and IA sites, suggesting a topological asymmetry of the two separate sites (Daugherty et al., *Mol Cell* 31:824-834, 2008), consistent with the topologically asymmetrical setting of IIB and IA in our model. The model presented herein also appears to be consistent with atomic force microscopy observations in which Rev oligomerization appears to take place on the entire RRE, including domain I (Pallesen et al., *FEBS J.* 276:4223-4232, 2009). In conclusion, our results reveal the global structural constraints that appear to drive the specificity and cooperative binding of multiple Rev molecules required for RRE function.

Experimental Procedures

Plasmid Construction and RNA Sample Preparation.

RRE-containing plasmids used for in vitro transcription or cell-based assays were modified as needed by site-directed mutagenesis or inverse PCR. Linearized plasmids were used as templates for in vitro transcription. RNA samples were gel-purified without refolding and washed extensively by filtration.

SAXS Collection, Processing, Analysis and Ab Initio 3D Shape Reconstructions.

SAXS/WAXS data acquisition, analysis, including distance distribution and $R_g$ calculations, are described in the Extended Experimental Procedures (below). The procedures for data collection, processing and analysis are similar to that previously described (Wang et al., *Biophys J* 99:3454-3462, 2009) and are in full conformity with the recently published recommended standards (Jacques et al., *BMC Struct Biol* 12:9, 2012). Data-collection and processing used the in-house program package called NCI-SAXS, while analysis used the ATSAS program package by Svergun and co-workers (available on the World Wide Web at embl-hamburg.de/biosaxs/). Ab initio modeling was performed using the program DAMMIN (Svergun, *Biophys J* 77:2896-2896, 1999) and a two-step protocol. The two-step protocol is described as follows. The initial search volume was chosen as 'sphere,' with a diameter 10-20× greater than the $D_{max}$ of the corresponding construct, to avoid distortion caused by possible underestimation of $D_{max}$. Thirty-two independent DAMMIN runs were performed in the 'slow' mode. The parallelepiped search volume with defined length, width and height in 'Expert' mode was further used. The average of the initial 32 bead models was calculated using the program package DAMAVER (Volkov and Svergun, *J Appl Cryst* 36:860-864, 2003). In this program, the normalized spatial discrepancy (NSD) between each pair of models was computed, and the model with the lowest average NSD relative to the rest of the models was chosen as the reference model. The remaining models were superimposed onto the reference model using SUPCOMB (Kiozin and Svergun, *J Appl Cryst* 34:33-41, 2001), except that possible outliers identified by NSD criteria were discarded. The calculation using the sphere as an initial search space indicated that the RRE has a dimension of approximately 30×90×180 Å, or is roughly a flat molecule with a thickness of approximately 30 Å on one of its sides. This thickness is a little more than the diameter of an A-form duplex and is also implied by the PDDF and its second derivative (FIG. 1B). The flatness of the RRE molecule is not unexpected, as RNAs of similar sizes adopt a planar shape (Holbrook, *Ann. Rev.* Biophysics 37:445-464, 2008; Reiter et al., *Curr Opin Struct Biol* 21:319-326, 2010). The thickness of an RNA shape is closely related to the number of duplexes packed on top of each other in a parallel or anti-parallel configuration (Leontis et al., *Curr Opin Struct Biol* 16:279-287, 2006), with a dimension of approximately n-fold of 30 Å. To reduce the degeneracy among the bead models and increase the resolution, confined search space modeling based on the results of the initial calculation was employed. Thus, knowing that the overall shape of the RRE envelope is flat, the second-round calculation was performed using a confined search space of a 60×120×220 Å rectangular shape, larger than the initial RRE model. The resulting structural models were subjected to averaging and the NSD score of the 32 models calculated using this confined search space was 1.00±0.03.

SAXS/WAXS Restrained Ensemble Calculations.

The ensemble calculation was performed using an NCI-SAXS-WAXS module that is interfaced to the Xplor-NIH and a previously published protocol (Schwieters and Clore, *Biochemistry* 46:1152-1166, 2007). The NCI-SAXS program allows a simultaneous calculation of fit between the experimental and back-calculated data in both SAXS and WAXS regions. The equally sparse SAXS/WAXS data, with q ranging from 0.006 to 2.3 Å$^{-1}$ (a total of 82 data points), was used during the SAXS-restrained ensemble calculation. The difference in SAXS/WAXS curves between experimental and back-calculated data is expressed as $\chi^2$, as defined:

$$\chi^2 = \frac{1}{N-1} \sum_i^N \left[ \frac{I^{exp}(q_i) - cI^{cal}(q_i)}{\sigma(q_i)} \right]^2$$

where c is a scaling factor, $\sigma(q_i)$ is the experimental error, and $I^{exp}(q_i)$ and $I^{cal}(q_i)$ are the experimental and back-calculated scattering intensities of the $i^{th}$ data point of the total N data points. A weighted harmonic energy potential function was used:

$$E_{SAXS} = C_{SAXS}\chi^2$$

where $C_{SAXS}$ is a scaling factor. During the calculation, the $R_g$ restraint was not turned on so that the ensemble members were allowed to freely sample space. Additional restraints were also applied to maintain covalent geometry, prevent atomic overlap and maintain canonical base pairing in duplexes. Knowledge-based restraints were applied to nucleic acid torsion angle conformations (Clore and Kuszewski, *J Am Chem Soc* 125:1518-1525, 2003) and to base-base packing (Kuszewski et al., *J Magn Reson* 125:171-177, 1997). The ensemble calculation was analyzed using an NCI-SAXS-WAXS data analysis module.

Gag Synthesis Measurements.

Gag synthesis was detected in cell lysates by Western analysis and quantified using secondary antibodies labeled with near-infrared dyes. Gag was normalized to actin levels (as a loading control) and transfection efficiency. Details are presented in Extended Experimental Procedures (below).

Electrophoretic Mobility Shift Assays.

RRE RNAs were incubated in titrating amounts of full-length Rev protein and competitor RNA as described in Extended Experimental Procedures (below). Protein-RNA complexes were resolved in non-denaturing polyacrylamide gels and detected by SYBR® Gold staining.

Construction of the RRE-Rev Dimer Complex Model.

The Rev dimer structure was docked to the RRE as described in Extended Experimental Procedures (below).

Extended Experimental Procedures

RNA Sample Preparation.

The DNA Ultramer for the 233-nt RRE RNA was synthesized (Avetra Bioscience) and used as a PCR template. The double stranded DNA containing the RRE sequence was amplified using two primers (5'-CGC GGATCCTAATACGACTCACTA-3'; SEQ ID NO: 28)) and (5'-AGTCGAATTCTGCAGGAGCTGTTGATCCTT TAGGTAT-3' (SEQ ID NO: 29)) (BamHI and EcoRI sites are underlined) and the Ultramer. After restriction digestion with the indicated enzymes, the PCR product was cloned into pUC18 using the Rapid DNA Ligation Kit (Roche). The mutant DNA templates were generated using QuikChange II Site-Directed Mutagenesis (Agilent Technologies). The templates for all RRE subconstructs used in this study were synthesized by Integrated DNA Technologies, amplified by PCR and cloned into pUC18. All cloned DNA sequences were sequenced and confirmed in both the forward and reverse directions (Macrogen). The plasmid DNAs were amplified and prepared using a Qiagen DNA prep kit (Qiagen). Plasmid DNAs were linearized and transcribed in vitro with T7 polymerase. Crude RNA was then purified by 10% polyacrylamide non-denaturing gel electrophoresis. Alternatively, RRE RNA was transcribed from a template attached to solid-phase beads. RNA samples were passively eluted from gel slices into buffer consisting of 0.3 M NaOAc, pH 5.2 and 1 mM EDTA overnight at 4° C. The RNAs were buffer exchanged into final buffer conditions containing 10 mM Tris-HCl (pH 8.0), 100 mM KCl and various concentrations of EDTA or MgCl$_2$ by extensive filtration using Amicon Ultracel-10K Centricons (Millipore). Before use, all RNA solutions were filtered using 0.2-μm filters and diluted to final concentrations (0.1-2 mg/ml) immediately prior to data collection. Homogeneity of the RNA was confirmed by non-denaturing polyacrylamide gel electrophoresis and dynamic light scattering and in some cases by mass spectroscopy. The adenine riboswitch sample with ligands for the SAXS and for electrophoretic mobility shift assay (EMSA) was prepared as described previously (Wang et al., *Biophys J* 99:3454-3462, 2009). All RRE mutants and subconstructs made for this study are listed in Table 1.

In Vivo Assays for RRE Function and In Vitro RRE-Rev Binding Studies

Development of a Simplified RRE Reporter Assay.

The Rev expression plasmid pCMV-Rev was a gift from Dr. Barbara Felber (National Cancer Institute at Frederick). The RRE reporter plasmid pCMVgagpol-RRE has been described previously (Srinivasakumar et al., *J Virol* 71:5841-5848, 1997). This plasmid was modified so that the end-product of Rev-RRE interaction, HIV-1 Gag protein, would be confined to a single band (FIG. 8C). First, the pol gene (BH10 nt 1653-6976) was deleted: the removal of protease prevents cleavage of Gag. Second, the N-terminal glycine codon was replaced with an alanine codon: this change prevents myristylation of Gag and its release from the cell in assembled particles. Initial tests showed that this plasmid directed the synthesis of Gag in transfected 293T cells only when it was co-transfected with pCMV-Rev and that the Gag protein was neither cleaved nor released from the cells, as expected. BH10 G7219 and G7301 were also replaced with adenines, so that the 233nt "core" RRE in the reporter plasmid was identical in sequence to the NL4-3 RRE analyzed by SAXS. This final reporter plasmid, referred to as "WT" herein, contains the following regions (numbering corresponds to BH10 sequence): nt 1-1651 (includes the entire gag gene and 111 nts 5' of gag) followed by nt 6977-7830 (where the 233 nt "core" corresponds to BH10 nt 7125-7357).

Construction of RRE Reporter Mutants.

Mutants were constructed by site-directed mutagenesis or inverse PCR and were confirmed by sequencing (CMV-, Gag-, and RRE-containing regions). Numbering starts with the first nucleotide of the 233 nt "core" RRE. The WT plasmid served as a template for all mutant constructions. The duplex insertion mutants had 10-, 15-, or 20-nucleotide sequences inserted at nt 36 and the corresponding complementary sequences at nt 155 (see Table 1). This was accomplished by inverse PCR with phosphorylated primers containing about 30 nucleotides complementary to the RRE sequence at their 3' ends and insert sequences (5-10 nucleotides in length) at their 5' ends. Deletion mutants were constructed by inverse PCR. The I-V mutant lacks nt 38-154 (domains II-III-IV were removed) and the II-III-IV mutant lacks nt 1-36 and 162-233 (domains I and V were removed).

Gag Synthesis Measurements.

293T cells ($2.5 \times 10^5$ cells in a 35-mm dish) were transfected with 2.5 μg of the reporter plasmid ("WT" or a mutant derivative), 2 ng of *Gaussia* Luciferase (G-LUC) expression plasmid (CMV-driven G-LUC), and 0.0625 μg of pCMV-Rev plasmid where appropriate. Cells were transfected using TransIT®-293 Transfection Reagent (Mirus). Twenty-four hours after transfection, culture media were collected and assayed for G-LUC, as a measure of transfection efficiency. G-LUC assays were performed using the BioLux® kit according to the manufacturer's instructions (New England Biolabs). Transfected cells were collected in 10 mM Tris, pH 7.4 buffer containing 10 mM NaCl, 1 mM EDTA, 0.5% Triton-X-100 and lysed by sonication: 5 pulses: 3 sec on/2 sec off at 25% amplitude (Ultrasonic Processor, Sonics and Materials). The amount of Gag in the cell lysates was measured by near infra-red quantitative Western blots using LI-COR Biosciences reagents as recommended by the manufacturer. Membranes were incubated overnight with a mixture of goat anti-p24$^{CA}$ and monoclonal mouse anti-β-actin (Sigma-Aldrich) antibodies at 1:10,000 and 1:4,000 dilutions, respectively. IRDye® 800CW donkey anti-goat (1:20,000) and IRDye® 680LT donkey anti-mouse (1:10,000) were used as secondary antibodies. Thus, a single lane of the gel was used for both the Gag and the actin measurements on each sample. The Odyssey Imaging system was used to detect and quantify protein bands (LI-COR Biosciences). The Gag signal was linearly related to the amount of sample loaded on the gel under these conditions. Gag detected by anti-p24$^{CA}$ was normalized to cellular actin levels and to transfection efficiency as measured by the G-LUC assay.

Electrophoretic Mobility Shift Assays.

Full-length Rev protein was prepared as described previously (DiMattia et al., *Proc Natl Acad Sci USA* 107:5810-5814, 2010; Watts et al., *Nature* 460:711-716. 2009). WT and mutant RRE RNAs were prepared as described above. EMSAs were adapted from Daugherty et al. (*Mol Cell* 31:824-834, 2008). Rev-binding reactions were performed in the following binding buffer: 10 mM HEPES at pH7.5, 300 mM KCl, 1 mM MgCl$_2$, 0.5 mM EDTA, and Superase-In RNase inhibitor (Ambion) at 0.67 units/l. RRE RNA (0.6 pmol) in binding buffer was incubated with titrating amounts of Rev (serially diluted in 5 mM Tris at pH 8.0, 20 mM NaCl, and 0.2 mg/ml bovine serum albumin) for 25 min at room temperature (22° C.). As a non-specific competitor, adenine riboswitch RNA was added at 20-fold mass excess. Aliquots containing 0.5 pmol RRE RNA were loaded onto non-denaturing 6% or 10% polyacrylamide gels (Life Technologies) and gels were run in TBE buffer (89 mM Tris, 89 mM borate, 2 mM EDTA at pH 8.0) at room temperature for approximately 2 hours. Gels were stained using SYBR® Gold (Invitrogen) and visualized with an AlphaImager HP imager (ProteinSimple). Bands were quantified using the AlphaView software (ProteinSimple).

Dynamic Light Scattering.

Dynamic light scattering studies were performed on a DynaPro Titan instrument equipped with a temperature-controlled MicroSampler (Wyatt Technology Corp., Santa Barbara, Calif.) at a laser wavelength of 830 nm, scattering angle of 90°, in a 12-μL quartz cuvette at ambient room temperature. Each measurement consisted of thirty 10-second acquisitions. Prior to measurements, all samples were spun in a microcentrifuge for 10 min at 13,200 rpm. To obtain the hydrodynamic radii ($R_h$) and percentage of polydispersity, the intensity autocorrelation functions were fitted with a proprietary non-negative least-squares algorithm by DYNAMICS 6.7.7.9 software (Wyatt Technology Corp., Santa Barbara, Calif.).

Secondary Structure of the RRE Construct.

The minimum functional size of the RRE is about 230 nt long and the RRE construct used for this study consisted of nucleotides 7760-7992 of the HIV-1 NL4.3 sequence (GenBank accession no. AF324493). The secondary structure model proposed by Legiewicz et al. (*Proc Natl Acad Sci USA* 105:14365-14370, 2008) was used as a platform for HIV-1 RRE atomic model construction based on the SAXS envelope. This 4-stem model is comprised of a lengthy stem I interrupted in several places by purine-rich bulges, a bifurcated stem-loop II containing a high affinity Rev binding site, and stem loops III-IV and V, all connected by a 4-way RNA junction. In an alternative 5-stem model generated using the same biochemical and computational methodologies, the III-IV stem loop present in the 4-stem model is divided into two distinct stem loops (III and IV), while the other components—stem I and stem loops II and V—are nearly identical (Watts et al., *Nature* 460:711-716, 2009). Both of these models (or slight variations thereof) are prevalent in the literature (Mann et al., *J Mol Biol* 241:193-207, 1994), and it has been suggested that an equilibrium and/or transition between the two forms may exist inside the cell (Heaphy et al., *Proc Natl Acad Sci USA* 88:7366-7370, 1991; Kjems et al., *Proc Natl Acad Sci USA* 88:683-687, 1991; Malim et al., *Nature* 338:254-257, 1989; Pallesen et al., *FEBS J.* 276:4223-4232, 2009). The 4-stem model was chosen here as the basis for 3D homology modeling and molecular dynamics, since (a) the truncated RRE RNA used to generate these SAXS data is essentially the same RNA used by Legiewicz et al. (*Proc Natl Acad Sci USA* 105: 14365-14370, 2008) to generate the 4-stem model, and (b) the SAXS envelope of subconstructs used to identify the domain locations are consistent with a 4-stem secondary structure comprised of four branches linked by a central junction.

SAXS Experiments

Data Collection and Processing.

X-ray scattering measurements were carried out at room temperature at the beamlines 12ID-B &-C of the Advanced Photon Source, at the Argonne National Laboratory. The setups were adjusted to achieve scattering q values of $0.006<q<2.3$ Å$^{-1}$, where $q=(4\pi/\lambda)\sin\theta$, and $2\theta$ is the scattering angle. Twenty two-dimensional (2D) images were recorded for each buffer or sample solution using a flow cell, with the exposure time of 0.5-1 seconds to minimize radiation damage and obtain good signal-to-noise ratio. No radiation damage was observed as confirmed by the absence of systematic signal changes in sequentially collected X-ray scattering images and also confirmed later by gel electrophoresis. The 2D images were reduced to one-dimensional scattering profiles using the Matlab software package at the beamlines. Scattering profiles of the RNAs were calculated by subtracting the background buffer contribution from the sample-buffer profile. The WAXS data were used to guide accurate background subtraction for the SAXS data by tuning SAXS background subtraction to coincide with WAXS data in the overlapping q range, approximately between 0.1 and 0.20 Å$^{-1}$. The experimental radius of gyration ($R_g$) was calculated from data at low q values in the range of $qR_g<1.3$, using the Guinier approximation of $\ln I(q) \approx \ln(I(0))-R_{g2}q^2/3$. To avoid underestimation of the molecular dimension and consequent distortion in low resolution structural reconstruction, the parameter $D_{max}$ (the upper end of distance r), was chosen so that the resulting pair distance distribution function (PDDF) has a short, near zero-value tail.

Calculation of Distance Distributions.

The PDDF, P(r), can be used to approximate populated distances in a molecule:

$$P(r) = \sum_{i=1}^{N} \rho_i^2 p_0(r, R_i) + 2\sum_{i=1}^{N-1}\sum_{k=i+1}^{N} \rho_i \rho_k \bar{p}(r, d_{ik}, R_i, R_k)$$

where $p_0(r, R_i)$ is the distance distribution function of a sphere with the radius $R_i$ and electron density equal to unity, $\bar{p}(r, d_{ik}, R_i, R_k)$ is the cross-term distance distribution between the ith and kth sphere (radii $R_i$ and $R_k$) with a mutual distance $d_{ik}$, and $\rho_i$, $\rho_k$ are the electron density of the ith and kth sphere. To obtain the distance distribution of pivot points that are indicative of characteristic distances in RRE, the second derivative of the PDDF was calculated. For a biomolecule, $R_i \ll r$ and $p_0(r, R_i)$ terms are constants so that we can approximate:

$$\frac{\partial P(r)}{\partial r} = 2\sum_{i=1}^{N-1}\sum_{k=i+1}^{N} \rho_i \rho_k \frac{\partial \bar{p}(r, d_{ik}, R_i, R_k)}{\partial r}$$

The discrete forward first derivative of discrete $P(r_j)$ can be written:

$$\frac{\partial P(r_j)}{\partial r_j} = \frac{P(r_{j+1}) - P(r_j)}{r_{j+1} - r_j} = 2\sum_{i=1}^{N-1}\sum_{k=i+1}^{N} \rho_i \rho_k \frac{\bar{p}(r_{j+1}, d_{ik}) - \bar{p}(r_j, d_{ik})}{h}$$

$$\bar{p}(r_j, d_{ik}) = \begin{cases} 1, & d_{ik} \leq r_j < d_{ik} + h \\ 0, & r < d_{ik} \text{ or } r_j \geq d_{ik} + h \end{cases}, h = r_{j+1} - r_j$$

And the discrete forward second derivative of $P(r_j)$ $$\frac{\partial^2 P(r_j)}{\partial r_j^2} = \frac{P(r_{j+2}) + P(r_j) - 2P(r_{j+1})}{h^2} =$$

$$2\sum_{i=1}^{N-1}\sum_{k=i+1}^{N} \rho_i \rho_k \frac{\bar{p}(r_{j+2}, d_{ik}) + \bar{p}(r_j, d_{ik}) - 2\bar{p}(r_{j+1}, d_{ik})}{h^2}$$

In practice, the second derivative of the PDDF is obtained numerically and the result is shown in the inset in FIG. 1B.

Construction of the Putative RRE Atomic Model.

The rationale and description of the construction of the putative RRE atomic model were as follows. RNA structures are encoded at the secondary structural level and comprise modular and hierarchical domains (Cruz and Westhof, Cell 136:604-609, 2009), with tertiary interactions as stabilizing forces. Surveys of available structural databases indicated that stems consisting of canonical basepairs in RNA can be modeled as standard A-form duplexes and that bases are generally stacked, even in single-stranded regions (Wang et al., Biophys J 99:3454-3462, 2009). Special attention was given to construction of the three-way junction of domain II, the four-way junction, and the IIB and IA Rev-binding sites. First, domain II consists of a three-way junction, a commonly-observed structural element. The folding of a three-way junction is well studied and depends heavily on the length of the linkers that connect duplexes/stem loops (Lescoute and Westhof, 2006; Lilley, 2000). In general, helices connected to junctions tend to be packed side by side in parallel and anti-parallel arrangements involving interactions such as longitudinal coaxial stacking etc., resulting in a very compact structure. The three-way junction of domain II is remarkably similar to that of the purine riboswitch (Serganov et al., Chem and Bio 11:1729-1741, 2004), in terms of both overall size and length of the junction linker (FIG. 11). Therefore, the coordinates of domain II were constructed based on those of an adenine riboswitch (PDB Accession No. 1Y26). Second, the four-way junction involving stems from domains I, II, III-IV and V was constructed to be consistent with the SAXS envelopes of RRE and various constructs. In the majority of cases, based on surveys (Laing and Schlick, J Mol Biol 390:547-559, 2009), the structures of four-way junctions, designated as J (H1, H2, H3, H4), where H1 through H4 are four helices linked to the junction, are arranged in such a way that H1-H4 and H2-H3 are paired through either coaxial stacking on each other or a helix-loop-helix motif (Laing and Schlick, J Mol Biol 390:547-559, 2009). The folding of RRE seems to be no exception, where domains II (H2) and III-IV (H3) may interact with each other in the same way as domains I (H1) and V (H4), via either coaxial stacking and/or a helix-loop-helix motif, depending on the length of the linkers (Laing and Schlick, J Mol Biol 390:547-559, 2009). These arrangements are consistent with the SAXS envelopes of RRE and the sub-constructs described in the text. Third, the structural details of the high-affinity Rev-binding site in the junction region involving IIB were modeled with existing coordinates (Battiste et al., Science 273: 1547-1551, 1996).

All RRE duplexes were generated in blocks of three-basepair mosaics using the G2G program (Wang et al., Biophys J 99:3454-3462, 2009). If the target sequence could not be matched from three-basepair mosaics, two-basepair mosaics were used to generate a stretch of three-basepair building blocks. The program scans the mosaic libraries for mosaics matching in both sequence and polarities. For example, if the program cannot find building block 234, it will try to find 23 and 34 mosaics and link them to create building block 234 (Wang et al., *Biophys J* 99:3454-3462, 2009). The G2G program was also used to generate bulges, loops and linkers. The program first finds 3D templates of the bulges, loops and linkers in the database with the sequences that best match those of the RRE. If G2G could not find 3D templates with identical matching sequences from its database, it mutated the unmatched bases in the 3D templates to generate the coordinates of RRE bulges, loops and linkers. The duplexes were then linked with bulges, loops, internal loops and linkers with a layout approximately defined by the RRE envelope (Wang et al., *Biophys J* 99:3454-3462, 2009). The initial RRE model was then regularized and minimized using Xplor-NIH to remove close van der Waals contacts and to achieve the correct covalent geometry.

Characterization of the RRE Conformation Space Using SAXS.

The number of potential conformers in which a structured RNA molecule such as RRE may exist is very large. This is possible because of the presence of a number of bulges, internal loops and junctions that serve as pivot points of flexibility (Bailor et al., *Curr. Opin. Struct. Biol.* 21:296-305, 2011; Dethoff et al., *Nature* 482:322-330, 2012). Not only do multiple conformations coexist, but they also change with time (Zhang et al., *Science* 311:653-656, 2006; Zhang et al., *Nature* 450:1263-1267, 2007). Therefore, a description of large RNAs with a single conformation may not be sufficient for understanding their behavior.

Overall topological folding of RNA is defined by tertiary interactions, covalent linkage and the secondary structures, which impose very high energy barriers among conformers that differ in secondary structure (Dethoff et al., *Nature* 482:322-330, 2012). Therefore, in the ensemble calculations the duplex regions were treated as rigid, and were constrained to allow rotation and translation as rigid bodies. In contrast, in the regions and residues that are highly accessible/flexible, as indicated by chemical probing experiments, all torsion angles are allowed to move freely during the simulated-annealing ensemble calculations. This setup is consistent with the view that the origins of the RNA flexibility are at bulges, internal loops, loops, junctions and mismatches, while duplex regions are relatively rigid due to the high-energy barrier needed to disrupt basepairs in regular secondary structures (Dethoff et al., *Nature* 482:322-330, 2012). Specifically, stems consisting of residues (1-23 and 207-233), (28-36 and 194-203), (38-44 and 97-103), (105-111 and 148-154), (119-123 and 142-146), (127-129 and 135-137), (163-171 and 180-188) were set to be rigid. In addition, short tetraloop hairpins, residues 48-69 and 78-94 were also set as rigid bodies. The force constant for SAXS was set to 400 kcal/mol, which was ramped so that the calculation could sample conformation space freely without being trapped in a local minimum. The annealing temperature was set to 1,500 K, which was high enough to enable segments of duplexes to freely translate and rotate, but not so high as to disrupt basepairs in duplex regions. The use of equally-sparse SAXS for the retained ensemble calculation is necessary for accelerating the calculation without a significant loss of accuracy (Schwieters and Clore, *Biochemistry* 46:1152-1166, 2007).

Construction of the RRE-Rev Dimer Complex.

The Rev dimer (PDB Accession No. 3PLH (DiMattia et al., *Proc Natl Acad Sci USA* 107:5810-5814, 2010)) was docked to the RRE without any conformation modification needed at the interface between the Rev dimer and the IIB and IA binding sites. The interfaces between the dimer and RNA are consistent with structural information and mapping data (Daugherty et al., *Mol Cell* 31:824-834, 2008). For the purpose of constructing a low-resolution structural model, N40 (Rev monomer 1) was restrained to be in proximity to A73, G46 and G47 of site IIB of the RRE, and R38 and R41 (Rev monomer 2) in the vicinity of A206 and G24 in site IA, respectively. A local minimization was performed using Xplor-NIH to remove close van der Waals contacts.

$Mg^{2+}$ Titration.

All WT RRE RNA samples used for titration experiments were extensively exchanged into buffers containing 10 mM Tris-HCl (pH 8.00), 100 mM KCl and $MgCl_2$ concentrations of 0.0 (5.0 mM EDTA), 0.2, 0.5, 1.0, 2.0, and 4.0 mM using the Amicon ultra centrifugal filter (10K) (Millipore) for at least three times at 4° C. It is noteworthy that intracellular free $Mg^{2+}$ concentration is generally less than 1.0 mM (MacDermott, *Exp. Physiol.* 75:763-769, 1990). At each $Mg^{2+}$ concentration, SAXS for four different concentrations of RNA (around 0.4, 0.8, 1.6, 3.2 mg/ml) samples were recorded and data were extrapolated to zero concentration to account for the possible repulsive interactions. Both small angle and wide angle measurements were collected for all samples. The data quality can be assessed by inspection of the Guinier region (FIG. 2C). The shapes of the RRE RNA at each $Mg^{2+}$ concentration were calculated as described in the previous section and are shown in FIG. 2A. The $R_g$ and $D_{max}$ values of the RRE at various $Mg^{2+}$ concentrations are listed in Table 2.

TABLE 2

Basic Structural Parameters for RRE at Various $Mg^{2+}$ Concentrations.

| [$MgCl_2$] (mM) | $^aR_g$(Å) | $^bR_g$(Å) | $D_{max}$(Å) |
| --- | --- | --- | --- |
| 0.0 (5.0 mM EDTA) | 54.81 ± 0.56 | 57.26 ± 0.22 | 204 ± 2 |
| 0.2 | 53.59 ± 0.59 | 55.42 ± 0.16 | 201 ± 2 |
| 0.5 | 52.40 ± 0.42 | 54.46 ± 0.15 | 198 ± 2 |
| 1.0 | 51.33 ± 0.96 | 53.82 ± 0.24 | 196 ± 2 |
| 2.0 | 50.26 ± 0.72 | 52.84 ± 0.23 | 195 ± 2 |
| 4.0 | 50.15 ± 0.92 | 52.68 ± 0.27 | 194 ± 2 |

Buffer: 10 mM Tris-HCl at pH 8.00, 100 mM KCl;
$^a$derived from Guinier fitting;
$^b$derived from GNOM analysis Example 2

Competitive Inhibition of Rev Binding to RRE

The ability of a peptide to block Rev protein binding to RRE was tested. Compound P46 is two peptides (each SEQ ID NO: 3) linked via a disulfide bond as follows:

N-terminus-TRQARRNRRRRWRERQRCAAAA
                                |
                    AAAACRQRERWRRRRNRRAQRT-N-terminus

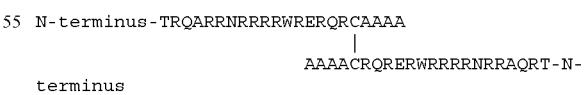

EMSA assays were carried out as described in Example 1. The P46 compound bound to the RRE, as reflected in the downward (faster mobility) shift of RRE in the presence of P46, which reflects a more compact RRE conformation (FIG. 12). P46 binds to RRE with a 1:1 stoichiometry. In the presence of increasing amounts of Rev, P46 competed with Rev and blocked its binding to RRE. There was no significant binding of Rev to RRE in the presence of P46 until Rev was present in more than 16-fold excess, as shown by the presence of slower mobility RRE-Rev complexes (P46:Rev at 1:32.0 or 1:64.0). In some cases, riboswitch RNA RibA71 was included in a 100-fold excess to show that the RRE-P46 binding was specific.

Example 3

Inhibition of HIV Viral Assembly by RRE Binding Compounds

This example describes particular methods that can be used to determine the effect of HIV RRE binding compounds disclosed herein on viral assembly and/or viability. Although particular methods are provided, one skilled in the art will appreciate that variations can be made without substantially affecting the methods.

Exemplary methods are provided in Waheed et al., *HIV Protocols: Second Edition*, Vol. 485 (Prasad et al., eds.), 2009, p. 163-184, incorporated herein by reference in its entirety. Briefly, target cells (such as HeLa cells, 293T cells, Jurkat cells, peripheral blood mononuclear cells, or macrophages) are infected with HIV-1 viral stock (such as pNL4-3 HIV-1 molecular clone) or transfected with an HIV-1 expression vector (such as pCMVNLGagPol RRE and pHCMV-G). The cells are contacted with one or more test compounds (such as the RRE binding compounds disclosed herein, for example P46, described in Example 2) for 2-96 hours (such as 4-72 hours, 12-48 hours, or 18-36 hours).

Production of virus is assessed by one or more techniques known to one of skill in the art. For example, the synthesis of an HIV protein (such as Gag) that depends on binding of Rev to RRE is measured (Fang et al., *Cell* 155:594-605, 2013). In some examples, viral particle production is assessed by metabolic labeling of the cells (for example with [$^{35}$S]Met/Cys) and detection of labeled Gag in the viral particles, for example by immunoprecipitation and SDS-PAGE. In other examples, the amount of Gag is detected by Western blotting, which does not require metabolic labeling or immunoprecipitation. In other examples, membrane binding and detergent-resistant membrane (DRM) association of viral proteins is assessed to determine the effect of a test compound on virus assembly or release. For example, following infection and treatment with one or more test compounds, the cells are metabolically labeled (for example with [$^{35}$S]Met/Cys), the cell membrane is disrupted, and the supernatant is treated with detergent (such as 0.5% TRITON®-X100). The detergent-treated sample is ultracentrifuged on a sucrose gradient and the fractions are assessed by immunoprecipitation or Western blotting. A decrease in the amount of Gag protein (for example, compared to untreated infected cells, or infected cells treated with a control compound) indicates that the RRE binding compound inhibits HIV viral production, for example, inhibits Rev binding to the RRE.

In other examples, the synthesis of Gag protein is assessed by determining multimerization of Gag, for example, based on epitope masking of Gag when it is assembled into Gag complexes. In still further examples, assembly of viral particles is detected by visualizing Gag protein by immunofluorescence or electron microscopy. A decrease in Gag multimerization or number of assembled viral particles (for example, compared to untreated infected cells, or infected cells treated with a control compound) indicates that the RRE binding compound inhibits HIV viral production, for example, inhibits Rev binding to the RRE.

Example 4

Methods of Treating or Inhibiting HIV in a Subject

This example describes a particular method that can be used to treat HIV in a human subject by administration of one or more of the disclosed compounds that bind to HIV RRE, for example, compounds that inhibit or reduce binding of Rev to a RRE. Although particular methods, dosages, and modes of administrations are provided, one skilled in the art will appreciate that variations can be made without substantially affecting the treatment.

Based upon the teaching disclosed herein, HIV, such as HIV type 1 (HIV-1) or HIV type 2 (HIV-2), can be treated or inhibited by administering an effective amount of a compound that binds RRE, such as a compound that specifically inhibits binding of Rev to the RRE. It is believed that inhibition of Rev binding to RRE reduces or eliminates transport of unspliced or singly spliced HIV RNAs from the nucleus to the cytoplasm, which in turn in reduces or eliminates HIV infection, replication or a combination thereof.

Briefly, the method may include screening subjects to determine if they have HIV, such as HIV-1 or HIV-2. Subjects having HIV are selected. In one example, subjects having increased levels of HIV antibodies in their blood (as detected with an enzyme-linked immunosorbent assay, Western blot, immunofluorescence assay), or having HIV nucleic acids in their blood (for example, as detected by HIV RNA or proviral DNA amplification methods) are selected. However, pre-screening is not required prior to administration of the therapeutic compositions disclosed herein and subjects suspected of being infected with HIV or at risk for infection with HIV are also selected in some examples.

In particular examples, the subject is treated prior to administration of a therapeutic agent that includes one or more of the compounds disclosed herein. For example, the subject can be treated with an established protocol for treatment of HIV (such as a highly active antiretroviral therapy). However, such pre-treatment is not always required, and can be determined by a skilled clinician.

Following subject selection and optional pre-treatment, an effective amount of a composition including one or more of the disclosed RRE binding compounds is administered to the subject (such as an adult human or a newborn infant at risk for contracting HIV, suspected to be infected with HIV, or known to be infected with HIV). For example, a dose of a composition including one or more of the disclosed compounds effective to reduce or inhibit binding of Rev to a RRE is administered to the subject. Additional agents, such as anti-viral agents, can also be administered to the subject simultaneously or prior to or following administration of the disclosed compounds. Administration can be achieved by any method known in the art, such as oral, inhalation, intravenous, intramuscular, intraperitoneal, or subcutaneous administration.

The amount of the composition administered to prevent, reduce, inhibit, and/or treat HIV depends on the subject being treated, the severity of the infection, and the manner of administration of the therapeutic composition. Ideally, an effective amount of an agent is the amount sufficient to prevent, reduce, and/or inhibit, and/or treat the condition (e.g., HIV) in the subject without causing a substantial adverse effect in the subject. An effective amount can be readily determined by one skilled in the art, for example using routine trials establishing dose response curves. In addition, particular exemplary dosages are provided herein.

The therapeutic compositions can be administered in a single dose delivery, via continuous delivery over an extended time period, in a repeated administration protocol (for example, by a daily, weekly, or monthly repeated administration protocol).

In one specific non-limiting example, the composition is administered at doses of 5 mg to 500 mg daily (in single or divided doses). Administration of the therapeutic compositions can be taken long term (for example over a period of weeks, months or years).

Following the administration of one or more therapies, subjects having HIV (for example, HIV-1 or HIV-2) can be monitored for HIV levels (for example, a decrease in HIV levels), CD4+ T cell counts (for example, an increase in CD4+ T cells), or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

In particular examples, if subjects are stable or have a minor, mixed or partial response to treatment, they can be re-treated after re-evaluation with the same or an adjusted schedule, dosage, and/or preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 5

Methods of Detecting Cells Containing HIV

This example describes particular methods that can be used to detect cells containing HIV by contacting cells with one or more of the disclosed compounds that bind to HIV RRE linked to a detectable label. Although particular methods are described, one skilled in the art will appreciate that variations in the particular compound, detectable label, sample type, and so on, can be successfully made.

Cells that contain or are suspected to contain HIV are contacted with a disclosed RRE-binding compound linked to a detectable label. In some examples, the cells are obtained from a subject infected with HIV or suspected to be infected with HIV. A blood or tissue sample containing cells is collected from the subject. The sample can be processed, for example to isolate cells expected to contain HIV, such as CD4+ T cells, though such pre-processing is not required. The sample is contacted with the compound linked to a detectable label (for example 1 nM to 1 mM compound) and incubated under conditions sufficient for the compound to bind to HIV RRE (such as 15 minutes to 2 hours at 37° C.). The sample is optionally washed to remove compound that is not specifically bound to the RRE. The label is then detected by any suitable method. One of ordinary skill in the art can select the detection method based on the detectable label linked to the compound.

The one or more cells in the sample are determined to contain HIV if the detectable label is detected. In some examples, the cells are determined to contain HIV if the amount of label detected is greater than background or is greater (more example statistically significantly greater) than a control, such as a sample that is not contacted with the compound linked to the label or a sample contacted with the compound, but not including the label.

Example 6

Methods of Delivering a Cargo Moiety to a Cell Containing HIV

This example describes a particular method that can be used to treat HIV in a human subject by delivering a cargo moiety linked to a disclosed RRE-binding compound to cells containing HIV. Although particular methods, dosages, and modes of administrations are provided, one skilled in the art will appreciate that variations can be made without substantially affecting the method. Based upon the teaching disclosed herein, HIV, such as HIV type 1 (HIV-1) or HIV type 2 (HIV-2), can be treated or inhibited by administering an effective amount of a compound that binds RRE linked to a cargo moiety (such as a radioisotope, a free radical generator, an RNA cleavage agent, nucleic acid crosslinking agent, and/or a cytotoxin) to a subject, thereby killing cells infected with HIV, which in turn in reduces or eliminates HIV infection, replication or a combination thereof.

Subjects can be selected as described in Example 4. The amount of the composition administered depends on the subject being treated, the severity of the infection, and the manner of administration of the therapeutic composition. Ideally, an effective amount of an agent is the amount sufficient to prevent, reduce, and/or inhibit, and/or treat the condition (e.g., HIV) in the subject without causing a substantial adverse effect in the subject. An effective amount can be readily determined by one skilled in the art, for example using routine trials establishing dose response curves. In addition, particular exemplary dosages are provided herein. The therapeutic compositions can be administered in a single dose delivery, via continuous delivery over an extended time period, or in a repeated administration protocol (for example, by a daily, weekly, or monthly repeated administration protocol).

In one specific non-limiting example, the composition including the RRE-binding compound linked to a cargo moiety (such as an RRE-binding compound linked to a toxin, for example *Pseudomonas aeruginosa* exotoxin) is administered to the subject. Doses of 5 mg to 500 mg daily (in single or divided doses) may be administered to the subject. Administration of the therapeutic compositions can be taken long term (for example over a period of weeks, months or years).

Following the administration of one or more compounds including the cargo moiety, subjects having HIV (for example, HIV-1 or HIV-2) can be monitored for reductions in HIV levels, increases in a subject's CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated. In some examples, HIV nucleic acid levels in a sample from the treated subject are analyzed.

In particular examples, if subjects are stable or have a minor, mixed or partial response to treatment, they can be re-treated after re-evaluation with the same schedule or an adjusted schedule, dosage, and/or preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A compound comprising two covalently linked peptides, wherein the compound binds to a human immunodeficiency virus (HIV) Rev response element (RRE) RNA:
   wherein the RRE RNA comprises a first Rev binding site and a second Rev binding site and wherein the first peptide binds to the first Rev binding site and the second peptide binds to the second Rev binding site; and
   wherein the two peptides are joined by a linkage of about 30-80 Å; and
   wherein the first peptide binds to the first Rev binding site with an affinity of about 1 µM to 1 nM and the second peptide binds to the second Rev binding site with an affinity of about 1 mM to 1 µM; and
   wherein each of the peptides is 18 to 23 amino acids long, comprises 60-80% alpha-helical secondary structure, and comprises 40-60% arginine residues; and
   wherein the two peptides are directly or indirectly linked by a disulfide bond, a thioester bond, or a chemical crosslinker.

2. The compound of claim 1, wherein the chemical crosslinker comprises a succinimide, a carbodiimide, a maleimide or a hydrazide.

3. The compound of claim 1, wherein one or both of the peptides comprise at least one L-amino acid, at least one D-amino acid, or a combination thereof.

4. The compound of claim 1, wherein one or both of the peptides are a retro-inverso peptide.

5. A pharmaceutical composition comprising the compound of claim 1 and a pharmaceutically acceptable carrier.

6. A method of inhibiting binding of Rev to an HIV Rev response element (RRE) RNA, comprising contacting the RRE with the compound of claim 1.

7. A method of treating or inhibiting a subject infected with HIV-1, comprising administering to the subject an effective amount of the compound of claim 1.

8. The compound of claim 1, further comprising one or more detectable labels linked to the compound.

9. A method of identifying a cell containing HIV, comprising:
   contacting one or more cells with the compound of claim 8;
   detecting presence of the detectable label; and
   identifying a cell having the presence of the detectable label as a cell containing HIV.

10. The compound of claim 1, further comprising one or more cargo moieties linked to the compound.

11. A method of delivering a cargo moiety to a cell containing HIV, comprising contacting a cell containing HIV with the compound of claim 10, thereby delivering the cargo moiety to the cell containing HIV.

* * * * *

SEQUENCE LISTING

```
<160> NUMBER OF SEQ ID NOS: 39

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Thr Arg Gln Ala Arg Arg Asn Arg Arg Arg Arg Trp Arg Glu Arg Gln
1               5                   10                  15

Arg Ala Ala Ala Ala
            20

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Arg Arg Arg Asp Arg Arg Leu Arg Gln Arg Ala Arg Arg Ala Ala
1               5                   10                  15

Ala Ala

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide

<400> SEQUENCE: 3

Thr Arg Gln Ala Arg Arg Asn Arg Arg Arg Arg Trp Arg Glu Arg Gln
1               5                   10                  15

Arg Cys Ala Ala Ala Ala
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

Thr Arg Gln Ala Arg Arg Asn Arg Arg Arg Arg Trp Arg Glu Cys Gln
1               5                   10                  15

Arg Ala Ala Ala Ala Arg
            20

<210> SEQ ID NO 5
```

```
<211> LENGTH: 22
<212> TYPE: PRT
<213> ORGANISM: Artificial Sequence
<220> FEATURE:
<223> OTHER INFORMATION: Synthetic peptide

<400> SEQUENCE: 5

Thr Arg Gln Ala Arg Arg Asn Arg Arg Arg Trp Arg Glu Lys Gln
1               5                   10                  15

Arg Ala Ala Ala Ala Arg
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic peptide

<400> SEQUENCE: 6

Thr Arg Gln Ala Arg Arg Asn Arg Arg Arg Trp Arg Glu Arg Gln
1               5                   10                  15

Arg Ala Ala Ala Ala Arg
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic peptide

<400> SEQUENCE: 7

Asp Thr Arg Gln Ala Arg Arg Asn Arg Arg Arg Trp Arg Glu Cys
1               5                   10                  15

Gln Arg Ala Ala Ala Ala Arg
            20

<210> SEQ ID NO 8
<211> LENGTH: 19
<212> TYPE: PRT
<213> ORGANISM: Artificial Sequence
<220> FEATURE:
<223> OTHER INFORMATION: Synthetic peptide

<400> SEQUENCE: 8

Arg Arg Arg Asp Arg Arg Leu Arg Gln Arg Ala Arg Arg Ala Ala
1               5                   10                  15

Ala Ala Arg

<210> SEQ ID NO 9
<211> LENGTH: 19
<212> TYPE: PRT
<213> ORGANISM: Artificial Sequence
<220> FEATURE:
<223> OTHER INFORMATION: Synthetic peptide

<400> SEQUENCE: 9

Arg Arg Arg Asp Arg Arg Leu Arg Gln Arg Ala Arg Arg Ala Ala
1               5                   10                  15

Ala Ala Gly

<210> SEQ ID NO 10
<211> LENGTH: 22
```

```
<212> TYPE: PRT
<213> ORGANISM: Artificial Sequence
<220> FEATURE:
<223> OTHER INFORMATION: Synthetic peptide

<400> SEQUENCE: 10

Thr Arg Gln Ala Arg Arg Asn Arg Arg Arg Trp Arg Glu Arg Gln
1               5                   10                  15

Arg Ala Ala Ala Ala Gly
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Ala Ala Ala Ala Arg Gln Arg Glu Arg Trp Arg Arg Arg Asn Arg Arg
1               5                   10                  15

Ala Gln Arg Thr
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Ala Ala Ala Ala Arg Arg Arg Ala Arg Gln Arg Leu Arg Arg Asp Arg
1               5                   10                  15

Arg Arg

<210> SEQ ID NO 13
<211> LENGTH: 21
<212> TYPE: PRT
<213> ORGANISM: Artificial Sequence
<220> FEATURE:
<223> OTHER INFORMATION: Synthetic peptide

<400> SEQUENCE: 13

Ala Ala Ala Ala Cys Arg Gln Arg Glu Arg Trp Arg Arg Arg Asn Arg
1               5                   10                  15

Arg Ala Gln Arg Thr
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic peptide

<400> SEQUENCE: 14

Arg Ala Ala Ala Ala Arg Gln Cys Glu Arg Trp Arg Arg Arg Arg Asn
1               5                   10                  15

Arg Arg Ala Gln Arg Thr
            20

<210> SEQ ID NO 15
<211> LENGTH: 22
```

```
<212> TYPE: PRT
<213> ORGANISM: Artificial Sequence
<220> FEATURE:
<223> OTHER INFORMATION: Synthetic peptide

<400> SEQUENCE: 15

Arg Ala Ala Ala Ala Arg Gln Lys Glu Arg Trp Arg Arg Arg Asn
1               5                   10                  15

Arg Arg Ala Gln Arg Thr
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic peptide

<400> SEQUENCE: 16

Arg Ala Ala Ala Ala Arg Gln Arg Glu Arg Trp Arg Arg Arg Asn
1               5                   10                  15

Arg Arg Ala Gln Arg Thr
            20

<210> SEQ ID NO 17
<211> LENGTH: 23
<212> TYPE: PRT
<213> ORGANISM: Artificial Sequence
<220> FEATURE:
<223> OTHER INFORMATION: Synthetic peptide

<400> SEQUENCE: 17

Arg Ala Ala Ala Ala Arg Gln Cys Glu Arg Trp Arg Arg Arg Asn
1               5                   10                  15

Arg Arg Ala Gln Arg Thr Asp
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic peptide

<400> SEQUENCE: 18

Arg Ala Ala Ala Ala Arg Arg Arg Ala Arg Gln Arg Leu Arg Asp
1               5                   10                  15

Arg Arg Arg

<210> SEQ ID NO 19
<211> LENGTH: 19
<212> TYPE: PRT
<213> ORGANISM: Artificial Sequence
<220> FEATURE:
<223> OTHER INFORMATION: Synthetic peptide

<400> SEQUENCE: 19

Gly Ala Ala Ala Ala Arg Arg Arg Ala Arg Gln Arg Leu Arg Asp
1               5                   10                  15

Arg Arg Arg

<210> SEQ ID NO 20
<211> LENGTH: 22
<212> TYPE: PRT
```

```
<213> ORGANISM: Artificial Sequence
<220> FEATURE:
<223> OTHER INFORMATION: Synthetic peptide

<400> SEQUENCE: 20

Gly Ala Ala Ala Ala Arg Gln Arg Glu Arg Trp Arg Arg Arg Asn
1               5                   10                  15

Arg Arg Ala Gln Arg Thr
            20

<210> SEQ ID NO 21
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 21
acgggcaugg ga                                                          12

<210> SEQ ID NO 22
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 22
acccaugccc ga                                                          12

<210> SEQ ID NO 23
<211> LENGTH: 17
<212> TYPE: RNA
<213> ORGANISM: Artificial Sequence
<220> FEATURE:
<223> OTHER INFORMATION: Synthetic oligonucleotide

<400> SEQUENCE: 23
acggaucggg cauggga                                                     17

<210> SEQ ID NO 24
<211> LENGTH: 17
<212> TYPE: RNA
<213> ORGANISM: Artificial Sequence
<220> FEATURE:
<223> OTHER INFORMATION: Synthetic oligonucleotide

<400> SEQUENCE: 24
acccaugccc gauccga                                                     17

<210> SEQ ID NO 25
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 25
acgugacgga ucgggcaugg ga                                               22

<210> SEQ ID NO 26
<211> LENGTH: 22
<212> TYPE: RNA
<213> ORGANISM: Artificial Sequence
<220> FEATURE:
<223> OTHER INFORMATION: Synthetic oligonucleotide
```

```
<400> SEQUENCE: 26
acccaugccc gauccgucac ga                                              22

<210> SEQ ID NO 27
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 27
cuccgcgcgu aagcgcggag                                                 20

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 28
cgcggatcct aatacgactc acta                                            24

<210> SEQ ID NO 29
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 29
agtcgaattc tgcaggagct gttgatcctt taggtat                              37

<210> SEQ ID NO 30
<211> LENGTH: 233
<212> TYPE: RNA
<213> ORGANISM: Human immunodeficiency virus type 1

<400> SEQUENCE: 30
ggagcuuugu uccuuggguu cuggggagca gcaggaagga cuaugggcgc agcgucaaug      60
acgcugacgg uacaggccag acaauuauug ucugauauag uccagcagca gaacaauuug    120
cugagggcua uugaggcgca acagcaucug uugcaacuca cagucugggg caucaaacag    180
cuccaggcaa gaauccuggc uguggaaaga uaccuaaagg aucaacagcu ccu           233

<210> SEQ ID NO 31
<211> LENGTH: 119
<212> TYPE: RNA
<213> ORGANISM: Human immunodeficiency virus type 1

<400> SEQUENCE: 31
gcacuauggg cgcagcguca augacgcuga cgguacaggc cagacaauua uugucugaua     60
uagugcagca gcagaacaau uugcugaggg cuauugaggc gcaacagcau cuguugcaa    119

<210> SEQ ID NO 32
<211> LENGTH: 110
<212> TYPE: RNA
<213> ORGANISM: Artificial Sequence
<220> FEATURE:
<223> OTHER INFORMATION: Synthetic oligonucleotide - RRE domains I and V

<400> SEQUENCE: 32
```

```
gucuggggca ucaaacagcu ccaggcaaga auccuggcug uggaaagaua ccuaaaggau    60
caacagcucc uucgggagcu uuguuccuug gguucuuggg agcagcagga              110
```

<210> SEQ ID NO 33
<211> LENGTH: 134
<212> TYPE: RNA
<213> ORGANISM: Artificial Sequence
<220> FEATURE:
<223> OTHER INFORMATION: Synthetic oligonucleotide - RRE II-III-IV-X

<400> SEQUENCE: 33

```
ggacuauggg cgcagcgucu ccgcgcguaa gcgcggagac gcugacggua caggccagac    60
aauuauuguc ugauauaguc cagcagcaga acaauuugcg gagggcuauu gaggcgcaac   120
agcaucuguu gcaa                                                     134
```

<210> SEQ ID NO 34
<211> LENGTH: 130
<212> TYPE: RNA
<213> ORGANISM: Artificial Sequence
<220> FEATURE:
<223> OTHER INFORMATION: Synthetic oligonucleotide - RRE II-III-IV-C

<400> SEQUENCE: 34

```
ggaggaagga cuauggcgc agcgucaaug acgcugacgg uacaggccag acaauuauug     60
ucugauauag ccagcagag aacaauuugc ugagggcuau ugaggcgcaa cagcaucugu    120
ugcauccucg                                                          130
```

<210> SEQ ID NO 35
<211> LENGTH: 252
<212> TYPE: RNA
<213> ORGANISM: Artificial Sequence
<220> FEATURE:
<223> OTHER INFORMATION: Synthetic oligonucleotide - RRE 1-turn
      insertion construct

<400> SEQUENCE: 35

```
ggagcuuugu uccuuggguu cuugggagca gcaggacggg cauggagga cuauggcgc      60 agcgucaaug acgcugacgg uacaggccag acaauuauug ucugauauag ccagcagca    120 gaacaauuug cugagggcua uugaggcgca acagcaucug uugcacccau gcccgacuca   180
cagucugggg caucaaacag cuccaggcaa gaaucuggcu uggaaagau accuaaagga    240 ucaacagcuc cu                                                       252
```

<210> SEQ ID NO 36
<211> LENGTH: 263
<212> TYPE: RNA
<213> ORGANISM: Artificial Sequence
<220> FEATURE:
<223> OTHER INFORMATION: Synthetic oligonucleotide - RRE 1.5-turn
      insertion construct

<400> SEQUENCE: 36

```
ggagcuuugu uccuuggguu cuugggagca gcaggacgga ucgggcaugg gaggacuaug    60
ggcgcagcgu caaugacgcu gacguacag gccagacaau uauugcuga uauaguccag    120 cagcagaaca auuugcugag ggcuauugag gcgcaacagc aucuguugca cccaugcccg   180
auccgacuca cagucugggg caucaaacag cuccaggcaa gaauccuggc uguggaaaga   240
uaccuaaagg aucaacagcu ccu                                           263
```

```
<210> SEQ ID NO 37
<211> LENGTH: 273
<212> TYPE: RNA
<213> ORGANISM: Artificial Sequence
<220> FEATURE:
<223> OTHER INFORMATION: Synthetic oligonucleotide - RRE 2-turn
      insertion construct

<400> SEQUENCE: 37
ggagcuuugu uccuugggu cuugggagca gcaggacgug acggaucggg caugggagga        60
cuaugggcgc agcgucaaug acgcugacgg uacaggccag acaauuauug ucugauauag      120
uccagcagca gaacaauuug cugagggcua uugaggcgca acagcaucug uugcacccau      180
gcccgauccg ucacgacuca cagucugggg caucaaacag cuccaggcaa gaauccuggc      240
uguggaaaga uaccuaaagg aucaacagcu ccu                                   273

<210> SEQ ID NO 38
<211> LENGTH: 71
<212> TYPE: RNA
<213> ORGANISM: Artificial Sequence
<220> FEATURE:
<223> OTHER INFORMATION: Synthetic oligonucleotide - adenine riboswitch

<400> SEQUENCE: 38
ggcuucauau aauccuaaua auaugguuug ggaguuucua ccaagagccu uaaacucuug       60
auuaugaagu c                                                           71

<210> SEQ ID NO 39
<211> LENGTH: 66
<212> TYPE: RNA
<213> ORGANISM: Artificial Sequence
<220> FEATURE:
<223> OTHER INFORMATION: Synthetic oligonucleotide - RRE domain II

<400> SEQUENCE: 39
gcacuauggg cgcagcguca augacgcuga cgguacaggc cagacaauua uugucugaua       60
uagugc                                                                 66
```